United States Patent [19]
Hsueh et al.

[11] Patent Number: 5,536,264
[45] Date of Patent: Jul. 16, 1996

[54] ABSORBENT COMPOSITES COMPRISING A POROUS MACROSTRUCTURE OF ABSORBENT GELLING PARTICLES AND A SUBSTRATE

[75] Inventors: Kesyin Hsueh; Ebrahim Rezai; Yung-Wei Tai, all of Kobe, Japan

[73] Assignee: The Procter & Gamble Company, Cincinnati, Ohio

[21] Appl. No.: 142,258

[22] Filed: Oct. 22, 1993

[51] Int. Cl.$^6$ ............................ A61F 13/15; A61F 13/20
[52] U.S. Cl. .................... 604/368; 604/365; 604/372; 604/378; 604/382
[58] Field of Search ................................ 604/358–360, 604/365, 372, 367–369, 374–375, 378, 382

[56] References Cited

U.S. PATENT DOCUMENTS

| | | |
|---|---|---|
| R. 32,649 | 4/1988 | Brandt et al. . |
| 3,654,060 | 4/1972 | Goldman . |
| 3,661,154 | 5/1972 | Torr . |

(List continued on next page.)

FOREIGN PATENT DOCUMENTS

| | | |
|---|---|---|
| 49944 | 4/1982 | European Pat. Off. . |
| 122042 | 10/1984 | European Pat. Off. . |
| 159371 | 10/1985 | European Pat. Off. . |
| 205674 | 12/1986 | European Pat. Off. . |
| 318989A | 12/1987 | European Pat. Off. . |
| 248963 | 12/1987 | European Pat. Off. . |
| 303440 | 2/1989 | European Pat. Off. . |
| 304952 | 3/1989 | European Pat. Off. . |
| 312952 | 4/1989 | European Pat. Off. . |
| 317106 | 5/1989 | European Pat. Off. . |
| 318989 | 6/1989 | European Pat. Off. . |
| 325416 | 7/1989 | European Pat. Off. . |
| 233014 | 8/1989 | European Pat. Off. . |
| 326382 | 8/1989 | European Pat. Off. . |
| 349240 | 1/1990 | European Pat. Off. . |
| 349241 | 1/1990 | European Pat. Off. . |
| 372981 | 6/1990 | European Pat. Off. . |
| 401044 | 6/1990 | European Pat. Off. . |
| 0293208 | 7/1991 | European Pat. Off. . |
| 443627 | 8/1991 | European Pat. Off. . |
| 450922 | 9/1991 | European Pat. Off. . |
| 450923 | 9/1991 | European Pat. Off. . |
| 450924 | 9/1991 | European Pat. Off. . |
| 493011 | 7/1992 | European Pat. Off. . |
| 509708 | 10/1992 | European Pat. Off. . |
| 522570 | 1/1993 | European Pat. Off. . |
| 555692 | 8/1993 | European Pat. Off. . |
| 57-44627 | 3/1982 | Japan . |
| 60-147475 | 8/1985 | Japan . |
| 60-177004 | 9/1985 | Japan . |
| 60-255814 | 12/1985 | Japan . |
| 62-1112655 | 5/1987 | Japan . |
| 62-112654 | 5/1987 | Japan . |
| 62-223203 | 10/1987 | Japan . |
| 63-21902 | 1/1988 | Japan ..................... 604/368 |
| 289790 | 2/1988 | Japan . |
| 63-19215 | 4/1988 | Japan . |
| 88025935 | 8/1989 | Japan . |
| 88023846 | 8/1989 | Japan . |
| 89303789 | 9/1989 | Japan . |
| 63-109897 | 11/1989 | Japan . |
| 2227435 | 9/1990 | Japan . |
| 6-370 | 1/1994 | Japan . |
| 1483391 | 8/1977 | United Kingdom . |
| 90/08789 | 8/1990 | WIPO . |
| 91/15177 | 10/1991 | WIPO . |
| 91/15362 | 10/1991 | WIPO . |
| 91/15368 | 10/1991 | WIPO . |
| 92/16565 | 10/1992 | WIPO . |

*Primary Examiner*—Mary Beth D. Jones
*Assistant Examiner*—P. Zuttarelli
*Attorney, Agent, or Firm*—Eric W. Guttag; Carl J. Roof; E. Kelly Linman

[57] ABSTRACT

An absorbent composite having a porous absorbent macrostructure and a substrate. The porous macrostructure has interconnected absorbent gelling particles that are surface crosslinked with cationic, preferably polymeric, amino-epichlorohydrin adducts. Upon contacting liquids such as water or body exudates (e.g., urine), the porous absorbent macrostructure can swell and imbibe the liquids. The composite is useful in absorbent articles such as diapers, adult incontinence pads, and sanitary napkins are disclosed.

37 Claims, 16 Drawing Sheets

U.S. PATENT DOCUMENTS

| | | |
|---|---|---|
| 3,670,731 | 6/1972 | Harmon . |
| 3,890,974 | 6/1975 | Kozak . |
| 3,900,378 | 8/1975 | Yen et al. . |
| 3,901,236 | 8/1975 | Assarsson et al. . |
| 3,903,889 | 9/1975 | Torr .................................. 604/368 |
| 3,957,741 | 5/1976 | Rembaum et al. . |
| 4,076,663 | 2/1978 | Masuda et al. . |
| 4,076,673 | 2/1978 | Burkholder . |
| 4,093,776 | 6/1978 | Aoki et al. . |
| 4,117,184 | 9/1978 | Erickson et al. . |
| 4,127,944 | 12/1978 | Giacobello . |
| 4,132,695 | 1/1979 | Burkholder . |
| 4,154,898 | 5/1979 | Burkholder . |
| 4,172,066 | 10/1979 | Zweigle et al. . |
| 4,190,563 | 2/1980 | Bosley et al. . |
| 4,191,672 | 3/1980 | Salome et al. . |
| 4,269,188 | 5/1981 | Nishizawa et al. . |
| 4,282,121 | 8/1981 | Goodrich . |
| 4,286,082 | 8/1981 | Tsubakimoto et al. . |
| 4,394,930 | 7/1983 | Korpman . |
| 4,410,571 | 10/1983 | Korpman . |
| 4,413,995 | 11/1983 | Korpman . |
| 4,415,388 | 11/1983 | Korpman . |
| 4,429,001 | 1/1984 | Kolpin et al. . |
| 4,439,385 | 3/1984 | Kuhls et al. . |
| 4,446,261 | 5/1984 | Yamasaki et al. . |
| 4,497,930 | 2/1985 | Yamasaki et al. . |
| 4,500,670 | 2/1985 | McKinley et al. . |
| 4,541,871 | 9/1985 | Obayashi et al. . |
| 4,551,191 | 11/1985 | Kock et al. . |
| 4,560,372 | 12/1985 | Pieniak . |
| 4,578,068 | 3/1986 | Kramer et al. . |
| 4,587,308 | 5/1986 | Makita et al. . |
| 4,610,678 | 9/1986 | Weisman et al. . |
| 4,625,001 | 11/1986 | Tsubakimoto et al. . |
| 4,647,617 | 3/1987 | Satome . |
| 4,654,039 | 3/1987 | Brandt et al. . |
| 4,666,983 | 5/1987 | Tsubakimoto et al. . |
| 4,673,402 | 6/1987 | Weisman et al. . |
| 4,676,784 | 6/1987 | Erdman et al. . |
| 4,693,713 | 9/1987 | Chmelir et al. . |
| 4,699,619 | 10/1987 | Bernardin . |
| 4,708,997 | 11/1987 | Stanley, Jr. et al. . |
| 4,734,478 | 3/1988 | Tsubakimoto et al. . |
| 4,735,987 | 4/1988 | Morita et al. . |
| 4,755,560 | 7/1988 | Ito et al. . |
| 4,758,617 | 7/1988 | Tanioku et al. . |
| 4,766,173 | 8/1988 | Bailey et al. . |
| 4,783,510 | 11/1988 | Saotome . |
| 4,798,861 | 1/1989 | Johnson et al. . |
| 4,806,598 | 2/1989 | Morman . |
| 4,822,453 | 4/1989 | Dean et al. . |
| 4,824,901 | 4/1989 | Alexander et al. . |
| 4,826,880 | 5/1989 | Lesniak et al. . |
| 4,833,179 | 5/1989 | Young et al. . |
| 4,834,735 | 5/1989 | Alemany et al. . |
| 4,861,539 | 8/1989 | Allen et al. . |
| 4,880,419 | 11/1989 | Ness . |
| 4,888,231 | 12/1989 | Angstadt . |
| 4,904,249 | 2/1990 | Miller et al. . |
| 4,973,632 | 11/1990 | Nagasuna et al. . |
| 5,002,986 | 3/1991 | Fujiura et al. . |
| 5,015,245 | 5/1991 | Noda .................................. 604/358 |
| 5,047,023 | 9/1991 | Berg . |
| 5,098,423 | 3/1992 | Pieniak et al. . |
| 5,102,597 | 4/1992 | Roe et al. . |
| 5,124,188 | 6/1992 | Roe et al. . |
| 5,140,076 | 8/1992 | Hatsuda et al. . |
| 5,149,334 | 9/1992 | Lahrman et al. . |
| 5,149,335 | 9/1992 | Kellenberger et al. . |
| 5,171,781 | 12/1992 | Farrar . |
| 5,180,622 | 1/1993 | Berg et al. . |
| 5,195,999 | 3/1993 | Harada et al. . |
| 5,213,588 | 5/1993 | Wong et al. . |
| 5,248,709 | 9/1993 | Brehm . |
| 5,306,487 | 4/1994 | Karapsha et al. .................. 604/359 |
| 5,324,561 | 6/1994 | Rezai et al. .................. 428/72 |

1

ABSORBENT COMPOSITES COMPRISING A POROUS MACROSTRUCTURE OF ABSORBENT GELLING PARTICLES AND A SUBSTRATE

FIELD OF THE INVENTION

This invention relates to an absorbent composite comprising a porous, absorbent macrostructure of interconnected absorbent gelling particles and a substrate that, upon contacting liquids such as water or body exudates (e.g., urine), swells and imbibes such liquids, and is useful in absorbent articles such as diapers, adult incontinence pads, sanitary napkins, and the like. This invention particularly relates to an absorbent composite comprising porous macrostructures of connected absorbent particles that are surface crosslinked preferably with a cationic, more preferably polymeric, amino-epichlorohydrin adduct.

BACKGROUND OF THE INVENTION

Particulate, absorbent, polymeric compositions are capable of absorbing large quantities of liquids such as water and body exudates (e.g., urine) and are further capable of retaining such absorbed liquids under moderate pressures. The absorption characteristics of such polymeric compositions make them especially useful for incorporation into absorbent articles such as diapers. See, for example, U.S. Pat. No. 3,699,103 (Harper et al), issued Jun. 13, 1972, and U.S. Pat. No. 3,770,731 (Harmon), issued Jun. 20, 1972, that disclose the use of particulate, absorbent, polymeric compositions (often referred to as "hydrogels", "superabsorbents", or "hydrocolloid materials") in absorbent articles.

Conventional particulate, absorbent, polymeric compositions, however, have the limitation that the particles are not immobilized and are free to migrate during processing and/or use. Migration of the particles can lead to material handling losses during manufacturing as well as non-homogeneous incorporation of the particles into structures in which the particles are being used. A more significant problem, though, occurs when these particulate materials migrate during or after swelling in use. Such mobility leads to high resistance to liquid flow through the material due to the lack of stable interparticle capillary or liquid transport channels. This phenomenon is one form of what is commonly referred to as "gel blocking."

One attempt to overcome the performance limitations associated with absorbent particle mobility during use in absorbent articles is incorporation of the particulate, absorbent, polymeric compositions into tissue laminates, i.e. layered absorbent structures. By encapsulating the particles between tissue layers, the overall particle mobility within an absorbent structure is diminished. However, upon liquid contact, the particles within the laminate are often free to move relative to each other resulting in the breakdown of any pre-existent interparticle capillary channels.

Another attempted solution is to immobilize the particulate, absorbent, polymeric compositions by the addition of large quantities of liquid polyhydroxy compounds that act as an adhesive to hold the particles together or to a substrate. See, for example, U.S. Pat. No. 4,410,571 (Korpman), issued Oct. 18, 1983. While this approach does limit migration before and, to some extent, during swelling, the particles eventually become detached from each other in the presence of excess liquid, resulting again in the breakdown of any pre-existing capillary channels between the particles.

Another attempted solution to overcome the problem of absorbent particle mobility is to produce a superabsorbent film by extrusion of a solution of a linear absorbent polymer and subsequently crosslinking it. See, for example. U.S. Pat. No. 4,861,539 (Allen et al), issued Aug. 29, 1989 (crosslinked with a polyhydroxy compound such as a glycol or glycerol); and U.S. Pat. No. 4,076,673 (Burkholder), issued Feb. 28, 1978 (crosslinked with polyamine-polyamide epichlorohydrin adducts such as Kymene®). While these superabsorbent films may absorb significant quantities of liquids, they have limited liquid transport properties because they are essentially non-porous, i.e. lack internal capillary channels. Indeed, due to the lack of internal capillary channels, these superabsorbent films are especially prone to gel blocking.

A more recent solution proposed to overcome the problem of absorbent particle mobility is to form these particles into aggregate macrostructures, typically as sheets of bonded absorbent particles. See U.S. Pat. No. 5,102,597 (Roe et al), issued Apr. 7, 1992. These aggregate macrostructures are prepared by initially mixing the absorbent particles with a solution of a nonionic crosslinking agent, water and a hydrophilic organic solvent such as isopropanol. These nonionic crosslinking agents include polyhydric alcohols (e.g., glycerol), polyaziridine compounds (e.g., 2,2-bishydroxymethyl butanoltris[3-(1-aziridine) propionate]), haloepoxy compounds (e.g., epicholorhydrin), polyaldehyde compounds (e.g., glutaraldehyde), polyamine compounds (e.g., ethylene amine), and polyisocyanate compounds (e.g., 2,4-toluene diisocyanate), preferably glycerol. See Column 11, lines 22–54. of Roe et al.

Particulate absorbent polymer compositions of the type used in making these aggregate macrostructures usually contain multiple carboxy groups and are typically derived from polycarboxy compounds such as the polyacrylates. When using glycerol as the crosslinking agent, the hydroxy groups of the glycerol typically react with the carboxy groups of the polymers present in the absorbent particles by an esterification reaction. The crosslinked, ester bond formed by glycerol occurs not only at the surface of the absorbent particles, but also inside particles. This is due to the fact that glycerol is a nonionic, relatively small molecule that can penetrate inside the absorbent particles. The resulting internal crosslinking leads to a lower absorbent capacity for the bonded particles of the aggregate macrostructures.

Moreover, the crosslinking reaction between the hydroxy groups of the glycerol and the carboxy groups of the polymers present in the absorbent particles is relatively slow. Indeed, the glycerol treated absorbent particles are typically cured at 200° C. for 50 minutes. This provides relatively brittle sheets of bonded absorbent particles that are more difficult to handle, especially in making the ultimately desired absorbent structures. Accordingly, these brittle sheets need to be treated with a plasticizer, such as a mixture of water and glycerol, to make them relatively flexible and thus easier to handle in manufacturing absorbent structures.

In an attempt to overcome the above described problems, preferred absorbent macrostructures have been made. Such absorbent macrostructures are disclosed in co-pending, commonly-assigned U.S. application Ser. No. 955,635, to Ebrahim Rezai et al, entitled "Porous, Absorbent Macrostructures of Bonded Absorbent Particles Surface Crosslinked With Cationic Amino-Epichlorohydrin Adducts", Attorney Docket No. 4731, filed Oct. 2, 1992, incorporated herein by reference. This application discloses aggregate macrostructures of bonded absorbent particles using a crosslinking agent that: (1) reacts rapidly with the carboxy groups of the polymer present in the absorbent particles and primarily at the surface thereof to minimize absorbency effects; (2) provides improved absorbency and mechanical properties for the aggregate macrostructures; (3) provides flexible sheets of such aggregate macrostructures that can be easily made into absorbent structures used in diapers, adult incontinence pads, sanitary napkins and the like: and (4) does not necessarily require organic solvents such as isopropanol.

Despite these improvements, there remains a need to further improve the absorbency, mechanical integrity, flexibility, and utility of such crosslinked absorbent aggregate macrostructures, particularly at low basis weight (where structures are only a few particle diameters in thickness), where there is a greater tendency for individual bonded particles to break apart upon handling. Especially after these aggregate macrostructures become wet, and the gelling particles absorb water and begin to swell, they are more easily broken apart upon handling or in response to movement or external forces.

In addition, these aggregate macrostructures, though they can readily acquire liquids, have limited ability to distribute the liquid away from the point of liquid deposition. Upon addition of water to a portion of these aggregate macrostructures, in particular macrostructures in the form of sheets, the absorbent gelling particles in that portion of the macrostructure rapidly absorb the water, causing this portion to swell and expand, causing a phenomenon referred to as "waving".

Consequently, there remains a need for further improvements in such macrostructures.

Therefore, one object of the present invention is to provide an absorbent composite comprising an absorbent macrostructure of interconnected absorbent gelling particles which can distribute liquid efficiently and effectively throughout portions of the composite distant from the point of liquid deposition, without the use of secondary distribution means.

Another object of the present invention is to improve the structural integrity and strength of such absorbent composites comprising porous absorbent macrostructures prior to its becoming wet with liquids to be absorbed.

Another object of the present invention is to improve wet integrity and strength of such absorbent composites.

Still another object of the present invention is to provide a method for making such absorbent composites.

Another object of the present invention is to provide absorbent disposable articles, such as diapers and catamenials pads, which have improved liquid distribution properties.

And still another object of the present invention is to provide absorbent disposable articles such as diapers and catamenials which are very thin and flexible, and which can acquire, distribute and store liquids very well.

SUMMARY OF THE INVENTION

Briefly stated, the present invention relates to an absorbent composite comprising at least one absorbent macrostructure layer comprising a multiplicity of interconnected absorbent gelling particles, said particles comprising intermolecular crosslinked absorbent molecules, and at least one substrate bonded to the absorbent macrostructure layer by a crosslinking agent capable of crosslinking the absorbent molecules of the absorbent gelling particles.

One aspect of the invention is an absorbent composite comprising (a) a first absorbent macrostructure layer having a first and a second surface, comprising a multiplicity of interconnected absorbent gelling particles, said particles comprising a plurality of intermolecular crosslinked absorbent molecules, wherein at least a portion of the surfaces of the absorbent gelling particles are crosslinked, and (b) a first substrate having a first surface bonded to the first surface of the absorbent macrostructure layer by a crosslinking agent capable of crosslinking the absorbent molecules of the absorbent gelling particles.

In another aspect of the invention, an absorbent composite comprises (a) a plurality of absorbent macrostructure layers, each layer having a first and a second surface and comprising a multiplicity of interconnected absorbent gelling particles, said particles comprising a plurality of intermolecular crosslinked absorbent molecules, wherein at least a portion of the surfaces of the particles are crosslinked, and (b) a plurality of substrates attached, preferably bonded, alternately to the plurality of absorbent macrostructure layers by a crosslinking agent capable of crosslinking the absorbent molecules of the absorbent gelling particles.

In yet another aspect of the invention, an absorbent composite comprises (a) at least one absorbent macrostructure layer comprising a multiplicity of interconnected absorbent gelling particles comprising intermolecular crosslinked absorbent molecules, wherein at least a portion of the surfaces of the particles are crosslinked, and (b) at least one supporting means bonded to said absorbent macrostructure layer by a crosslinking agent capable of crosslinking said absorbent molecules, for supporting the bonding of said multiplicity of absorbent gelling particles.

In still another aspect of the invention, an absorbent composite comprises (a) at least one absorbent macrostructure layer comprising a multiplicity of interconnected absorbent gelling particles comprising intermolecular crosslinked absorbent molecules, wherein at least a portion of the surfaces of the particles are crosslinked, and (b) at least one distributing means bonded to said absorbent macrostructure layer by a crosslinking agent capable of crosslinking said absorbent molecules, for distributing liquid to be absorbed to said absorbent macrostructure layer.

Preferably in the absorbent gelling particles, the crosslinked surface portion has a higher level of crosslinking than the remaining portion of the particle. Also preferably, the absorbent gelling particles are connected through the crosslinked surface portions. More preferably, the crosslinking agent is a cationic amino-epichlorohydrin adduct, most preferably Kymene®.

The present invention further relates to an absorbent article. The absorbent article comprises: (i) a liquid pervious topsheet; (ii) a liquid impervious backsheet; and (iii) an absorbent assembly positioned between the topsheet and the backsheet. The absorbent assembly comprises at least one absorbent composite described above.

The present invention further relates to a method for making a layered absorbent composite from substantially water-insoluble, absorbent hydrogel-forming polymer particles. An amount of a substrate attaching means is applied to an area of a first surface of a substrate. The substrate attaching means preferably comprises a crosslinking agent in liquid form which is capable of crosslinking with the polymer of the absorbent hydrogel-forming particles and bonding with the first surface of the substrate. A predetermined amount of the absorbent hydrogel-forming polymer particles is added as a layer to the area, such that the particles become at least partially contacted with the amount of the crosslinking agent, thereby forming a layer of the absorbent polymer particles. The crosslinking agent bonds to the first surface of the substrate and crosslinks the contacted surfaces of the particles. The exposed surfaces of the layer of absorbent polymer particles are then contacted with an additional amount of a crosslinking agent to at least partially, preferably completely, crosslink the polymer at the surface of the absorbent polymer particles. Successive additional layers of absorbent gelling particles and crosslinking agent can then be applied to form an absorbent macrostructure layer of interconnected surface-crosslinked absorbent hydrogel-forming particles.

DETAILED DESCRIPTION OF ABSORBENT COMPOSITES OF THE INVENTION

A. Structure of an Absorbent Composite

Figure 1:
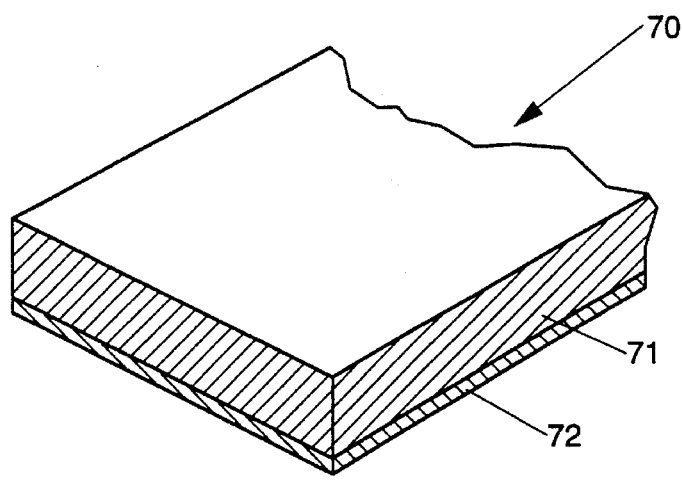
FIG. 1 is a perspective view of a continuous absorbent composite of one embodiment according to the present invention.

An absorbent composite according to the present invention can comprise a continuous composite structure wherein the absorbent macrostructure layer is substantially continuous throughout the plane of the composite. A continuous absorbent composite according to the present invention comprises a porous absorbent macrostructure layer and a substrate layer associated with, preferably attached or bonded to, the macrostructure layer. One typical example of a continuous absorbent composite structure is shown in FIG. 1.

The absorbent macrostructure layer comprises a multiplicity of interconnected absorbent gelling particles. The absorbent gelling particle are formed from absorbent polymer materials for absorbing liquids such as water and/or body exudates (e.g., urine or menses). The absorbent macrostructure layer is capable of acquiring, retaining and absorbing large quantities of such liquids. In preferred embodiments, the absorbent composite is in the form of a sheet and comprises an absorbent macrostructure layer and a substrate layer which are co-extensive in the plane of the composite, as shown in FIG. 1.

Figure 2:
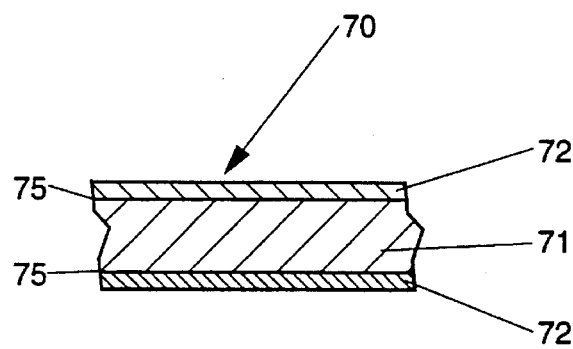
FIGS. 2, 3, 4 and 5 are sectional views of absorbent composites of other embodiments according to the present invention.
Figure 3:
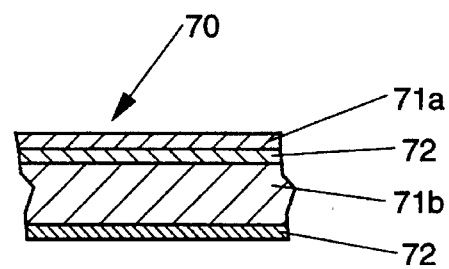
Figure 4:
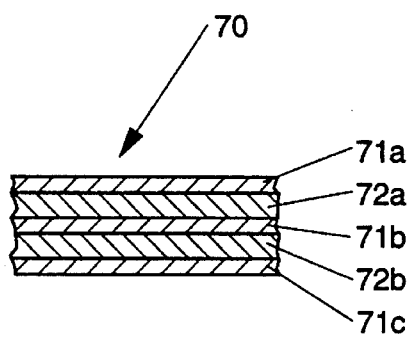
Figure 5:
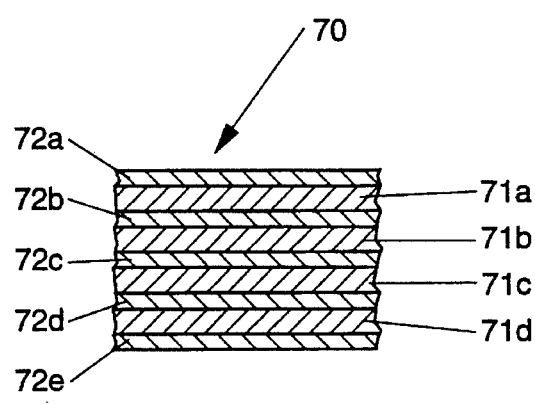
Figure 6:
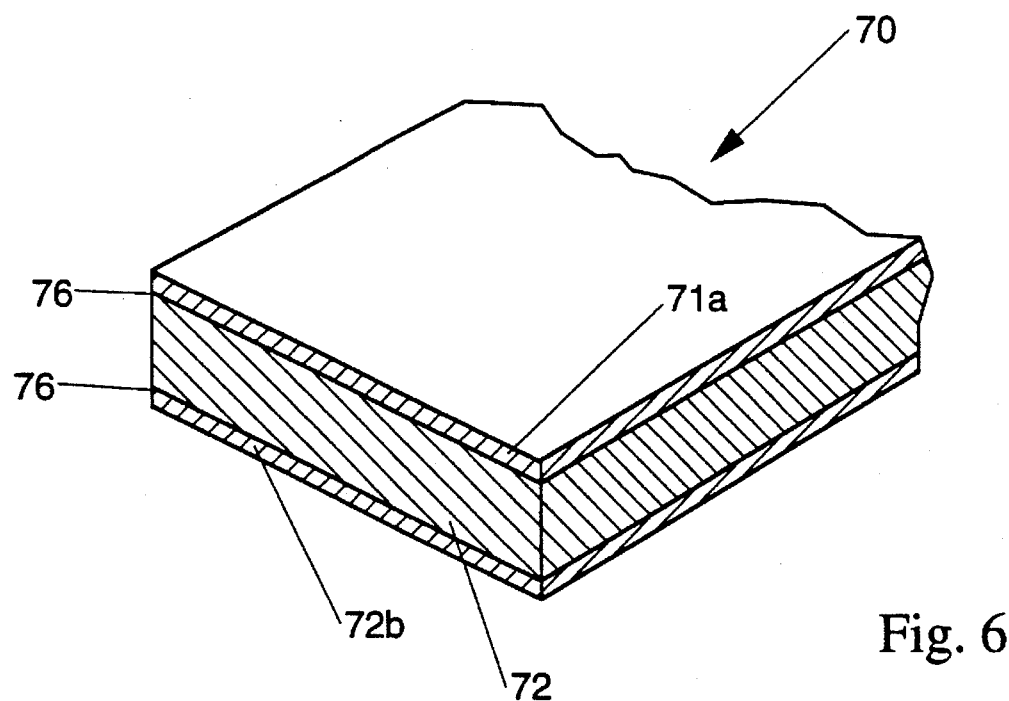
FIGS. 6, 7, 8, 9, 10, 11, and 12 are perspective views of absorbent composites of yet other embodiments according to the present invention.

The absorbent composite can comprise an additional porous absorbent macrostructure layer, or an additional substrate layer, attached or bonded thereto to form a sandwich structure as shown in FIGS. 2 and 6, respectively. In another embodiment, an continuous absorbent composite comprises a plurality of substrate layers interposed alternately between, and attached or bonded to, a plurality of porous absorbent macrostructure layers. Examples of such layered structures are shown in FIGS. 3, 4 and 5.

Figure 7:
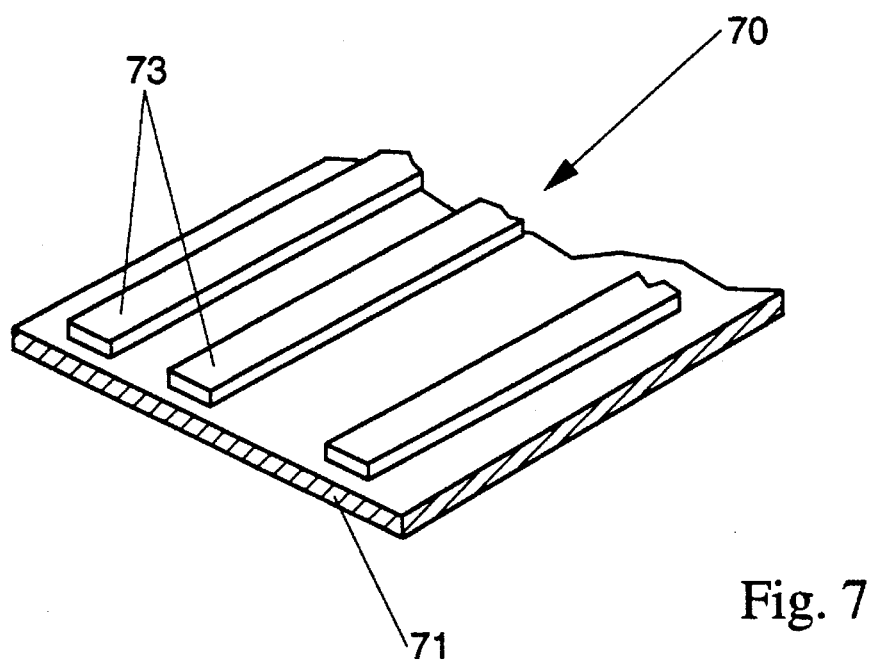

FIG. 7 shows another embodiment of a continuous absorbent composite 70 comprising a continuous absorbent macrostructure layer 71 and a substrate layer comprising a plurality of capillary elements or strands 73 of a substrate material having a length, bonded to the absorbent macrostructure layer 71.

Figure 8:
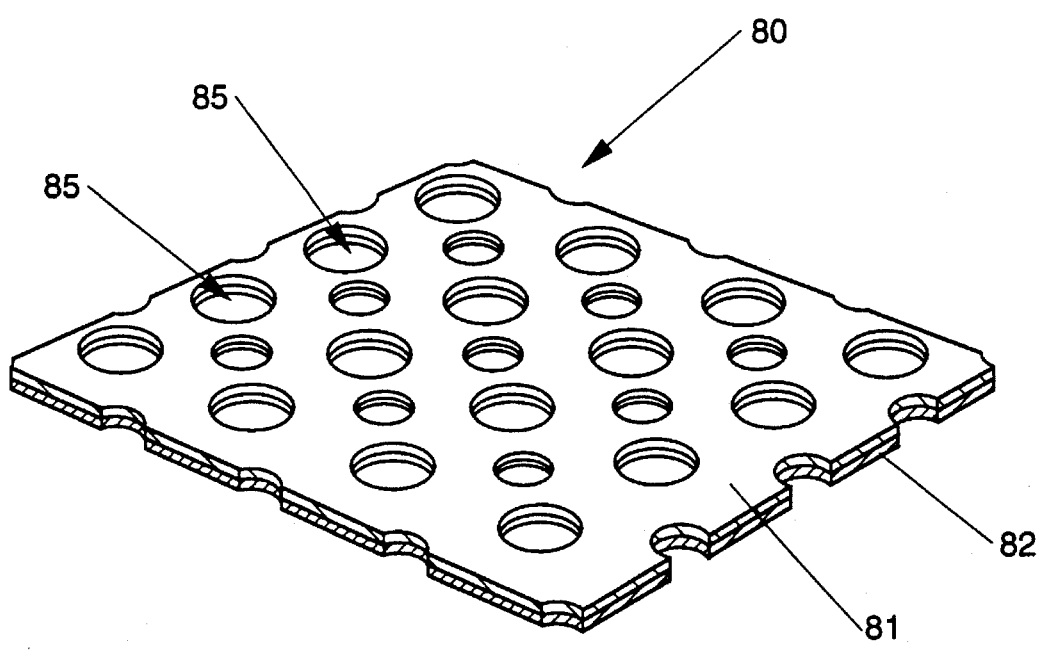
Figure 9:
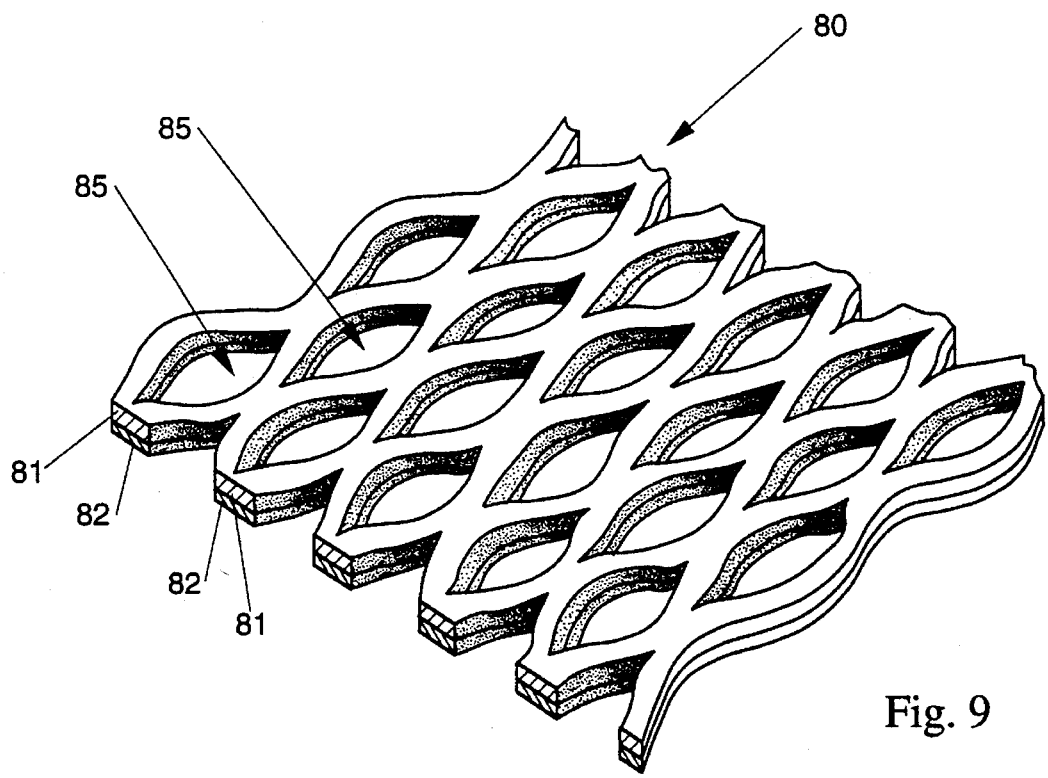

An absorbent composite according the present invention can also comprise a non-continuous composite structure having a substantial number of open voids or spaces penetrating at least partially through the plane of the absorbent composites. Preferably, such structures are formed from continuous absorbent structures described herein. Such non-continuous absorbent structures are disclosed and claimed in co-pending, commonly-assigned U.S. patent application Ser. No. 08/142,259, filed Oct. 22, 1993, Attorney Docket No. JA-67U. Examples of non-continuous composites are shown in FIGS. 8 and 9.

In a preferred embodiment, the voids or spaces extend completely through the absorbent composite. An embodiment of a non-continuous absorbent composite structure comprises a plurality of interconnected strands comprising at least one absorbent macrostructure and at least one substrate attached to the absorbent macrostructure. The macrostructure comprises a multiplicity of interconnected absorbent gelling particles. The absorbent gelling particles are preferably bonded together to form the strands. The strands are separated by a plurality of voids or spaces formed in the plane of the composite, in a preferred embodiment, the strands are directly interconnected to form the net-like structure shown in FIG. 9. In another embodiment, the strands are directly and irregularly interconnected to form a irregular net-like shape.

Upon wetting of the absorbent macrostructure, and swelling of the absorbent gelling particles in the absorbent macrostructures, the absorbent macrostructure can expand into the voids. Therefore, planar expansion of the absorbent composite can be minimized. Preferably, the planar expansion, upon wetting and swelling of the absorbent gelling particles, is less than 25% of the planar area prior to wetting, more preferably less than 15%. Most preferably, planar expansion of the absorbent composite upon wetting and swelling of the absorbent gelling particles is substantially eliminated.

Figure 10:
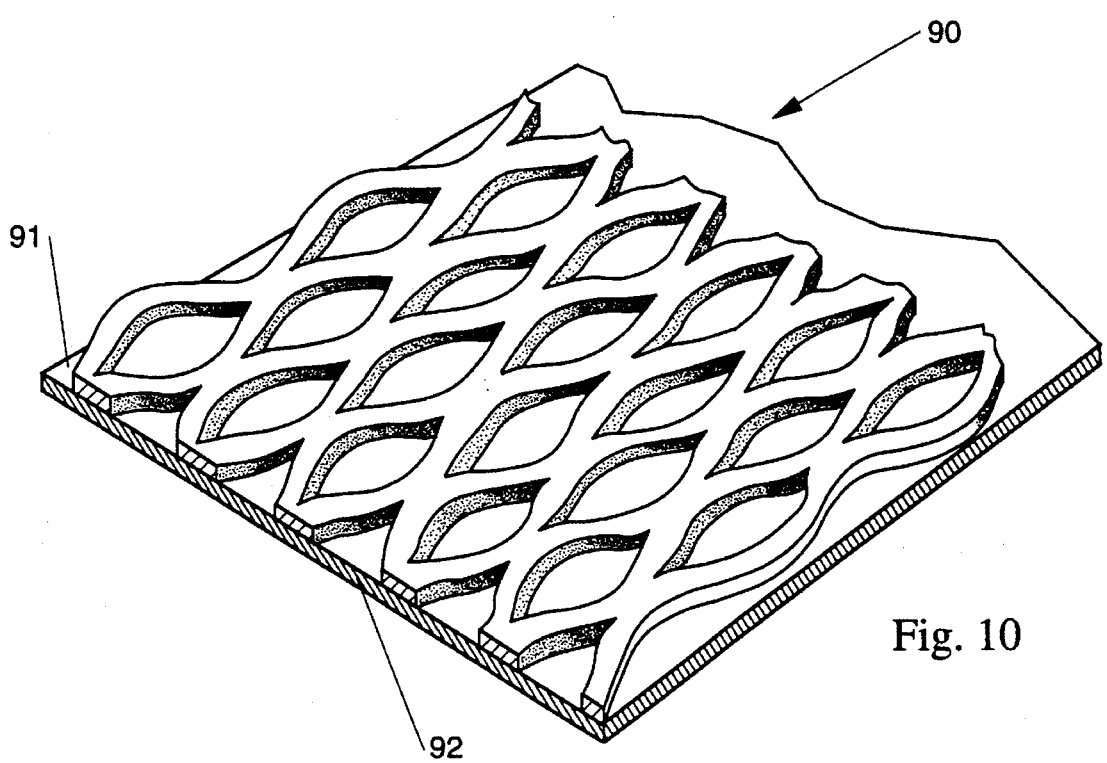
Figure 11:
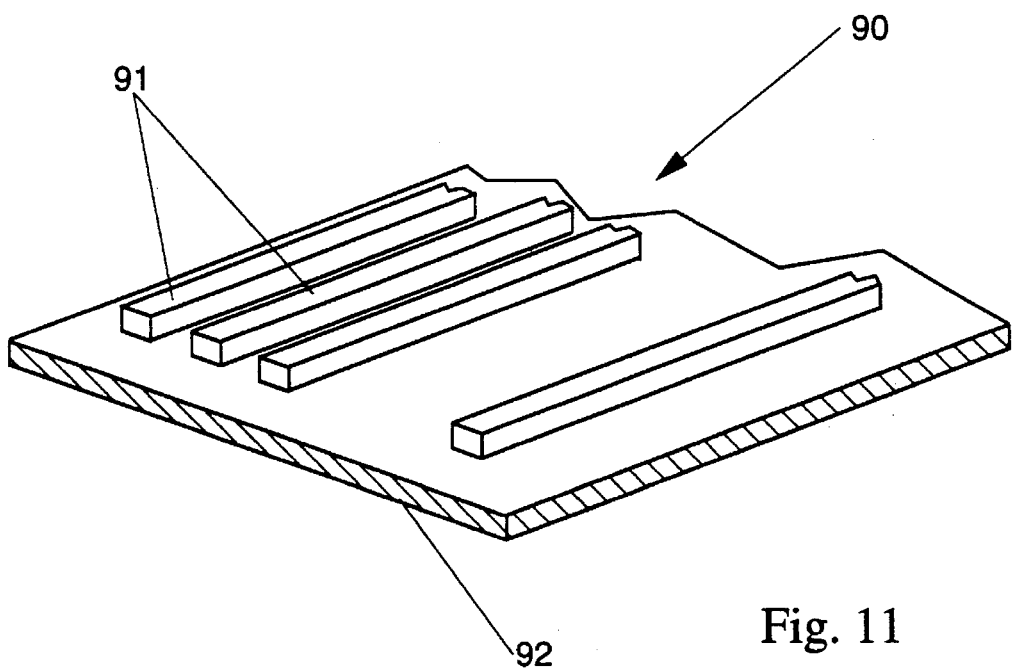
Figure 12:
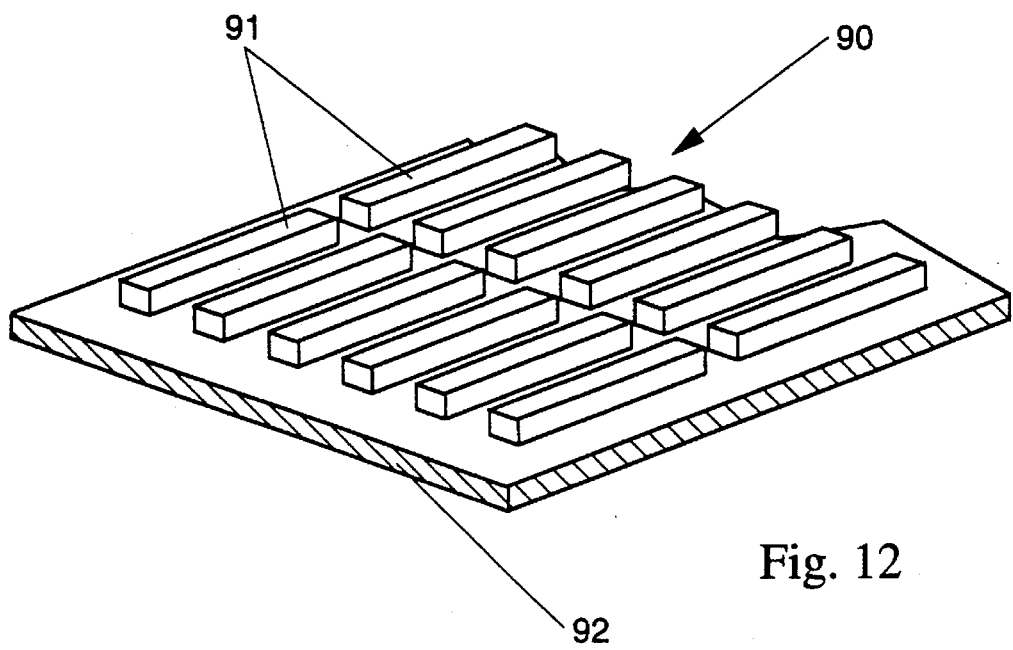

An absorbent composite according the present invention can also be semi-continuous. Preferably, such structures are formed from non-continuous absorbent structures described herein. These semi-continuous absorbent structures are disclosed and claimed in co-pending, commonly-assigned U.S. patent application Ser. No. 08/142,259, filed (Oct. 22, 1993), Attorney Docket No. JA-67U A semi-continuous composite structure of the present invention comprises at least one continuous layer selected from a substrate layer or an absorbent macrostructure layer, preferably a substrate layer, and at least one non-continuous absorbent macrostructure layer comprising a plurality of open voids or spaces penetrating completely therethrough. Preferably, the non-continuous absorbent macrostructure layer is formed from a plurality of strands of the absorbent macrostructure. The non-continuous absorbent macrostructure layer is associated with, preferably attached or bonded to, the continuous layer to form a semi-continuous absorbent composite structure, whereby interconnection of the strands in the non-continuous absorbent macrostructure layer can be made. Some examples of the semi-continuous structure are shown in FIGS. 10, 11 and 12. In another embodiment, irregularly interconnected, strands of absorbent macrostructure are attached or bonded to, the continuous layer to form a semi-continuous absorbent composite.

In a preferred embodiment, the semi-continuous composite structure of the present invention can comprise at least one continuous substrate attached to a surface of a plurality of interconnected strands. The interconnected strands comprise at least one absorbent macrostructure and at least one discrete substrate attached to the absorbent macrostructure.

Porous Absorbent Macrostructure Layer

The porous absorbent macrostructure layer of the present invention comprises interconnected absorbent gelling particles having intermolecular crosslinked absorbent molecules. The surfaces of the particles are at least partially crosslinked, preferably completely crosslinked with a crosslinking agent. More preferably, in these particles, at least a portion of the surface has a level of crosslinking between the absorbent molecules that is higher than the remaining portion of the particle. Preferably, crosslinking agents for absorbent molecules are used to form the higher level of crosslinking at these surfaces of the particles. In preferred embodiments, a cationic amino-epichlorohydrin adduct is used to chemically effect the higher-level crosslinking of the surface portions of the particles. The amino-epichlorohydrin adducts preferred for use herein as bonding agents are commercially marketed by Hercules Inc. under the trade name Kymene® Especially useful are Kymene® 557H, Kymene® 557LX and Kymene® 557 Plus. These are the epichlorohydrin adducts of polyamide-polyamine, which is the reaction product of diethylenetri-amine and adipic acid. They are typically marketed in the form of aqueous solutions of the cationic resin material containing from about 10% to about 33% by weight of the resin active.

The particles of the macrostructure are preferably attached to other adjacent absorbent gelling particles by their surfaces. Any means for interconnecting the particles can be used such that a fluid-stable macrostructure of interconnected particles is formed. For example, the interconnecting means can comprise a variety of chemical, physical, and adhesive agents. In a preferred embodiment, water-soluble and wet strength polyamide resins are used for interconnecting the particles. Adhesive means for interconnecting the particles can comprise glues, adhesives such as those which are well known in the art. Preferably, the adjacent interconnected particles are bonded together, more preferably bonded through the higher-level crosslinked surface portions. A preferred bonding material is a crosslinking agent for the polymer material of the particles. A particular preferred bonding materials is the cationic amino-epichlorohydrin adduct such as Kymene®.

Porous, absorbent macrostructures used in the absorbent composites according to the present invention are structures capable of absorbing large quantities of liquids such as water and/or body exudates (e.g., urine or menses) and then retaining such liquids under moderate pressures. Because of the particulate nature of the precursor particles, the macrostructure has pores between adjacent precursor particles. These pores are interconnected by intercommunicating channels such that the macrostructure is liquid permeable (i.e., has capillary transport channels).

Due to the crosslinking of the absorbent polymers in the interconnected surface portions of adjacent, interconnected gelling particles, the resultant absorbent macrostructure has good structural integrity, increased liquid acquisition and distribution rates, and minimal gel-blocking characteristics. When contacted with liquid, the absorbent macrostructure absorbs such liquids into the pores between the precursor particles, and then imbibes such liquids into the particles, whereby the absorbent macrostructure swells generally isotropically even under moderate confining pressures. Isotropic swelling is used herein to mean that the macrostructure swells generally equally in all directions when wetted. Isotropic swelling is an important property of the macrostructure because the absorbent gelling particles and their associated pores are able to maintain their relative geometry and spatial relationships even when swollen, such that the existing capillary channels are maintained, if not enlarged, during use. (The pores and the absorbent gelling particles get larger during swelling.) Thus, the macrostructure can imbibe and/or transport through itself additional loadings of liquid while not gel blocking.

An indication that crosslink bonds are being formed at the surface of the absorbent gelling particles (hereinafter also referred to as precursor particles) is that the resultant macrostructures are fluid (i.e., liquid) stable. "Fluid stable" is used herein to mean a macrostructure comprising an aggregate of interconnected particles that remains substantially intact (i.e., most of the previously independent component precursor particles remain bonded together) upon contact with or swelling (with and/or without stress) in an aqueous fluid. While this definition of fluid stability recognizes that most, preferably all, of the precursor particles remain bonded together, some of the precursor particles can dissociate themselves from the macrostructure if, for example, other particles have been subsequently water agglomerated onto it.

Fluid stability is an important feature of the absorbent macrostructure layers in the present invention because it allows the aggregate to maintain its relative structure in both the dry and swollen states, and because it immobilizes component precursor particles. In an end product such as an absorbent member or an absorbent article, fluid stability is beneficial in reducing gel blocking since precursor particles remain aggregated even when contacted with liquid, and allows one to use previously independent fine particles in an aggregate form to increase the rate of fluid uptake of the resultant macrostructure without introducing the element of gel blocking.

Fluid stability can be measured in an aggregate macrostructure by a two step process. The initial dynamic response of the aggregate macrostructure upon contact with the aqueous fluid is observed and then the fully swollen equilibrium condition of the aggregate macrostructure is observed. A test method for determining fluid stability based on these criteria is hereafter described in the Test Methods section.

As used herein, the term "macrostructure" means a structure having a circumscribed volume when substantially dry (i.e., circumscribed dry volume) of at least about 0.008 mm$^3$, preferably at least about 10.0 mm$^3$, more preferably at least about 100 mm$^3$, most preferably at least about 500 mm$^3$. Typically, the macrostructures of the present invention will have a circumscribed dry volume much greater than about 500 mm$^3$. In preferred embodiments of the present invention, the macrostructures have a circumscribed dry volume of between about 1000 mm$^3$ and about 100,000 mm$^3$.

While the macrostructures used in absorbent composites of the present invention can have a number of shapes and sizes, they are typically in the form of sheets, films, cylinders, blocks, spheres, fibers, filaments, or other shaped elements. The macrostructures will generally have a thickness or diameter between about 0.2 mm and about 10.0 mm. Preferably for use in absorbent products, the macrostructures are in the form of a sheet. The term "sheet" as used herein describes macrostructures having a thickness at least about 0.2 mm. The sheets will preferably have a thickness between about 0.5 mm and about 10 mm, typically from about 1 mm to about 3 mm.

As shown in FIGS. 13 through 16, the porous, absorbent macrostructures used in the absorbent composite of the present invention comprise aggregates of interconnected particles. These aggregates of interconnected particles usually comprise about 8 or more previously independent precursor particles. For preferred circumscribed dry volumes and sizes of the individual precursor particles used herein, these aggregates of interconnected particles typically are formed from about 100,000 or more individual precursor particles. These individual precursor particles can comprise granules, pulverulents, spheres, flakes, fibers, aggregates or agglomerates.

Figure 13:
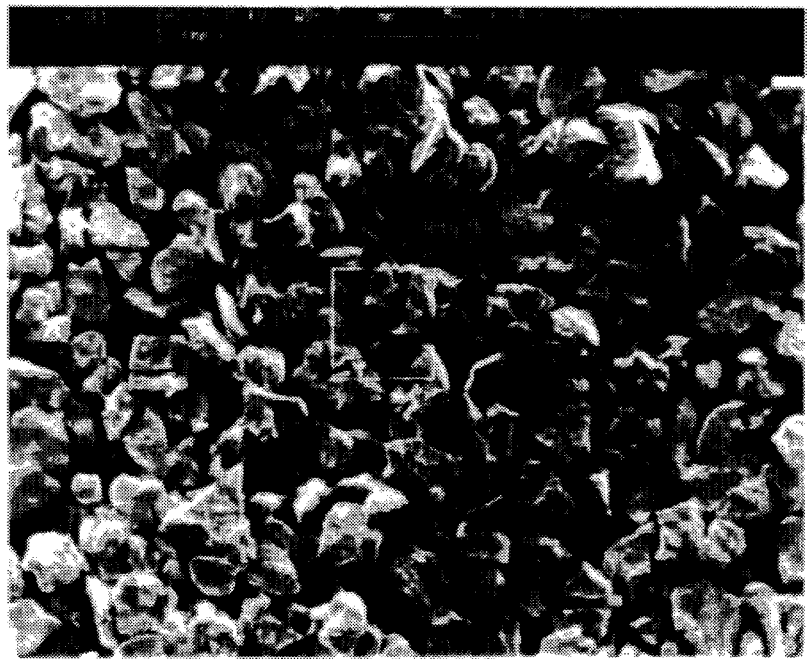
FIG. 13 is a photomicrograph (magnification 34.9×) of a section of a porous, absorbent macrostructure according to the present invention.
Figure 14:
FIG. 14 is an enlarged, portion (magnification 75×) of the macrostructure shown in FIG. 13.

As can be especially seen in FIGS. 13 and 14, the individual precursor particles can have a variety of shapes, such as cubic, rod-like, polyhedral, spherical, rounded, angular, irregular, porous-on-surface, randomly-sized irregular shapes, e.g., pulverulent products of grinding or pulverising steps, or shapes having a large greatest dimension/smallest dimension ratio so as to be needle-like, plate-like, flake-like, or fiber-like. An example of porous-on-surface precursor particles is disclosed in U.S. Pat. No. 5,118,719, issued Jun. 2, 1992, which is herein incorporated by reference.

Figure 15:
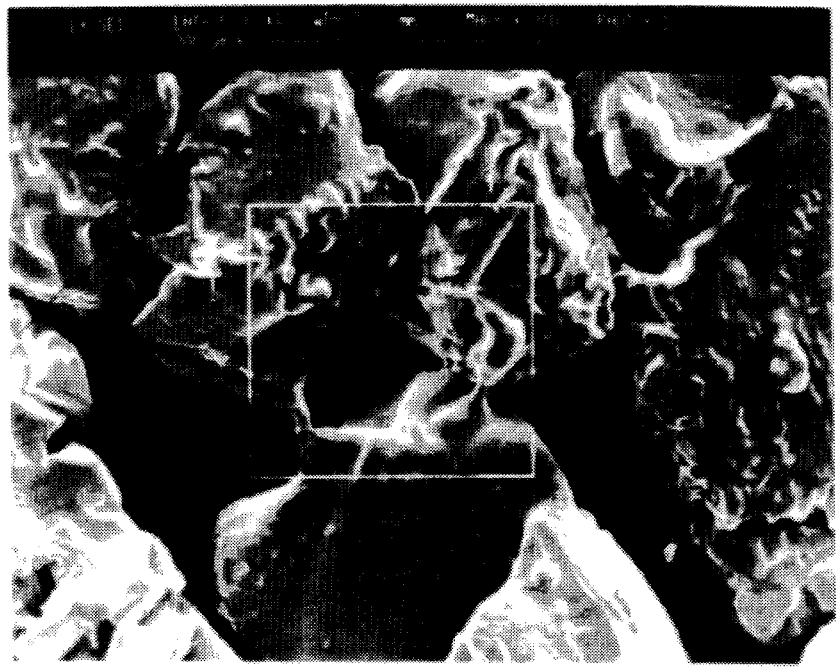
FIG. 15 is a further enlarged portion (magnification 200×) of the macrostructure shown in FIG. 14.
Figure 16:
FIG. 16 is a further enlarged portion (magnification 400×) of the macrostructure shown in FIG. 15.

As particularly shown in FIGS. 15 and 16, the aggregate of interconnected particles comprising the macrostructures of the present invention are formed, in essence, by connecting together of adjacent particles. The interconnection of adjacent particles is essentially made by the polymeric material that is present in the surface portions of these particles. Treatment of the precursor particles comprises contacting portions of their surfaces with a crosslinking agent, and a swelling agent, preferably water. In preferred embodiments, a plasticizer is also used, most preferably in combination with the treatment agent, to improve the flexibility and integrity of the porous absorbent macrostructure. When these precursor particles are treated at portions of the surface of the particles, and physically associated as described hereafter, the polymer material present in the surface portions of these particles becomes sufficiently plastic (softened) and cohesive (e.g., sticky) such that adjacent particles cohesively adhere together. When the crosslinking agent reacts with the polymer material of the interconnected surface portions of the particles, the interconnected portions become set, strong, and fast absorbing, thereby forming the porous absorbent macrostructure.

The quantity of the absorbent particles comprised in the absorbent macrostructure layer, or the thickness of the sheet of the absorbent macrostructure layer, can be varied to provide the absorbent composite with different amounts of absorbency. In preferred embodiments of an absorbent composite in the forms of a sheet, the basis weight of an absorbent macrostructure layer (expressed as weight of absorbent macrostructure per unit area of the absorbent macrostructure layer) is from about 100 g/m$^2$ to about 1500 g/m$^2$ in average, more preferably from about 250 g/m$^2$ to about 1200 g/m$^2$ in average. In addition, the absorbent macrostructure layer preferably has a density of from about 0.6 g/cc to about 1.1 g/cc.

The percent void volume (i.e., the percent of volume of the macrostructure that comprises the pores and the channels) has a minimum value for a given precursor particle size distribution. In general, when the precursor particle size distribution is more narrow, the percent volume void is higher. Thus, it is preferred, so that the precursor particles have a relatively narrow particle size distribution, to provide a higher percent volume void in a densified state. Also, in general, when the precursor particle size is larger, the percent void volume is higher.

Figure 17A:
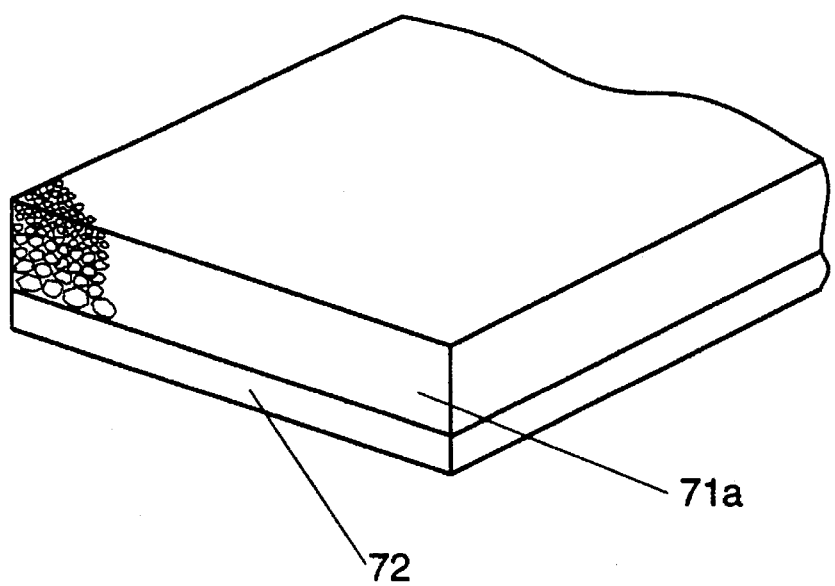
FIGS. 17A and 17B are perspective views of absorbent composites of still other embodiments according to the present invention.
Figure 17B:
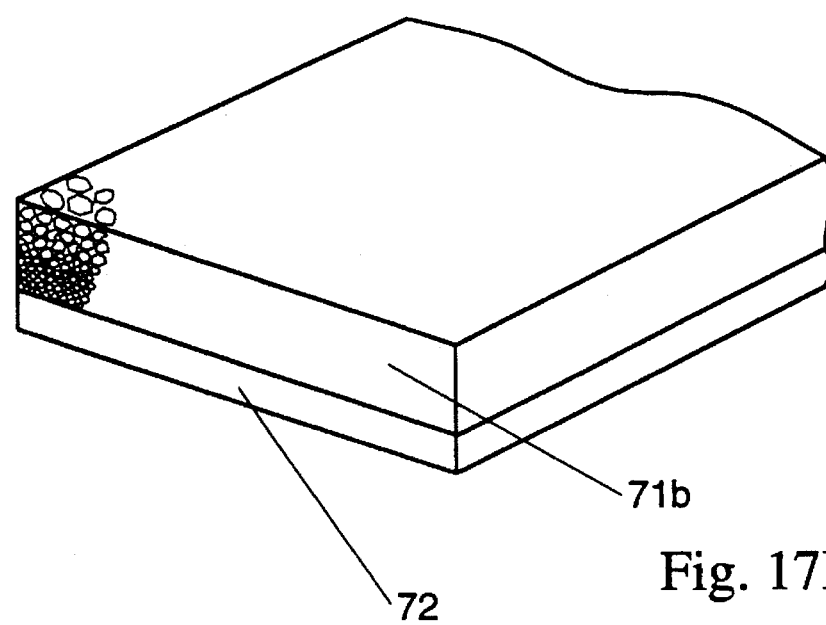

The absorbent macrostructure can also comprise a plurality of absorbent gelling particle layers each comprising absorbent gelling particles. The plurality of absorbent gelling particle layers have substantially different particle sizes at least in two adjacent particle layers. Preferably, the mass average particle sizes of the plurality of absorbent gelling particle layers are changed with successive particle layers. In one preferred embodiment shown in FIG. 17A, the absorbent macrostructure 71a comprises a plurality of layers of absorbent gelling particles where the mass average particle size of the layered particles is gradually reduced in the direction away from the substrate layer 72. On the other hand, in another embodiment shown in FIG. 17B, the macrostructure layer 71b comprises a plurality of layers of absorbent gelling particles where the mass average particle size of the layered particles is gradually increased in the direction away from the substrate layer 72. It is believed that the layering of particles of increasing (or decreasing) particle size in the porous macrostructures can provide benefits in fluid acquisition, distribution and storage. For example, in a macrostructure layer which has upper most particle layers with particles relatively larger than those in the lower most layers, the larger void areas between adjacent larger particles in the upper layers have a relatively greater porosity and fluency for the liquids, allowing a substantial portion of the fluid to pass therethrough to the lower layers. In the lower layers, because of the smaller pores and void spaces, the liquids are readily acquired and absorbed into the smaller absorbent particles, which then begin to swell. The larger particles in the upper most layer remain available to acquire and absorb additional deposits of liquid. Particularly in the case of absorbent diapers, where multiple depositions of liquids are expected, the layering of particles by size can optimize the absorbent capacity of the absorbent material.

In a similar manner, an absorbent macrostructure can comprise a plurality of particle layers wherein the absorbent gelling particles of any two layers can have different absorbent gelling particle properties. These different absorbent gelling particle properties can include, for example, different liquid absorption rate, different liquid absorption capacity, different particle shape, different particle gel strength, or combinations of these different properties. As in the case of absorbent gelling particle size, the successive layers of absorbent gelling particles can be ordered in terms of these absorbent gelling particle properties. By way of example, an absorbent macrostructure can be made by having faster absorbent gelling particles in the bottom-most layers, adjacent to the substrate, and slower absorbent gelling particles near the surface.

In an alternate embodiment, layers of absorbent gelling particles can be separated by a layer of non-absorbent-gelling material, preferably in particulate form. Such non-absorbent gelling material can include absorbent fibers or other forms as described hereinafter, or can include particulate material which can provide other functions, such as odor control.

The absorbent macrostructure layer can optionally comprise non-absorbent-gelling materials, such as non-absorbent-gelling fibers. Such fiber material can be used as reinforcing members in the macrostructure layers of the present invention, as well as a co-absorbent with the absorbent gelling particles. Any type of fiber material which is suitable for use in conventional absorbent products can be used in the macrostructures herein. Specific examples of such fiber material include cellulose fibers, modified cellulose fibers, rayon, polypropylene, and polyester fibers such as polyethylene terephthalate (DACRON), hydrophilic nylon (HYDROFIL), and the like. Examples of other fiber materials for use in the present invention in addition to some already discussed are hydrophilized hydrophobic fibers, such as surfactant-treated or silica-treated thermoplastic fibers derived, for example, from polyolefins such as polyethylene or polypropylene, polyacrylics, polyamides, polystyrenes, polyurethanes and the like. In fact, hydrophilized hydrophobic fibers which are in and of themselves not very absorbent and which, therefore, do not provide webs of sufficient absorbent capacity to be useful in conventional absorbent structures, are suitable for use in the macrostructure layers of the present invention by virtue of their good wicking properties. This is because, in the macrostructures herein, the wicking propensity of the fibers is as important, if not more important, than the absorbent capacity of the fiber material itself due to the high rate of fluid uptake and lack of gel blocking properties of the macrostructure layers in the present invention. Synthetic fibers are generally preferred for use herein as the fiber component of the macrostructure layers. Most preferred are polyolefin fibers, preferably polyethylene fibers.

Other cellulosic fiber materials which can be useful in certain macrostructure layers herein are chemically stiffened cellulosic fibers. Preferred chemically stiffened cellulosic fibers are the stiffened, twisted, curled cellulosic fibers which can be produced by internally crosslinking cellulose fibers with a crosslinking agent. Suitable stiffened, twisted, curled cellulose fibers useful as the hydrophilic fiber material herein are described in greater detail in U.S. Pat. No. 4,888,093 (Dean et al), issued Dec. 19, 1989; U.S. Pat. No. 4,889,595 (Herron et al), issued Dec. 26, 1989; U.S. Pat. No. 4,889.596 (Schoggen et al), issued Dec. 26, 1989; U.S. Pat. No. 4,889,597 (Bourbon et al), issued Dec. 26, 1989; and U.S. Pat. No. 4,898,647 (Moore et al), issued Feb. 6, 1990, all of which are incorporated by reference.

In another preferred embodiment, the absorbent macrostructure layer can optionally comprise cellulose foam particles (or granules) mixed with the absorbent gelling particles. Preferably, the cellulose foam particles have an average volume of at least about 0.1 $mm^3$, more preferably from about 1.0 $mm^3$ to about 125 $mm^3$.

As used herein, the term "hydrophilic" describes fibers or the surfaces of fibers which are wetted by the aqueous liquids deposited onto the fibers (i.e., if water or aqueous body fluid readily spreads on or over the surface of the fiber without regard to whether or not the fiber actually imbibes fluid or forms a gel). The state of the art respecting wetting of materials allows definition of hydrophobicity (and wetting) in terms of contact angles and the surface tension of the liquids and solids involved. This is discussed in detail in the American Chemical Society Publication entitled "Contact Angle, Wettability, and Adhesion edited by Robert F. Gould and copyrighted in 1964. A fiber or surface of a fiber is said to be wetted by a liquid either when the contact angle between the liquid and the fiber or surface is less than 90° or when the liquid will tend to spread spontaneously across the surface of the fiber; both conditions normally coexisting.

Other materials to provide various additional functionality. Such additional functionality can include porosity, permeability, odor control, wetness indication, structural flexibility, and structural integrity. Non-limiting examples of such other materials include : filler material, such as silica; wetness indicators; and odor control agents such as those disclosed in U.S. Pat. No. 5,161,686.

The absorbent macrostructure layer typically comprises from about 50% to about 100%, preferably from about 70% to about 100%, and more preferably about 90% a more by weight of absorbent gelling particles.

C. Absorbent Precursor Particles

The macrostructures used in the present invention are formed from polymer materials capable of absorbing large quantities of liquids. (Such polymer materials are commonly referred to as "hydrogel", "hydrocolloid", or "superabsorbent" materials.) The macrostructures preferably comprise substantially water-insoluble, absorbent hydrogel-forming, polymer material. The specific polymer materials will be discussed herein with respect to those forming the absorbent gelling particles (hereinafter also referred to as "precursor particles").

Although the precursor particles can have a size varying over a wide range, specific particle size distributions and sizes are preferred. For purposes of the present invention, particle size is defined for precursor particles that do not have a large greatest dimension/smallest dimension ratio such as fibers (e.g., granules, flakes, or pulverulents) as the dimension of a precursor particle which is determined by sieve size analysis. Thus, for example, a precursor particle that is retained on a standard #30 sieve with 600 micron openings is considered to have a particle size greater than 600 microns, a precursor particle that passes through the #30 sieve with 600 micron openings and is retained on a standard #35 sieve with 500 micron openings is considered to have a particle size between 500 and 600 microns, and a precursor particle that passes through a #35 sieve with 500 micron openings is considered to have a particle size less than 500 microns. In preferred embodiments of the present invention, the precursor particles will generally range in size from about 1 micron to about 2000 microns, more preferably from about 20 microns to about 1000 microns.

Further, for purposes of this invention, the mass average particle size of the precursor particles is important in determining the characteristics and properties of the resultant macrostructures. The mass average particle size of a given sample of precursor particles is defined as the particle size which is the average particle size of the sample on a mass basis. A method for determining the mass average particle size of a sample is described hereinafter in the Test Methods section. The mass average particle size of the precursor particles will generally be from about 20 microns to about 1500 microns, more preferably from about 50 microns to about 1000 microns, most preferably from about 50 microns to about 800 microns. In especially preferred embodiments, the mass average particle sizes is from about 100 microns to about 250 microns. The particles can be substantially uniform in size and shape, or can be randomly or ordered in size and shape. In an exemplary embodiment, at least about 95% by weight of the precursor particles have a particle size between about 150 microns and about 300 microns. In an alternative embodiment, at least about 95% by weight of the precursor particles have a particle size between about 90 microns and about 180 microns. Narrow precursor particle size distributions are preferred because they result in a higher porosity macrostructure due to the higher void fraction when densified versus broader precursor particle size distributions with equivalent mass average particle sizes.

The particle size of materials having a large greatest dimension/smallest dimension such as fibers is typically defined by their largest dimension. For example, if absorbent, polymeric fibers (i.e. superabsorbent fibers) are used in the macrostructures, the length of the fibers is used to define the "particle size." (The denier and/or the diameter of the fibers can also be specified.) In exemplary embodiments of the present invention, the fibers have a length greater than about 5 mm, preferably between about 10 mm and about 100 mm, more preferably between about 10 mm and about 50 mm.

The precursor particles comprise substantially water-insoluble, absorbent hydrogel-forming, polymer material having a multiplicity of anionic, functional groups, such as sulfonic acid, and more typically carboxy, groups. Examples of polymer materials suitable for use as the precursor particles herein include those which are prepared from polymerizable, unsaturated, acid-containing monomers. Thus, such monomers include the olefinically unsaturated acids and anhydrides which contain at least one carbon to carbon olefinic double bond. More specifically, these monomers can be selected from olefinically unsaturated carboxylic acids and acid anhydrides, olefinically unsaturated sulfonic acids, and mixtures thereof.

Some non-acid monomers can also be included, usually in minor amounts, in preparing the precursor particles herein. Such non-acid monomers can include, for example, the water-soluble or water-dispersible esters of the acid-containing monomers, as well as monomers which contain no carboxylic or sulfonic acid groups at all. Optional non-acid monomers can thus include monomers containing the following types of functional groups: carboxylic acid or sulfonic acid esters, hydroxyl groups, amide-groups, amino groups, nitrile groups and quaternary ammonium salt groups. These non-acid monomers are well-known materials and are described in greater detail, for example, in U.S. Pat. No. 4,076,663 (Masuda et al), issued Feb. 28, 1978, and in U.S. Pat. No. 4,062,817 (Westerman), issued Dec. 13, 1977, both of which are incorporated by reference.

Olefinically unsaturated carboxylic acid and carboxylic acid anhydride monomers include the acrylic acids typified by acrylic acid itself, methacrylic acid, ethacrylic acid, a-chloroacrylic acid, a-cyanoacrylic acid, b-methylacrylic acid (crotonic acid), a-phenylacrylic acid, b-acryloxypropionic acid, sorbic acid, a-chlorosorbic acid, angelic acid, cinnamic acid, p-chloro cinnamic acid, b-sterylacrylic acid, itaconic acid, citroconic acid, mesaconic acid, glutaconic acid, aconitic acid, maleic acid, fumaric acid, tricarboxyethylene and maleic acid anhydride.

Olefinically unsaturated sulfonic acid monomers include aliphatic or aromatic vinyl sulfonic acids such as vinylsulfonic acid, allyl sulfonic acid, vinyltoluene sulfonic acid and styrene sulfonic acid; acrylic and methacrylic sulfonic acid such as sulfoethyl acrylate, sulfoethyl methacrylate, sulfopropyl acrylate, sulfopropyl methacrylate, 2-hydroxy-3-methacryloxy propyl sulfonic acid and 2-acrylamide-2-methylpropane sulfonic acid.

Preferred polymer materials for use in the present invention contain carboxy groups. These polymers include hydrolyzed starch-acrylonitrile graft copolymers, partially neutralized starch-acrylonitrile graft copolymers, starch acrylic acid graft copolymers, partially neutralized starch-acrylic acid graft copolymers, saponified vinyl acetate-acrylic ester copolymers, hydrolyzed acrylonitrile or acrylamide copolymers, slightly network crosslinked polymers of any of the foregoing copolymers, partially neutralized polyacrylic acid, and slightly network crosslinked polymers of partially neutralized polyacrylic acid. These polymers can be used either solely or in the form of a mixture of two or more different polymers. Examples of these polymer materials are disclosed in U.S. Pat. No. 3,661,875, U.S. Pat. No. 4,076,663, U.S. Pat. No. 4,093,776, U.S. Pat. No. 4,666,983, and U.S. Pat. No. 4,734,478.

Most preferred polymer materials for use in making the precursor particles are slightly network crosslinked polymers of partially neutralized polyacrylic acids and starch derivatives thereof. Most preferably, the precursor particles comprise from about 50% to about 95%, preferably about 75%, neutralized, slightly network crosslinked, polyacrylic acid (i.e. poly (sodium acrylate/acrylic acid)). As described above, the precursor particles are preferably made from polymer materials that are slightly network crosslinked. Network crosslinking serves to render the polymer materials from which the precursor particles are made substantially water-insoluble and, in part, determines the absorptive capacity and extractable polymer content characteristics of the precursor particles and the resultant macrostructures. Processes for network crosslinking the polymers and typical network crosslinking agents are described in greater detail in the hereinbefore-referenced U.S. Pat. No. 4,076,663.

The individual precursor particles can be formed in any conventional manner. Typical and preferred processes for producing the individual precursor particles are described in U.S. Pat. No. Re. 32,649 (Brandt et al), issued Apr. 19, 1988, U.S. Pat. No. 4,666,983 (Tsubakimoto et al), issued May 19, 1987, and U.S. Pat. No. 4,625.001 (Tsubakimoto et al), issued Nov. 25, 1986, all of which are incorporated by reference. Preferred methods for forming the precursor particles are those that involve aqueous solution or other solution polymerization methods. As described in the above-referenced U.S. Pat. No. Re. 32,649, aqueous solution polymerization involves the use of an aqueous reaction mixture to carry out polymerization to form the precursor particles. The aqueous reaction mixture is then subjected to polymerization conditions which are sufficient to produce in the mixture, substantially water-insoluble, slightly network crosslinked polymer material. The mass of polymer material thereby formed is then pulverized or chopped to form the individual precursor particles.

More specifically, the aqueous solution polymerization method for producing the individual precursor particles comprises the preparation of an aqueous reaction mixture in which to carry out polymerization to form the desired precursor particles. One element of such a reaction mixture is the acid group-containing monomer material which will form the "backbone" of the precursor particles to be produced. The reaction mixture will generally comprise about 100 parts by weight of the monomer material. Another component of the aqueous reaction mixture comprises a network crosslinking agent. Network crosslinking agents useful in forming the precursor particles are described in more detail in the above-referenced U.S. Pat. No. Re. 32,649, U.S. Pat. No. 4,666,983, and U.S. Pat. No. 4,625, 001. The network crosslinking agent will generally be present in the aqueous reaction mixture in an amount of from about 0.001 mole percent to about 5 mole percent based on the total moles of monomer present in the aqueous mixture (about 0.01 to about 20 parts by weight, based on 100 parts by weight of the monomer material). An optional component of the aqueous reaction mixture comprises a free radical initiator including, for example, peroxygen compounds such as sodium, potassium, and ammonium persulfates, caprylyl peroxide, benzoyl peroxide, hydrogen peroxide, cumene hydroperoxides, tertiary butyl diperphthalate, tertiary butyl perbenzoate, sodium peracetate, sodium percarbonate, and the like. Other optional components of the aqueous reaction mixture comprise the various non-acidic co-monomer materials including esters of the essential unsaturated acidic functional group-containing monomers or other co-monomers containing no carboxylic or sulfonic acid functionalities at all.

The aqueous reaction mixture is subjected to polymerization conditions which are sufficient to produce in the mixture substantially water-insoluble, absorbent, hydrogel-forming, slightly network crosslinked polymer materials. The polymerization conditions are also discussed in more detail in the three above-referenced patents. Such polymerization conditions generally involve heating (thermal activation techniques) to a polymerization temperature from about 0° C. to about 100° C. , more preferably from about 5° C. to about 40° C. Polymerization conditions under which the aqueous reaction mixture is maintained can also include, for example, subjecting the reaction mixture, or portions thereof, to any conventional form of polymerization activating irradiation. Radioactive, electronic, ultraviolet, or electromagnetic radiation are alternative conventional polymerization techniques.

The acid functional groups of the polymer materials formed in the aqueous reaction mixture are also preferably neutralized. Neutralization can be carried out in any conventional manner which results in at least about 25 mole percent, and more preferably at least about 50 mole percent, of the total monomer utilized to form the polymer material being acid group-containing monomers that are neutralized with a salt-forming cation. Such salt-forming cations include, for example, alkali metals, ammonium, substituted ammonium and amines as discussed in further detail in the above-references U.S. Pat. No. Re. 32,649. While it is preferred that the precursor particles be manufactured using an aqueous solution polymerization process, it is also possible to carry out the polymerization process using multiphase polymerization processing techniques such as inverse emulsion polymerization or inverse suspension polymerization procedures. In the inverse emulsion polymerization or inverse suspension polymerization procedures, the aqueous reaction mixture as hereinbefore described is suspended in the form of tiny droplets in a matrix of a water-immiscible, inert organic solvent such as cyclohexane. The resultant precursor particles are generally spherical in shape. Inverse suspension polymerization procedures are described in greater detail in U.S. Pat. No. 4,340,706 (Obaysashi et al), issued Jul. 20, 1982, U.S. Pat. No. 4,506,052 (Flesher et al), issued Mar. 19, 1985, and U.S. Pat. No. 4,735,987 (Morita et al), issued Apr. 5, 1988, all of which are incorporated by reference.

The precursor particles are preferably substantially dry. The term "substantially dry" is used herein to mean that the precursor particles have a liquid content, typically water or other solution content, less than about 50%, preferably less than about 20%, more preferably less than about 10%, by weight of the precursor particles. Most preferably, the liquid content of the precursor particles is in the range of from about 0.01% to about 5% by weight of the precursor particles. The individual precursor particles can be dried by any conventional method such as by heating. Alternatively, when the precursor particles are formed using an aqueous reaction mixture, water can be removed from the reaction mixture by azeotropic distillation. The polymer-containing aqueous reaction mixture can also be treated with a dewatering solvent such as methanol. Combinations of these drying procedures can also be used. The dewatered mass of polymer material can then be chopped or pulverized to form substantially dry precursor particles of substantially water-insoluble, absorbent, hydrogel-forming, polymer material.

Preferred precursor particles of the present invention are those which exhibit a high absorptive capacity so that the resultant macrostructure formed from such precursor particles also has a high absorptive capacity. Absorptive capacity refers to the capacity of a given polymer material to absorb liquids with which it comes into contact. Absorptive capacity can vary significantly with the nature of the liquid being absorbed and with the manner in which the liquid contacts the polymer material. For purposes of this invention, Absorptive Capacity is defined in terms of the amount of Synthetic Urine (as hereinafter defined) absorbed by any given polymer material in terms of grams of Synthetic Urine per gram of polymer material in a procedure hereinafter defined in the Test Methods section. Preferred precursor particles of the present invention are those which have an Absorptive Capacity of at least about 20 grams, more preferably at least about 25 grams, of Synthetic Urine per gram of polymer material. Typically, the polymer materials of the precursor particles herein have an Absorptive Capacity of from about 20 grams to about 70 grams of Synthetic Urine per gram of polymer material. Precursor particles having this relatively high absorptive capacity characteristic produce macrostructures that are especially useful in absorbent products, absorbent members, and absorbent articles since the resultant macrostructures formed from such precursor particles can, by definition, hold desirably high amounts of discharged body exudates such as urine.

While all of the precursor particles are preferably formed from the same polymer material with the same properties, this need not be the case. For example, some precursor particles can comprise a starch-acrylic acid graft copolymer while other precursor particles can comprise a slightly network crosslinked polymer of partially neutralized polyacrylic acid. Further, the precursor particles can vary in size, shape, absorptive capacity, or any other property or characteristic. In a preferred embodiment of the present invention, the precursor particles consist essentially of slightly network crosslinked polymers of partially neutralized polyacrylic acid, each precursor particle having similar properties.

In another embodiment of the present invention, the precursor particles can themselves be crosslinked at least at a portion of, preferably substantially all of, their surfaces, prior to forming the precursor particles into an absorbent macrostructure. The surface crosslinking of precursor particles can be made by any of the crosslinking agents described hereinafter. Preferred crosslinking agents preferably have relatively large molecular size, and are preferably cationic. Such a crosslinking agent is unable to penetrate inside the absorbent particles, and therefore can only react with polymer material at the surface thereof effectively. Most preferably, the crosslinking agent is a cationic amino-epichlorohydrin adduct.

D. Crosslinking Agent

A crosslinking agent is used to crosslink the polymer material of the precursor particles of the absorbent macrostructure. A suitable crosslinking agent can be a nonionic crosslinking agents described in U.S. Pat. No. 5,102,597 (Roe et al), issued Apr. 7, 1992. These nonionic crosslinking agents include polyhydric alcohols (e.g., glycerol), polyaziridine compounds (e.g., 2,2-bishydroxymethyl butanoltris[3-(1-aziridine) propionate]), haloepoxy compounds (e.g., epicholorhydrin), polyaldehyde compounds (e.g., glutaraldehyde), polyamine compounds (e.g., ethylene amine), and polyisocyanate compounds (e.g., 2,4-toluene diisocyanate), preferably glycerol.

Preferred crosslinking agents are those which primarily provide crosslinking at portions of the surface of the absorbent precursor particles. Such crosslinking agents preferably have relatively large molecular size, and are preferably cationic. As a result, it is believed, such a crosslinking agent is unable to penetrate inside the absorbent particles, and therefore can only react with polymer material at the surface thereof effectively. It is possible that some such larger crosslinking agent can penetrate into the particle when the particle is swelled via the swelling agent.

Another preferred crosslinking agent is one which reacts very rapidly with the anionic, typically carboxy functional groups of the polymer material of the absorbent particles, even at a room temperature range (e.g., at from about 13° C. to about 33° C. ). As a result, fairly modest levels (e.g., as low as about 1% by weight of the particles) of such crosslinking agent are required to provide effective surface crosslinking of the polymer material present in the absorbent precursor particles.

A preferred crosslinking agent of the present invention, however, is an adduct of epichlorohydrin with certain types of monomeric or polymeric amines. These amino-epichlorohydrin adducts react with the polymer material of the absorbent precursor particles, and in particular the anionic, typically carboxy, functional groups of these polymer materials to form a covalent, ester-type bond. In other words, the amino-epichlorohydrin adduct serves to crosslink the polymer material present in the absorbent precursor particles. (The portions of the absorbent particle containing polymer material that has been effectively crosslinked with the amino-epichlorohydrin adduct swell less in the presence of aqueous body fluids relative to the other uncrosslinked portions of the particle.) Such cationic amino-epichlorohydrin adduct, especially a polymeric resin version, is relatively large such that preferential surface crosslinking is achieved. Such adduct with its cationic functional groups (e.g., azetedinium groups) can react rapidly with the polymer material at the room temperature range of preferably from about 13° C. to about 33° C., more preferably from about 18° C. to about 28° C., most preferably about 23° C.

As used herein, "cationic amino-epichlorohydrin adduct" refers to the reaction product between epichlorohydrin and a monomeric or polymeric amine such that the resulting reaction product has at least two cationic functional groups. These adducts can be in the form of monomeric compounds (e.g., the reaction product of epichlorohydrin and ethylene aliamine), or can be in polymeric form (e.g., the reaction product between epichlorohydrin, and polyamide-polyamines or polyethyleneimines). The polymeric versions of these cationic amino-epichlorohydrin adducts are typically referred to as "resins."

One type of amino compound which can be reacted with epichlorohydrin to form adducts useful in the present invention comprises monomeric di-, tri- and higher amines having primary or secondary amino groups in their structures. Examples of useful diamines of this type include bis-2-aminoethyl ether, N,N-dimethylethylenediamine, piperazine, and ethylenediamine. Examples of useful triamines of this type include N-aminoethyl piperazine, and dialkylene triamines such as diethylenetriamine, and dipropylenetriamine.

Such amine materials are reacted with epichlorohydrin to form the cationic amino-epichlorohydrin adducts useful as crosslinking agents herein. Preparation of these adducts, as well as a more complete description of the adducts themselves, can be found in U.S. Pat. No. 4,310,593 (Gross), issued Jan. 12, 1982, and in Ross et al, J. Organic Chemistry, Vol. 29, pp. 824–826 (1964). Both of these documents are incorporated by reference.

In addition to monomeric amines, polymeric amines such as polyethyleneimines can also be used as the amino compound. A particularly desirable amino compound which can be reacted with epichlorohydrin to form preferred cationic polymeric adduct resins useful herein comprise certain polyamide-polyamines derived from polyalkylene polyamines and saturated C3–C10 dibasic carboxylic acids. Epichlorohydrin/polyamide-polyamine adducts of this kind are water-soluble, thermosetting cationic polymers which are well known in the art as wet strength resins for paper products.

In the preparation of polyamide-polyamines used to form this preferred class of cationic polymeric resins, a dicarboxylic acid is first reacted with a polyalkylene-polyamine, preferably in aqueous solution, under conditions such as to produce a water-soluble, long chain polyamide containing the recurring groups —NH($C_nH_{2n}$HN)x— CORCO— where n and x are each 2 or more and R is the C1 to C8 alkylene group of the dicarboxylic acid.

A variety of polyalkylene polyamines including polyethylene polyamines, polypropylene polyamines, polybutylene polyamines and so on can be employed to prepare the polyamide-polyamine, which the polyethylene polyamines represent an economically preferred class. More specifically, preferred polyalkylene polyamines used to prepare the cationic polymeric resins herein are polyamines containing two primary amine groups and at least one secondary amine group in which the nitrogen atoms are linked together by groups of the formula —CnH2n— where n is a small integer greater than unity and the number of such groups in the molecule ranges from two up to, about eight and preferably up to about four. The nitrogen atoms can be attached to adjacent carbon atoms in the group —CnH2n— or to carbon atoms further apart, but not to the same carbon atom. Also contemplated is the use of such polyamines as diethylenetriamine, triethylene tetramine, tetraethylenepentamine, dipropylenetriamine, and the like, which can be obtained in reasonably pure form. Of all the foregoing, the most preferred are the polyethylene polyamines containing from two to four ethylene groups, two primary amine groups, and from one to three secondary amine groups.

Also contemplated for use herein are polyamine precursor materials containing at least three amino groups with at least one of these groups being a tertiary amino group. Suitable polyamines of this type include methyl bis(3-aminopropyl)amine, methyl bis(2-aminoethyl)amine, N-(2-aminoethyl) piperazine, 4,7-dimethyltriethylenetetramine and the like.

The dicarboxylic acids which can be reacted with the foregoing polyamines to form the polyamide-polyamine precursors of the preferred cationic polymeric resins useful herein comprise the saturated aliphatic C3–C10 dicarboxylic acids. More preferred are those containing from 3 to 8 carbon atoms, such as malonic, succinic, glutaric, adipic, and so on, together with diglycolic acid. Of these, diglycolic acid and the saturated aliphatic dicarboxylic acids having from 4 to 6 carbon atoms in the molecule, namely, succinic, glutaric and adipic are most preferred. Blends of two or more of these dicarboxylic acids can also be used, as well as blends of one or more of these with higher saturated aliphatic dicarboxylic acids such as azelaic and sebacic, as long as the resulting long chain polyamide-polyamine is water-soluble or at least water-dispersible.

The polyamide-polyamine materials prepared from the foregoing polyamines and dicarboxylic acids are reacted with epichlorohydrin to form the cationic polymeric aminoepichlorohydrin resins preferred for use herein as the crosslinking agent. Preparation of such materials is describe in greater detail in U.S. Pat. No. 2,926,116 (Keim), issued Feb. 23, 1960, U.S. Pat. No. 2,926,154 (Keim), issued Feb. 23, 1960, and U.S. Pat. No. 3,332,901 (Keim), issued Jul. 25, 1967, all of which are incorporated by reference.

The cationic polyamide-polyamine-epichlorohydrin resins preferred for use herein as crosslinking agents are commercially marketed by Hercules Inc. under the trade name Kymene®. Especially useful are Kymene® 557H, Kymene® 557LX and Kymene® 557 Plus, which are the epichlorohydrin adducts of polyamide-polyamines which are the reaction products of diethylenetriamine and adipic acid. They are typically marketed in the form of aqueous solutions of the cationic resin material containing from about 10% to about 33% by weight of the resin active.

E. Substrate layer

The substrate layer can provide a variety of functions. It can serve as a distributing means for improving the distribution of applied liquids to be absorbed into the macrostructure layer. Preferably, the liquid distribution properties or the substrate are substantially greater than those of the absorbent macrostructure, such that the composite has improved liquid distribution properties relative to the absorbent macrostructure alone. In preferred embodiments, the substrate layer comprises a plurality of capillary elements having a length, preferably arranged substantially in parallel, for improving the distribution of the liquid along the lengths thereof.

The substrate layer can also serve as a supporting means for the absorbent macrostructure layer by supporting the interconnected absorbent particles in the absorbent macrostructure. As described above, the absorbent gelling particles are connected to at least one of the other adjacent particles through the higher level crosslinked surface portion. The substrate layer can support the bonds or interconnection of the absorbent gelling particles by resisting the forces of stress and strain in the absorbent composite during use which might otherwise cause interconnected particles of the absorbent macrostructure layer to break apart. The supporting means is preferably one which has excellent wet strength, and can impart improved wet strength and wet integrity to the absorbent macrostructure layer: that is, the substrate is effective as a supporting means after the absorbent composite, and the substrate itself, has become wet with liquid. Support for the bonded or interconnected gelling particles is needed especially in this situation, where the gelling particles begin to swell after absorbing liquid, thereby placing substantial strain on the interparticle connections. Such support is especially important when the absorbent composite is used in an absorbent article such as a diaper or catamenial product where external forces can also act upon the structure to cause interconnected particles of the absorbent macrostructure to break apart. Therefore, the substrate layer can serve to improve both the dry integrity and strength, and the wet integrity and strength, of the absorbent composite.

The support function provided by a substrate can also permit less dense macrostructure layers. The less dense absorbent macrostructures have a higher percent void volume and larger pore openings between adjacent interconnected gelling particles, thus reducing the potential for gel blocking and reducing the stresses in the macrostructure as the particles absorb fluid and expand.

The substrate layer can be selected from various materials known in the art such as cellulose fibers, nonwoven webs, tissue webs, foams, polyacrylate fibers, apertured polymeric webs, synthetic fibers, metallic foils, elastomers, and the like. Most such substrates can serve both as a distributing means and a supporting means for the absorbent macrostructure layer. Preferably, the substrate layer is comprised of cellulosic material or a material having cellulosic functionality. Preferred substrates for use as a fluid distributing means can be selected from cellulosic materials, fibrous webs, cellulosic fibrous webs, solid foams, cellulosic foams, and polyvinyl alcohol foams. Preferred substrates for use as a supporting means can be selected from cellulosic materials, fibrous webs, nonwoven webs, fabrics, cellulosic fibrous webs, solid foams, cellulosic foams, and polyvinyl alcohol foams.

The substrate layer is preferably flexible and pliable to encourage such properties in the resulting absorbent composite. A substrate layer can be substantially resilient and non-stretchable, or it can be stretchable or deformable to a varying extent in response to forces exerted normal to and in the plane of the surface of the substrate.

The thickness and basis weight (weight per unit area of substrate) of a substrate material will vary depending on the type of substrate and the desired properties. A substrate can also comprises a plurality of individual sheets, or plies, of a particular substrate material, or a combination of one or more substrate layers in a laminate. As a typical substrate, a Bounty® sheet has a thickness of from about 0.02 mm to about 1.2 mm, more preferably from about 0.3 mm to about 0.8 mm, and a basis weight of from about 5 gm/m$^2$ to about 100 gm/m$^2$, more preferably from about 10 gm/m$^2$ to about 60 gm/m$^2$, and most preferably from about 15 gm/m$^2$ to about 40 gm/m$^2$. As another typical substrate, a cellulose foam has a dry compressed thickness of from about 0.5 mm to about 3.0 mm, more preferably from about 0.8 mm to about 2.0 mm, a wet expanded thickness of from about 0.8 mm to about 6.0 mm, more preferably from about 1.0 mm to about 5.0 mm, and a basis weight of from about 50 gm/m$^2$ to about 2,000 gm/m$^2$, more preferably from about 100 gm/m$^2$ to about 1,000 gm/m$^2$.

Substrates for use as support means typically have a dry tensile strength of from about 500 gm/in to about 8,000 gm/in, though more preferably from about 1,000 gm/in to about 3,000 gm/in, a wet tensile strength of from about 200 gm/in to about 5,000 gm/in, though more preferably from about 400 gm/in to about 1,000 gm/in, and a wet burst strength of from about 100 gm to about 2,000 gm, though more preferably from about 200 gm to about 1,000 gm, In preferred embodiments, the substrate layer comprises a cellulosic fibrous web such as paper toweling and paper tissue. Examples of such cellulosic fibrous webs are disclosed in U.S. Pat. No. 3,953,638, issued Apr. 27, 1976, U.S. Pat. No. 4,469,735, issued Sep. 4, 1984, U.S. Pat. No. 4,468,428, issued Aug. 28, 1984, and U.S. Pat. No. 4,986,882, issued Jan. 22, 1991, all herein incorporated by reference. A preferred example of such is Bounty® paper towel, commercially marketed in the U.S. by The Procter & Gamble Company. Another preferred example of such is Kinocloth® paper tissue, commercially marketed in the U.S. and Japan by Honshu Paper Co., Ltd.. Bounty® and Kinocloth® are hydrophilic and have good distribution and wicking properties, as well as good wet integrity.

In another preferred embodiment, the substrate layer comprises a cellulosic foam. In general, a cellulosic foam will provide a higher liquid wicking rate over a longer wicking distance than a cellulosic fibrous web. Preferably, the cellulosic foam is in a compressed state so as to further improve its wicking and fluid distribution properties. Suitable cellulose foam can be made of regenerated rayon fibers by well-known methods, such as those disclosed in European patent Publication (Publication No. 0,293,208), incorporated herein by reference. Such cellulose foams have numerous small cells, the size of which affect the capillarity and absorptivity of the foam. The cellulose foam layer will ordinarily, and preferably, expand when wet. A preferred cellulosic foam is one which has been compressed in the dry state prior to use. The average pore size of the cellulose foam layer can be determined by the compression. In preferred embodiments, the average pore size of the cellulose foam layer, as measured in the dry state after any compression, is from about 1 micron to about 1000 microns, preferably from about 1 micron to about 200 microns, more preferably from about 5 microns to about 70 microns. A preferred compressed cellulose Foam layer has a density of from about 0.1 g/cc (about 0.05 g/in$^3$) to about 0.8 g/cc (about 0.41 g/in$^3$) and has a compressed thickness (in sheet form) of from about 2 mm to about 5 mm. In general, better wicking properties can be obtained by using a foam layer having a higher density, or a smaller pore size. When such compressed cellulose foam layer contacts with liquids, the pore size of the foam begins to expand whereby the thickness of the foam layer become increased.

Absorbent foam substrates, particularly compressed cellulose foam substrates, are highly preferred substrates in the absorbent composites of the present invention. In addition to having excellent dry and wet strength and integrity, cellulose foam substrates, specifically in the form of sheets, have excellent capillarity and fluid wicking properties. When liquid such as water or body exudate is deposited onto the surface of an absorbent composite comprising a foam cellulose substrate, such as shown in FIG. 6, the liquid passing through the absorbent macrostructure layer and into the cellulose foam substrate is distributed quickly outward toward dry foam areas in cellulose foam layer due to its capillary suction. That is, as the cellulose foam absorbs water or aqueous liquids, the cellulose foam cell structure begins to expand. Since the dry foam areas have a cell structures which are still compressed and which are smaller than the cells of the wetted areas, fluids readily wick into the dry foam areas. Such cellulose foam substrates are characterized by excellent fluid wicking and distribution. Specifically, such cellulose foam substrates have fast wicking ratio or speed (for example, up to at least 12 cm wicking distance in 4 minutes in a vertical wicking test) and long wicking distance capability (for example, from about 20 cm to about 30 cm in the first one hour in a vertical wicking test).

In yet another embodiment, the substrate layer can be a cellulose foam substrate formed by depositing cellulose foam particles (or granules). The cellulose foam particles have an average volume of at least about 0.1 mm$^3$, preferably from about 1.0 mm$^3$ to about 125 mm$^3$. Preferably, the cellulose foam particles are deposited and compacted on an absorbent macrostructure layer.

A cellulose foam substrate is particular preferred when using the absorbent composite of the present invention in an absorbent catamenial article. When blood is deposited onto a cellulose foam substrate layer of an absorbent composite, the cellulose foam substrate can serve to acquire the blood, filter aggregates from the blood, and distribute the remaining liquid portion of the blood to the absorbent macrostructure layer below.

In yet another preferred embodiment, the substrate layer comprises a compressed or non-compressed polyvinyl alcohol foam. In general, such foam preferably has properties and structure substantially as the cellulosic foam above.

F. Bonding Between Macrostructure Layer and Substrate Layer

The bonding or interconnection between the absorbent macrostructure layer and the substrate layer can be made by a variety of chemical, physical, and adhesive agents. In a preferred embodiment, water-soluble and wet strength polyamide resins are used for bonding the substrate physically to the absorbent macrostructure layer.

Adhesive means for attaching a substrate to an absorbent macrostructure layer can comprise glues, adhesives such as those which are well known in the art. Non-limiting examples of such adhesive means include Findley H-2247 Hot Melt Adhesive, available from Findley Adhesives of Elm Grove, Wis., U.S.A., HM-6515 Hot Melt Adhesive, available from H. B. Fuller Company of St. Paul, Minn., U.S.A., Century 5227, available from Century Adhesives, Inc. of Columbus, Ohio, and HL-1258, available from H. B. Fuller Company of St. Paul, Minn.

In more preferred embodiments, the bonding between the substrate and the absorbent macrostructure layer is made by a crosslinking agent capable of crosslinking the absorbent molecules of the absorbent gelling particles in the absorbent macrostructure layer. Any crosslinking agent which is known in the art and is capable of crosslinking the absorbent molecules of the absorbent gelling particles can be used as a bonding agent. A suitable crosslinking agent can be a nonionic crosslinking agents described in U.S. Pat. No. 5,102,597 (Roe et al), issued Apr. 7, 1992. These nonionic crosslinking agents include polyhydric alcohols (e.g., glycerol), polyaziridine compounds (e.g., 2,2-bishydroxymethyl butanoltris[3-(1-aziridine) propionate] ), haloepoxy compounds (e.g., epicholorhydrin), polyaldehyde compounds (e.g., glutaraldehyde), polyamine compounds (e.g., ethylene amine), and polyisocyanate compounds (e.g., 2,4-toluene diisocyanate), preferably glycerol.

In a preferred embodiment where the substrate layer comprises cellulosic material or has cellulosic activity at least at the surface thereof, an amino-epichlorohydrin adduct is preferably used as a chemical bonding means between the cellulosic substrate and the surfaces of the absorbent gelling particles. The amino-epichlorohydrin adduct can chemically bond to carboxyl and hydroxyl groups in the cellulosic material and to the polymer material of the absorbent precursor particles, as well as to other amino-epichlorohydrin adduct molecules. Such chemical bonding can be hydrogen bonding, ionic/coulombic bonding, polymer entanglement bonding, and covalent bonding. In this manner, the amino-epichlorohydrin adduct can chemically bond together the substrate to the absorbent macrostructure layer comprising the absorbent precursor particles. The amino-epichlorohydrin adduct preferred for use herein as a bonding agent is Kymene®. Especially useful are Kymene® 557H, Kymene® 557LX and Kymene® 557 Plus. These are the epichlorohydrin adducts of polyamide-polyamine, which is the reaction product of diethylenetriamine and adipic acid.

G. Specific Preferred Embodiments of Absorbent Composites

In the following, specific preferred embodiments are described with reference to the drawings.

(1) Continuous Absorbent Composite Embodiments

Referring to FIG. 1, continuous absorbent composite 70 comprises a porous absorbent macrostructure layer 71, and a substrate layer 72 chemically bonded to the macrostructure layer. The substrate is bonded to the macrostructure layer through a bonding agent, preferably a cationic amino-epichlorohydrin adduct such as Kymene®. The substrate layer is cellulosic fibrous web, such as a Bounty®-type sheet. A preferred substrate is a double-ply of Bounty®-type sheet. The macrostructure layer comprises a porous absorbent macrostructure as described above.

Alternatively, continuous absorbent composite 70 shown in FIG. 1 comprises a cellulose foam layer as substrate layer 72. The cellulose foam layer is bonded to absorbent macrostructure layer 71 through a cationic amino-epichlorohydrin adduct such as Kymene®. The cellulose foam layer comprises cells of from about 100 microns to about 1000 microns. Preferably, this cellulose foam layer is compressed to further improve wicking and fluid distribution properties. The absorbent composite using such cellulose foam layer can be preferably used as an absorbent core in a catamenial product.

Referring to FIG. 2, absorbent composite 70 of yet another embodiment comprises absorbent macrostructure layer 71 formed between two substrate layers 72. One substrate layer is attached, preferably by chemical bonding using Kymene®, to each surface 75 of absorbent macrostructure layer. Each substrate layer is a double-ply of a Bounty®-type sheet.

Referring to FIG. 3, absorbent composite 70 of still another embodiment comprises two absorbent macrostructure layers 71a, 71b and two substrate layers 72a, 72b. Preferably, absorbent macrostructure layer 71a has a basis weight of about 280 g/m² (about 0.18 g/in² ), which corresponds to a layer having a thickness of between one or two particle diameters (a particle diameter being from about 150 microns to about 300 microns). Absorbent macrostructure layer 71b has a basis weight of about 560 g/m² (0.36 g/in²), which corresponds to a layer having a thickness of between three or four particle diameters of the particle.

Referring to FIG. 4, absorbent composite 70 comprises three absorbent macrostructure layers 71a, 71b, 71c and two substrate layers 72a, 72b interposed in layers 71a, 71b, and 71c alternately. Each of absorbent macrostructure layers 71a, 71b, 71c has the basis weight of about 280 g/m² (about 0.18 g/in²). Referring to FIG. 5, absorbent composite 70 comprises five substrate layers 72a–72e and four absorbent macrostructure layers 71a–71d interposed in layers 72a–72e alternately. Each of absorbent macrostructure layers 71a–71d has the basis weight of about 140 g/m² (about 0.09 g/in²).

Referring to FIG. 6, absorbent composite 70 comprises absorbent macrostructure layers 71a, 71b and substrate layer 72 interposed therebetween. Each of absorbent macrostructure layers 71a and 71b is chemically bonded to a corresponding surface 76 of substrate layer 72 using Kymene®. A preferred substrate is a compressed cellulose foam layer. The cellulose foam layer is compressed at a pressure of about 70 kgf/cm² for 15 sec. in its dry state to reduce the average pore size.

FIG. 7 shows another embodiment of a continuous absorbent composite 70 comprising a continuous absorbent macrostructure layer 71 and a substrate layer which comprises a plurality of capillary elements or strands 73 of cellulose foam having a length, bonded to the macrostructure layer 71 using Kymene®.

(2) Non-continuous Absorbent Composite Embodiments

Highly preferred absorbent composite structures of the present invention comprise non-continuous absorbent composites. Preferably, such structures are formed from continuous absorbent structures described herein. Such non-continuous absorbent structures are disclosed and claimed in co-pending, commonly-assigned U.S. patent application Ser. No. 08/142,259, filed (Oct. 27, 1993), Attorney Docket No. JA-67U.

One non-continuous absorbent composite 80, shown in FIG. 8, is an absorbent composite 80 which has an absorbent macrostructure layer 81 and a substrate layer 82, the composite 80 having a plurality of voids 85 distributed throughout the plane of the composite.

Referring to FIG. 9, a preferred embodiment of the present invention is a non-continuous absorbent composite sheet 80 which comprises an absorbent macrostructure layer 81 and a substrate 82 that is bonded to the absorbent macrostructure layer 81, wherein such absorbent composite 80 is in the form of a sheet having a plurality of voids or openings 85 therethrough. The substrate layer is a double-ply of a Bounty®-type sheet, The substrate is chemically bonded to the absorbent macrostructure layer through Kymene®. Preferably the non-continuous absorbent composite 80 has an average percent void volume of from about 17% to about 80%, more preferably from about 33% to about 67%. The voids 85 are substantially evenly distributed across the surface of the composite sheet.

Another embodiment of the present invention can be a non-continuous composite 80 having one or more area portions which have different average percent void volume.

For example, a non-continuous composite sheet has three substantially equivalent portions, wherein the first portion and the second portions each being located on opposite lateral edges of the composite sheet and having a percent void volume larger than a percent void volume of the third portion positioned therebetween.

(3) Semi-Continuous Absorbent Composite Embodiments

Other highly preferred absorbent composite structures of the present invention comprise semi-continuous absorbent composites. Preferably, such structures are formed from non-continuous absorbent structures described herein. Such semi-continuous absorbent structures are disclosed and claimed in co-pending, commonly-assigned U.S. patent application Ser. No. 08/142,259, filed (Oct. 22, 1993), Attorney Docket No. JA-67U.

A preferred embodiment of a semi-continuous absorbent composite is shown in FIG. 10 as composite 90 comprising a non-continuous porous absorbent macrostructure layer 91 and a continuous substrate layer 92. The substrate layer is a double-ply of a Bounty®-type sheet that is chemically bonded to the absorbent macrostructure layer by Kymene®. Absorbent composite 90 shown in FIG. 10 has an absorbent macrostructure layer 91 having a net-like shape. Semi-continuous absorbent composites 90 can also comprise absorbent elements or strands 91 of porous absorbent macrostructures bonded to substrate layer 92 by Kymene® as shown in FIGS. 11 and 12.

DETAILED DESCRIPTION OF METHODS FOR MAKING ABSORBENT COMPOSITES OF THE INVENTION

A. Method for Making Continuous Absorbent Composites

A method for making a continuous absorbent composite of the present invention can comprise the step of attaching, preferably bonding, at least one continuous absorbent macrostructure, preferably in the form of a sheet, to at least one substrate.

(1) Method of Making Absorbent Macrostructure Layers

Methods for making continuous absorbent macrostructure layers from substantially water-insoluble, absorbent hydrogel-forming polymer particles are disclosed in co-pending, commonly-assigned U.S. application Ser. No. 955,638, to Michael S. Kolodesh et al, entitled "Method and Apparatus for Making Cohesive Sheets from Particulate Absorbent Polymeric Composition," filed Oct. 2, 1992, the disclosure of which is incorporated by reference. Absorbent macrostructure layers made thereby can then be attached to one or more substrate, or distributing means, or support means, to form the continuous absorbent composite structures.

In a method for making an absorbent macrostructure layer of the present invention, the absorbent precursor particles are treated with an sufficient amount of the crosslinking agent to react with the polymer material at the surface of the particles so as to cause effective crosslinking, i.e., the crosslinked surface of the particle swells less in the presence of aqueous body fluids relative to the uncrosslinked portions. Preferably, the crosslinking agent is a cationic amino-epichlorohydrin adduct. Optionally, units of absorbent macrostructures made separately (e.g. one unit comprises 4–10 absorbent precursor particles), preferably by a crosslinking agent or an interconnecting means for the unit macrostructure can be mixed with the absorbent precursor particles. What constitutes "a sufficient amount" of the crosslinking agent depends upon a number of factors, including the particular absorbent precursor particles treated, the particular crosslinking agent used, the particular effects desired in forming the interparticle bonded aggregate, and like factors. In the case of monomeric amino-epichlorohydrin adducts, such as a piperazine-epichlorohydrin adducts, the amount of adduct used can be in the range of from about 0.1 to about 3 parts by weight, preferably from about 0.5 to about 1.5 parts by weight, most preferably from about 0.8 to about 1.2 parts by weight, per 100 parts by weight of the absorbent precursor particles. In the case of preferred polymeric amino-epichlorohydrin resins, such as Kymene® 557H, 557LX or Plus, the amount of resin used can be from about 0.1 to about 5 parts by weight, preferably from about 0.5 to about 2.5 parts by weight, most preferably from about 1 to about 2 parts by weight, per 100 parts by weight of the absorbent precursor particles.

Besides the absorbent precursor particles and the crosslinking agent, other components or agents can be used as aids in preparing the interparticle bonded aggregates. For example, water is typically used with the adduct to form an aqueous treatment solution thereof. Water promotes the uniform dispersion of the adduct on the surface of the precursor particles and causes permeation of the crosslinking agent into the surface regions of these particles. Water also promotes a stronger physical association between the treated precursor particles, providing greater integrity of the resultant interparticle bonded crosslinked aggregates. In the present invention, water is used in an amount of less than about 25 parts by weight (i.e. from 0 to about 25 parts by weight), preferably in the range of from about 3 to about 15 parts by weight, more preferably in the range of from about 5 to about 10 parts by weight, per 100 parts by weight of the precursor particles. The actual amount of water used can vary depending upon the type of crosslinking agent used, the type of polymer material used in forming the precursor particles, the particle size of these precursor particles, the inclusion of other optional components (e.g., glycerol) and like factors.

Organic solvents can be used, usually to promote uniform dispersion of the crosslinking agent onto the surface of the precursor particles. These organic solvents are typically hydrophilic, and can include lower alcohols such as methanol and ethanol; amides such as N,N-dimethylformamide and N,N-diethylformamide; and sulfoxides such as dimethylsulfoxide. If a hydrophilic solvent is used, it is in an amount of less than about 20 parts by weight (i.e. from 0 to about 20 parts by weight), preferably in the range of from about 5 to about 15 parts by weight, more preferably in the range of from about 8 to about 12 parts by weight, per 100 parts by weight of the precursor particles. The actual amount of hydrophilic solvent used can vary depending upon the crosslinking agent used, the polymer material used forming the precursor particles, the particle size of these precursor particles and like factors.

As previously noted, the use of hydrophilic organic solvents is not necessarily required in preparing bonded particle aggregates of the present invention. Indeed, it can be desirable to avoid the use of such organic solvents. Such solvents typically need to be removed from the aggregate before it is suitable for its intended use. The removal of organic solvents is frequently an energy and process intensive, and adds additional processing costs. Some hydrophilic solvents, such as isopropyl alcohol or t-butyl alcohol, can cause the amino-epichlorohydrin adduct to, precipitate out of solution and are therefore undesirable for this reason. Indeed, the only solvents typically used in preparing the bonded particle aggregates of the present invention are the lower alcohols such as methanol and ethanol that are not too energy or process intensive to remove, and do not cause the crosslinking agent, specifically an amino-epichlorohydrin adduct, to precipitate out of aqueous solution.

Other optional components can also be used with the crosslinking agent, and especially aqueous treatment solutions thereof. It is particularly preferred that the treatment solution comprising the crosslinking agent include a plasticizer, especially when the crosslinking agent is a cationic amino-epichlorohydrin adduct and the treated precursor particles are ambient temperature cured as described hereafter. In the absence of a plasticizer, the treated precursor particles, when formed into the interparticle bonded aggregates, can be relatively brittle, and thus more difficult to handle, especially in making the ultimately desired absorbent structures. Inclusion of a plasticizer in the treatment solution insures that the resulting interparticle bonded aggregates (when ambient temperature cured) form relatively flexible porous, absorbent macrostructures, particularly flexible, porous, absorbent sheets of the interparticle bonded aggregates. These flexible sheets are relatively easy to handle in making the ultimately desired absorbent structures.

Suitable plasticizers include glycerol or water, alone or in combination with other components such as glycerol, propylene glycol (i.e. 1,2-propanediol), 1,3-propanediol, ethylene glycol, sorbitol, sucrose, polymeric solutions such as those involving polyvinyl alcohol, ester precursors of polyvinyl alcohol, or polyethylene glycol, or mixtures thereof. These other components in the plasticizer, such as glycerol, are believed to act as humectants, coplasticizers or both, with water being the primary plasticizer. The preferred plasticizer for use in the present invention is a mixture of glycerol and water, particularly when included as part of an aqueous treatment solution of an cationic aminoepichlorohydrin adduct, in a weight ratio of glycerol to water of from about 0.5:1 to about 2:1, preferably from about 0.8:1 to about 1.7:1.

The actual amount of plasticizer used can vary depending upon the particular plasticizer used, the type of polymer material used in forming the precursor particles, the type and amount of crosslinking agent, and the particular flexibility effects desired from the plasticizer. Typically, the plasticizer is used in an amount of from about 5 to about 100 parts by weight, preferably from about 5 to about 60 parts by weight, more preferably from about 10 to about 30 parts by weight, most preferably from about 15 to about 20 parts by weight, per 100 parts by weight of the precursor particles.

The absorbent precursor particles can be treated with the crosslinking agent, and most preferably with a cationic amino-epichlorohydrin adduct, typically an aqueous solution thereof, by any of a variety of techniques. These include any method for applying solutions to materials, including coating, dumping, pouring, dropping, spraying, atomizing, condensing, or immersing the absorbent precursor particles with the cationic amino-epichlorohydrin adduct, or solution thereof. As used herein, the term "applied" means that at least a portion of the surface area of at least some of the precursor particles to be bonded together has an effective amount of the adduct on it to cause surface crosslinking. In other words, the cationic adduct can be applied onto some of the precursor particles, all of the precursor particles, a portion of the surface of some or all of the precursor particles, or the entire surface of some or all of the precursor particles. Preferably, the adduct is coated onto the entire surface of most, preferably all, of the absorbent precursor particles so as to enhance the efficiency, strength, and density of the interparticle bonds between the precursor particles, as well as the desired surface crosslinking of the polymer material in the surface of these precursor particles.

After the treatment solution has been applied onto the precursor particles, the treated precursor particles are mixed or layered together by any of a number of mixing or layering techniques to insure that the precursor particles are thoroughly coated with the treatment solution. Because the precursor particles are thoroughly coated with the treatment solution, the efficiency, strength, and density of the bonds between the precursor particles is enhanced, as well as surface crosslinking resulting from the reaction of the cationic adduct with the polymer material forming the precursor particles. This mixing can be accomplished using various techniques and apparatus, including various mixers or kneaders, as are known in the art.

After the treatment solution has been applied to the precursor particles, the treated precursor particles are physically associated together to form an aggregate macrostructure. The term "physically associated" is used herein to mean that the precursor particles are brought together and remain in contact with each other as component parts in any of a number of various ways and spatial relationships so as to form a single unit (an aggregate macrostructure).

The precursor particles are preferably physically associated together by applying an associating agent onto the precursor particles and physically contacting the precursor particles at least the portion of the surface of the precursor particles having the associating agent applied thereto. Preferred associating agents cause the polymer material of the precursor particles, when brought together, to adhere together by the action of fluid surface tension forces and/or the entanglement of polymer chains due to external swelling. Associating agents useful in the present invention include hydrophilic organic solvents, typically low molecular weight alcohols such as methanol or ethanol; water; a mixture of hydrophilic organic solvents and water; the cationic amino-epichlorohydrin adducts previously described, or mixtures thereof. Preferred associating agents are water, methanol, ethanol, crosslinking agent, most preferably a cationic polymeric amino-epichlorohydrin resins such as Kymene200 557H, or 557LX or Plus, or mixtures thereof. Typically the associating agent comprises a mixture including a cationic amino-epichlorohydrin adduct such that the step of applying the adduct is carried out simultaneously with the step of applying the associating agent.

The associating agents can be applied to the precursor particles by any of various techniques and apparatus used for applying solutions to materials including coating, dumping, pouring, spraying, atomizing, condensing, or immersing the associating agent on the precursor particles. The associating agent is applied to at least a portion of the surface of at least some of the precursor particles to be bonded together. Preferably, the associating agent is coated onto the entire surface of most, preferably all, of the precursor particles. The associating agent is generally mixed with, or sprayed onto, the precursor particles by any of a number of mixing/spraying techniques and mixing/spraying apparatus to insure that the precursor particles are thoroughly coated with the associating agent.

When an associating agent has been applied to the precursor particles, the precursor particles can be physically contacted together in a number of different ways. For example, the associating agent alone can hold the particles together in contact. Alternatively, gravitational forces can be used to insure contact between the precursor particles, e.g., by layering precursor particles. Further, the particles can be placed in a container having a fixed volume so as to insure contact between the precursor particles.

The precursor particles can alternatively be physically associated together by physically constraining the precursor particles such that they are in contact with each other. For example, the precursor particles can be packed tightly into a container having a fixed volume such that the precursor particles physically contact each other. Alternatively or in combination with the above procedure, gravitational forces (e.g., layering) can be used to physically associate the precursor particles. The precursor particles can also be physically associated together by electrostatic attraction or by the introduction of an adhering agent (e.g., an adhesive material such as a water-soluble adhesive) to adhere them together. The precursor particles can also be attached to a third member (a substrate) such that the precursor particles are brought into contact with each other by the substrate.

In an example of the method of the present invention, the aggregate macrostructure can be shaped into various geometries, spatial relationships, and densities to form an aggregate having a defined shape, size, and/or density. The aggregate can be shaped by any conventional shaping techniques as are known in the art. Preferred methods for shaping the aggregate include casting, molding, or forming operations. Casting and molding techniques generally involve introducing the precursor particles into a prepared mold cavity and applying pressure to (compressing) the aggregate to cause the aggregate to conform to the shape of the mold cavity. Examples of specific molding techniques for use herein include compression molding, injection molding, extrusion or laminating. For example, a multiplicity of precursor particles can be added to a container having a fixed volume mold cavity and the aggregate compressed to conform to the shape of the mold cavity so that the resultant macrostructure has the same shape. Forming techniques involve performing various operations on the aggregate to modify its shape, and/or size, and/or density. Examples of specific forming techniques for use herein include rolling, forging, extruding, spinning, coating or drawing operations. For example, an aggregate mixture of the precursor particles and at least the cationic amino-epichlorohydrin adduct can be passed between a pair of compaction rolls to form an aggregate sheet. Alternatively, the aggregate mixture can be extruded through an orifice to form an aggregate having a shape corresponding to that of the orifice. Further, the aggregate mixture can be cast on a surface to form an aggregate having a desired shape or surface morphology. Any or all of these techniques can also be used in combination to form the shaped aggregate. Any suitable apparatus as are known in the art can be used to carry out such operations, which can be performed with the material or portions of the apparatus either hot and/or cold.

In forming the aggregate macrostructure layers into particular shapes, and especially sheets, the density should be carefully controlled, particularly during the compaction step described above. If the density of the shape aggregate macrostructure is too high, it can be more prone to gel blocking. Conversely, if the density is too low, the absorbency of shaped aggregate macrostructure can be reduced. Shaped aggregate macrostructure layers of absorbent composites of the present invention usually have a density of from about 0.7 to about 1.3 g/cc, preferably from about 0.8 to about 1.1 g/cc, and most preferably from about 0.9 to about 1.0 g/cc.

In an example of the method of the present invention, an aggregate mixture of precursor particles, a cationic amino-epichlorohydrin adduct, water, humectant/co-plasticizer (optional), and a hydrophilic organic solvent are added to the hopper of a conventional extruder apparatus. Such an extruder apparatus is shown in FIG. 12–14 of Principles of Polymer Materials, Second Edition, (McGraw Hill Book Company, 1982) at page 331, which publication is incorporated reference. The aggregate mixture is extruded through the orifice of the extruder apparatus to feed a pair of driven compaction rolls having a fixed (but variable) gap between the rolls so as to compress the aggregate into the form of a sheet. The sheet is then processed to specific lengths to provide macrostructure layers that have a specifically designed size, shape and/or density.

(2) Continuous Method of Making Absorbent Macrostructure Layer

Figure 19:
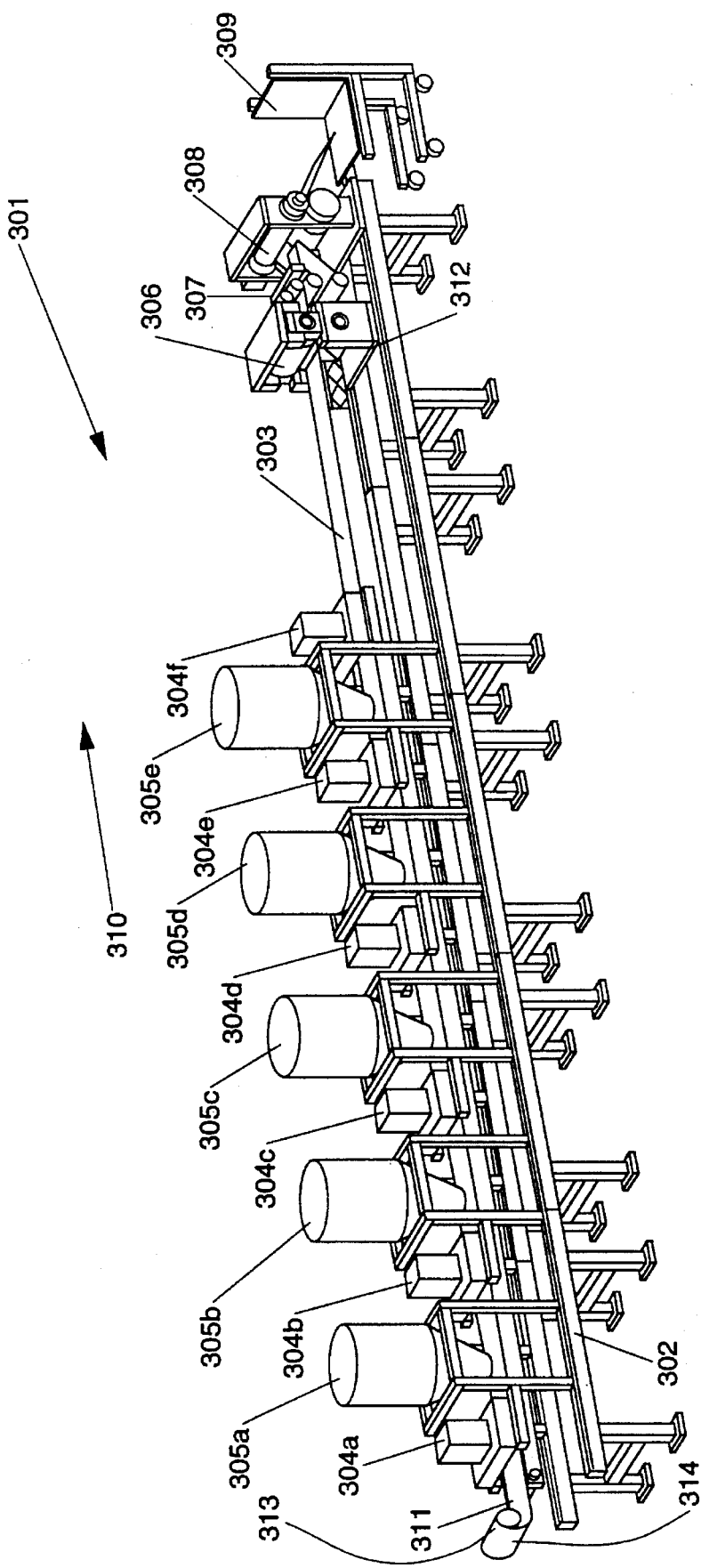
FIG. 19 is a simplified perspective view of an apparatus for making absorbent macrostructures and absorbent composites of the present invention in the form of sheets.

A preferred continuous method for making absorbent macrostructure sheets can best be understood by reference to FIG. 19 which shows apparatus 301 for carrying it out. Apparatus 301 has frame 302 for supporting its various components. Apparatus 301 comprises a support means, shown in FIG. 19 as moving conveyor 303 which moves in the direction of arrow 310. Feeders 305a through 305e supply a predetermined amount of precursor particles onto the conveyor. Optionally, the precursor particles can contain units of absorbent macrostructures made separately (e.g. one unit comprises 4–10 absorbent precursor particles), preferably by a crosslinking agent or an interconnecting means for the unit macrostructure, whereby feeders 305a through 305e can supply a mixture of the absorbent precursor particles and the units of absorbent macrostructure. Conveyor 303 first passes under an initial sprayer 304a. After passing under initial sprayer 304a, conveyor 303 passes under at least one means for continuously layering a predetermined amount of the precursor particles or the mixture onto the conveyor. This is shown in FIG. 19 as feeders 305a through 305e. Conveyor 303 also passes under at least one means for spraying a predetermined amount of treatment solution onto the layer of precursor particles on the conveyor. This is shown in FIG. 19 as sprayers 304b through 304f. Apparatus 301 further comprises a pair of non-planar opposing pressure applicators down stream from feeders 305 and sprayers 304. The pressure applicators are shown in FIG. 19 as a pair of compaction rolls 306. Also shown in FIG. 19 as being part of apparatus 301 is a slitting and transfer conveyor 307, knife and anvil rolls 308, and a sheet accumulator 309.

Conveyor 303 can be a flat belt conveyor that has good release properties, such as polyurethane, which is commonly used in the food industry. The width of the conveyor is determined by the desired sheet size. The conveyor generally moves in the direction of arrow 310 from point 311, where the initial sprayer 304a is located, to a point 312, where the knife and anvil rolls 308 are located. Conveyor 303 would typically be an endless conveyor as shown in FIG. 19.

Conveyor 303 first passes under an initial sprayer 304a, where the conveyor is sprayed with a predetermined amount of treatment solution so as to cover a predetermined area of the conveyor. This initial spraying insures that the bottom part of the first precursor particle layer is exposed to the treatment solution. Also, the wet conveyor surface will prevent the subsequently fed particles from bouncing away from their desired placement. However, the initial spraying step is not absolutely necessary, especially when the first layer of particles to be placed on the conveyor is relatively thin, or when the conveyor travels at slower speeds.

Sprayer 304a (as well as sprayers 304b through 304f) must deliver a substantially uniform mist, atomized spray and should have a low impact force to avoid possible blow off of precursor particles. One sprayer that has been found to work well is a model 6218-¼ JAU atomized air actuated nozzle assembly, available from Spraying Systems Co., Wheaton, Ill. 60188. Conveyor 303 then passes under feeder 305a where a predetermined amount of dry precursor particles is layered onto the predetermined area of the conveyor. The amount of precursor particles to be layered onto conveyor 303 depends on a number of factors including, but not limited to, the desired density of the resultant sheet, the number of layering steps to be performed, the size of the particles being used and the desired width of the resultant sheet. At a minimum the predetermined amount should be enough to substantially cover a predetermined area of the conveyor with a layer one particle in thickness.

Feeder 305a (as well as feeders 305b through 305e) must be capable of distributing the precursor particles in a thin and preferably wide layer. Thinner layers on the conveyor insure that all of the particles are treated during subsequent spraying steps and wider layers will increase production output. Vibrating feeders have been shown to be adequate for layering the dry precursor particles onto the conveyor. An example of a suitable vibrating feeder is a Super Feeder model #2106E-003S4, commercially available from Solids Flow Control, P.O. Box 410767, 14201-A South Lakes Drive, Charlotte, N.C. 28241-0767. This feeder has a weight feed-back control system for accuracy. Conveyor 303 then passes under a second sprayer 304b. A predetermined area of conveyor 303 having the first layer of precursor particles is sprayed with a predetermined amount of the same treatment solution used in initial sprayer 304a. In general, the predetermined amount of treatment solution is related to the amount of particles in the layer. The greater the amount of particles in the layer, the more treatment solution is needed to treat substantially all of the particles.

The metering and spraying steps can then be repeated a number of times (e.g., using feeders 305b through 305e and sprayers 304c through 304f) depending on the desired density of the ultimate sheet. When the metering and spraying steps are repeated a number of times and the initial spraying step is performed, as described above, the first layer of particles is exposed to two spray applications. Therefore, the initial spraying step and the first post-layering spraying step each need only spray half the amount of treatment solution needed to treat that amount of particles in the first layer on conveyor 303. The other sprayers 304c through 304f will spray the normal amount of treatment solution, i.e. twice the amount of either the initial or first post-laying spray.

After all of the layering and spraying steps have been performed, the treated precursor particles typically loosely adhere together to form a web. Conveyor 303 then moves this web and delivers it to a pair of opposing pressure applicators. The pressure applicators shown in FIG. 19 take the form of compaction rolls 306. However, as will be appreciated to those skilled in the art, an intermittent conveyor method could be used, with opposing plates or platens used to compress the web.

Compaction rolls 306 can have a non-planar, rough surface. As the web passes through compaction rolls 306, the pressure on the web causes it to expand. The rough surface of rolls 306 reduces the sliding effect between the rolls and the web in contact with the rolls. This in turn reduces expansion of the web in both the machine direction 310 and cross-machine direction. Machine direction expansion is undesirable because it requires compaction rolls 306 to speed up in order to match the machine direction expansion. Compaction by rolls 306 densities the web of freely deposited layers of precursor particles and sprayed treatment solution into a sheet.

Compaction rolls 306 can be in the form of cylindrical stainless steel rolls that are coated with a plasma coating, thereby giving the rolls a rough surface and causing them to release the web more easily after compaction. Examples of suitable coatings include coating #'s 934 and 936, available from Plasma Coatings, Inc., Waterbury, Conn. 06702. The gap between the compaction rolls determines the amount of compaction applied to the web.

Apparatus 301 can include a slitter to trim the web edges prior to compaction. The edges of the web can have a less uniform density than the rest of the web, and are typically subjected to inconsistent application of treatment solution and particles due to the conveyor belt movement in the cross-machine direction, thus making removal desirable. The slitter can be a regular circular knife working against a hard surface such as a transfer conveyor belt, as indicated by 307.

After the web passes through compaction rolls 306, a sheet is formed and collected in accumulator 309. Accumulator 309 can take the form of a wind-up roll that rolls up the sheet into a single roll of a desired size. When the desired size roll is obtained apparatus 301 can have a second slitter to cut the sheet. This second slitter can take the form of knife and anvil roll 308.

(3) Method of Making Absorbent Composites from Absorbent Macrostructure Layers

Starting with one or more continuous absorbent macrostructure layers as described above, an absorbent composite structure can be made by attaching thereto one or more substrates. Attachment of the substrate to the absorbent macrostructure layer is made by a substrate attaching means. In preferred embodiments, the substrate material comprises a cellulosic material or a material having cellulosic functionality on at least the surface. In these embodiments, the substrate attaching means preferably comprises a bonding treatment by a crosslinking agent that is capable of crosslinking the absorbent polymer molecules of the absorbent gelling particles. More preferably, the bonding treatment is by a cationic amino-epichlorohydrin adduct, more preferably Kymene®.

The layers of absorbent macrostructures and substrates can be brought together by methods well known in the art. In a preferred method, a continuous sheet layer of absorbent macrostructure is supplied, and is brought into contact and registered with a substrate layer. A predetermined amount of an attachment means, preferably in liquid form, is applied continuously to the surface of either the absorbent macrostructure layer or the substrate layer, or both, prior to registering of the layers. One or more additional substrates or absorbent macrostructure layers can be further applied to the composite. The resulting composite is preferably compacted and cured in accordance with the methods described herein. The result is a continuous sheet of an absorbent composite having a layered structure as herein described.

As previously noted, the steps in the method of the present invention for producing an absorbent macrostructure, or for forming an absorbent macrostructure layer, need not be carried out in any specific order, and can be carried out simultaneously. For example, the crosslinking agent can be applied simultaneously with the physical association of the precursor particles, shaped into a preferred shape and typically a desired density, and then the adduct reacted with the polymer material of the precursor particles, either immediately after the above steps are completed or after the aggregate has been left standing for a period of time, to simultaneously surface crosslink the precursor particles and form the aggregate macrostructure. Typically, the precursor particles are mixed or sprayed with a solution of the adduct, water, a humectant and/or coplasticizer (e.g., glycerol), and a hydrophilic organic solvent (e.g., methanol) to form an adhered together aggregate. Optionally, the absorbent precursor particles can contain units of absorbent macrostructures made separately (e.g. one unit comprises 4–10 absorbent precursor particles), preferably by a crosslinking agent or an interconnecting means for the unit macrostructure. The adduct, water, humectant/coplasticizer and hydrophilic organic solvent serve as the associating agent for the precursor particles, the adduct also serving as the crosslinking agent. The adhered aggregate (i.e. the associated precursor particles and the aqueous mixture) is subsequently shaped into a densified sheet by a combination of extruding and rolling techniques as described above. The adduct is subsequently reacted with the polymer material by ambient or heat curing to simultaneously cause crosslinking at the surface of the precursor particles and to form a cohesive interparticle bonded aggregate macrostructure.

Under certain conditions, especially if the treated precursor particles have been heat cured, the resultant macrostructures can be somewhat inflexible and potentially brittle. In such cases, the macrostructures can be made more flexible by treating it with a plasticizer. Suitable plasticizers include water, alone or in combination with the humectants/coplasticizers previously described, preferably glycerol. The plasticizer can be applied to the macrostructures in a number of different ways, including spraying, coating, atomizing, immersing, or dumping the plasticizer onto the macrostructure. Alternatively, in the case of water alone, the macrostructure can be placed in a high humidity environment (e.g., greater than 70% relative humidity). The amount of plasticizer applied to the macrostructure can be selected depending upon the specific plasticizer used, and the effects desired. Typically, the amount of plasticizer applied is from about 5 to about 100 parts by weight, preferably from about 5 to about 60 parts by weight, per 100 parts by weight of the macrostructure. A particularly preferred plasticizer comprises a mixture of glycerol and water in a weight ratio of from about 0.5:1 to about 2:1, preferably from about 0.8:1 to about 1.7:1. As shown in FIGS. 13 through 16 and especially FIGS. 15 and 16, the macrostructures resulting from the method of the present invention have pores (the dark areas of the photomicrograph) between adjacent precursor particles. The pores are small interstices between adjacent precursor particles that allow the passage of liquid into the interior of the macrostructure. The pores are formed into the macrostructure because the precursor particles do not "fit" or pack tightly enough, even when compressed, to eliminate the pores. (The packing efficiency of the precursor particles is less than 1.) The pores are generally smaller than the constituent precursor particles and provide capillaries between the precursor particles to transport liquid into the interior of the macrostructure.

Various types of fiber material can be used as the reinforcing members in the macrostructure layers of the present invention, or as co-absorbent material. Any type of fiber material which is suitable for use in conventional absorbent products is also suitable for use in the macrostructures herein, including fiber material previously described. The fiber material can be added to the macrostructure layers by introducing the fibers into treatment solution containing the crosslinking agent, by mixing with the precursor particles prior to applying the crosslinking agent, or by adding the fiber material to the crosslinking agent/precursor particle mixture. For example, the fiber material can be kneaded into the crosslinking agent/precursor particle mixture. The fiber material is preferably thoroughly mixed with the solution so that the fiber material is uniformly dispersed throughout the macrostructure. The fibers are also preferably added before reacting the crosslinking agent with the polymer material of the precursor particles.

(4) Continuous Method Of Making Absorbent Composites

A preferred continuous method for making a continuous absorbent composite comprises a step of introducing at least one substrate member into a continuous method described, herein above and illustrated in FIG. 19 for making a continuous absorbent macrostructure. In this method, a substrate comprising a first and a second surface is supplied, and a first amount of a substrate attaching means for attaching the substrate to an absorbent macrostructure layer is applied to a first area of the first surface of the substrate. Preferably, the substrate is a cellulosic material or a material that has cellulosic functionality on at least one surface thereof. The substrate attaching means preferably comprises a chemical bonding agent which can bond to both the substrate and to the absorbent gelling particles of the macrostructure layer. More preferably, the bonding agent comprises a crosslinking agent for the absorbent gelling polymer which can chemically bond to the substrate and to macrostructure layer. A highly preferred bonding agent comprises a cationic amino-epichlorohydrin adduct, more preferably Kymene®.

In the next step, a first predetermined amount of absorbent hydrogel-forming polymer particles are applied as a first layer having a thickness to the first area of the first surface of the substrate such that the particles become at least partially contacted with the amount of substrate attaching means, thereby forming a first layer of the absorbent polymer particles. Optionally, the absorbent polymer particles can contain units of absorbent macrostructures made separately (e.g. one unit comprises 4–10 absorbent polymer particles), preferably by a crosslinking agent or an interconnecting means for the unit macrostructure. In a preferred step, the particle layer is substantially uniform in thickness. When the substrate attaching means is a fluid material, the gelling particles adhere to the substrate through the substrate attaching means. When the substrate attaching means cures or becomes set, such as when an adhesive hardens or a chemical bonding agent has bonded, the gelling particles become more permanently attached to the substrate. In a preferred step wherein the substrate attaching means comprises a crosslinking agent comprising a cationic amino-epichlorohydrin adduct, the first layer of gelling particles become bonded to the substrate through the adduct upon curing of the adduct.

In a next step, a first amount of a crosslinking agent is applied to at least a portion of the surfaces of the polymer particles of the first layer. Preferably, the crosslinking agent is a liquid and is applied substantially uniformly to substantially the entire surface of the absorbent gelling particles of the first layer. Preferably the crosslinking agent comprises a cationic amino-epichlorohydrin adduct. Upon curing, the polymer material in the contacted surfaces of the particles of the first layer become crosslinked, and the portions of the surface of the gelling particles become interconnected to at least one adjacent particle, thereby forming a porous, absorbent macrostructure as herein described.

In a preferred method, additional layers of absorbent gelling particles (optionally including the units of absorbent macrostructure) are added in successive layers. Such method therefore comprises the step of applying a second predetermined amount of absorbent gelling particles to the first layer of absorbent particles, thereby forming a second layer of absorbent gelling particles. The absorbent gelling particles of the second layer become at least partially contacted with and adhere to the first particle layer through the first amount of crosslinking agent. Additional crosslinking agent is applied to the surface of the absorbent gelling particles of the second (and successive) layer substantially as described for the first layer. Upon curing, the polymer material in the contacted surfaces of the particles of the second (and successive) layer become crosslinked, and the portions of the surface of the gelling particles become interconnected to at least one adjacent particle, thereby forming a porous, absorbent macrostructure as herein described.

A method of making a continuous composite can further comprise the step of attaching or bonding at least one layer of absorbent particles onto the second surface of the substrate. Such method comprises the step of applying to a third area of the second surface of the substrate a second amount of a substrate attaching means for attaching the second surface of the substrate to an absorbent macrostructure layer. A third predetermined amount of the absorbent gelling particles (optionally including the units of absorbent macrostructure) is applied in a layer to the third area, such that the particles become at least partially contacted with the third amount of substrate attaching means, thereby forming a layer of the absorbent polymer particles on the second surface of the substrate. As described herein above, a third amount of a crosslinking means comprising a crosslinking agent is applied to at least a portion of the surfaces of the polymer particles of the third layer, which, upon curing, forms a porous, absorbent macrostructure. Additional layers of absorbent gelling particles can also be successively added to the layer of absorbent gelling particles on the second surface of the substrate.

A preferred method of making continuous composite structures comprises the further step of attaching at least a second substrate layer onto the surface of the absorbent macrostructure layer of the composite. The method comprises the step of applying to a predetermined first surface area of a second (or successive) substrate a third amount of a substrate attaching means for attaching the first surface of the second substrate to an absorbent macrostructure layer. This step can be accomplished substantially as described above for attaching absorbent particle layers to the first substrate. The first surface of the second substrate can then be registered with and attached to a surface of an absorbent macrostructure layer. The substrate attaching means, preferably in liquid form, contacts with and adheres to portions of the gelling particles at the surface of the absorbent macrostructure layer. When the substrate attaching means cures or becomes set, such as when an adhesive hardens or a chemical bonding agent has bonded, the gelling particles at the surface of the macrostructure become more permanently attached to the second substrate. In a preferred step wherein the second substrate is a cellulosic substrate, or has cellulosic functionality at least at the surface, and substrate attaching means comprises a crosslinking agent comprising a cationic amino-epichlorohydrin adduct, the absorbent macrostructure layer becomes bonded to the substrate through the adduct upon curing of the adduct. In an alternative step, the third amount of substrate attaching means can be applied to the surface of the absorbent macrostructure layer, prior to registering with and attaching the first surface of the second substrate thereto.

A method for making a continuous composite structure of the present invention can further comprise the steps of adding successive layers of absorbent particles (optionally including the units of absorbent macrostructure) and substrates, in combination with the other steps described above, to form a variety of layered absorbent composite structures as herein before described.

Preferably, in combination with any of the above steps, the resulting layered composite is compacted or pressed together to improve the contact, and interconnection, of the absorbent gelling particles with adjacent particles and with the substrate layers. A preferred method comprises the step of continuously passing the layered composite through opposing pressure means, more preferably between a pair of opposing pressure rollers, thereby continuously forming a continuous absorbent composite.

In a preferred method for making an absorbent composite of the present invention employs a continuous means of supplying a substrate layer and an absorbent macrostructure layer material, or components thereof. A preferred continuous method for making an absorbent composite can best be understood by reference to FIG. 19 which shows apparatus 301 for carrying it out. Apparatus 301 has frame 302 for supporting its various components. Apparatus 301 comprises moving conveyor 303 which moves in the direction of arrow 310. Feeders 305a through 305e supply a predetermined amount of precursor particles onto the conveyor. Optionally, the precursor particles can contain units of absorbent macrostructures made separately e.g. one unit comprises 4–10 absorbent precursor particles), preferably by a crosslinking agent or an interconnecting means for the unit macrostructure, whereby feeders 305a through 305e can supply a mixture of the absorbent precursor particles and the units of absorbent macrostructure. Apparatus 301 further comprises sheet feeder 313 for supplying a substrate 314. Sheet feeder 313 includes a wind-up roll that rolls up the substrate 314 having a desired size. The width of the Bounty sheet 314 is smaller than that of moving conveyor 303. In operation, sheet feeder 313 feeds the rolled substrate 314 to moving conveyor 303. The Bounty sheet 314 on conveyor 303 first passes under an initial sprayer 304a, where the substrate is sprayed with a predetermined amount of treatment solution so as to cover a predetermined area of the substrate. After passing under initial sprayer 304a, conveyor 303 passes under at least one means for continuously layering a predetermined amount of precursor particles onto the substrate 314. This is shown in FIG. 19 as feeders 305a through 305e. Conveyor 303 also passes under at least one additional means for spraying a predetermined amount of treatment solution onto the layer of precursor particles on the substrate 314. This is shown in FIG. 19 as sprayers 304b through 304f. Apparatus 301 further comprises a pair of non-planar opposing pressure applicators down stream from feeders 305 and sprayers 304. The pressure applicators are shown in FIG. 19 as a pair of compaction rolls 306. Also shown in FIG. 19 as being part of apparatus 301 is a slitting and transfer conveyor 307, knife and anvil rolls 308, and a sheet accumulator 309.

Conveyor 303 can be a flat belt conveyor that has good release properties, such as polyurethane, which is commonly used in the food industry. The width of the conveyor is determined by the desired composite size. The conveyor generally moves in the direction of arrow 310 from point 311, where the initial sprayer 304a is located, to a point 312, where the knife and anvil rolls 308 are located. Conveyor 303 would typically be an endless conveyor as shown in FIG. 19.

Conveyor 303 first passes under an initial sprayer 304a, where the substrate is sprayed with a predetermined amount of treatment solution so as to cover a predetermined area of the substrate. This initial spraying insures that the bottom part of a first precursor particle layer is exposed to the treatment solution. Sprayer 304a (as well as sprayers 304b through 304f) must deliver a substantially uniform mist, atomized spray and should have a low impact force to avoid possible blow off of precursor particles. One sprayer that has been found to work well is a model 6218-¼ JAU atomized air actuated nozzle assembly, available from Spraying Systems Co., Wheaton, Ill. 60188. Conveyor 303 then passes under feeder 305a where a predetermined amount of dry precursor particles is layered onto the predetermined area of the substrate 314. The amount of precursor particles to be layered depends on a number of factors including, but not limited to, the desired density of the resultant sheet, the number of layering steps to be performed and the size of the particles being used. At a minimum the predetermined amount should be enough to substantially cover a predetermined area of the substrate with a layer one particle in thickness.

Feeder 305a (as well as feeders 305b through 305e) must be capable of distributing the precursor particles in a thin and preferably wide layer. Thinner layers on the substrate 314 insure that all of the particles are treated during subsequent spraying steps and wider layers will increase production output. Vibrating feeders have been shown to be adequate for layering the dry precursor particles onto the substrate 314. An example of a suitable vibrating feeder is a Super Feeder model #2106E-003S4, commercially available from Solids Flow Control, P.O. Box 410767, 14201-A South Lakes Drive, Charlotte, N.C. 28241-0767. This feeder has a weight feed-back control system for accuracy.

Conveyor 303 then passes under a second sprayer 304b. A predetermined area of substrate 314 having the first layer of precursor particles is sprayed with a predetermined amount of the same treatment solution used in initial sprayer 304a. In general, the predetermined amount of treatment solution is related to the amount of particles in the layer. The greater the amount of particles in the layer, the more treatment solution is needed to treat substantially all of the particles.

The metering and spraying steps can then be repeated a number of times (e.g., using feeders 305b through 305e and sprayers 304c through 304f) depending on the desired density of the absorbent macrostructure layer. When the metering and spraying steps are repeated a number of times and the initial spraying step is performed, as described above, the first layer of particles is exposed to two spray applications. Therefore, the initial spraying step and the first post-layering spraying step each need only spray half the amount of treatment solution needed to treat that amount of particles in the first layer on substrate. The other sprayers 304c through 304f will spray the normal amount of treatment solution, i.e. twice the amount of either the initial or first post-laying spray.

After all of the layering and spraying steps have been performed, the treated, precursor particles typically loosely adhere together to form an absorbent macrostructure layer on the substrate 314. Conveyor 303 then moves this composite and delivers it to a pair of opposing pressure applicators. The pressure applicators shown in FIG. 19 take the form of compaction rolls 306. However, as will be appreciated to those skilled in the art, an intermittent conveyor method could be used, with opposing plates or platens used to compress the composite.

Compaction rolls 306 can have a non-planar, rough surface. As the composite passes through compaction rolls 306, the pressure on the composite causes it to expand. The rough surface of rolls 306 reduces the sliding effect between the rolls and the composite in contact with the rolls. This in turn reduces expansion of the composite in both the machine direction 310 and cross-machine direction. Machine direction expansion is undesirable because it requires compaction rolls 306 to speed up in order to match the machine direction expansion. Compaction by rolls 306 densifies the sprayed treatment solution into the freely deposited layers of precursor particles.

Compaction rolls 306 can be in the form of cylindrical stainless steel rolls that are coated with a plasma coating, thereby giving the rolls a rough surface and causing them to release the composite more easily after compaction. Examples of suitable coatings include coating #'s 934 and 936, available from Plasma Coatings, Inc., Waterbury, Conn. 06702. The gap between the compaction rolls determines the amount of compaction applied to the composite.

Apparatus 301 can include a slitter to trim the web edges prior to compaction. The edges of the composite can have a less uniform density than the rest of the composite, and are typically subjected to inconsistent application of treatment solution and particles due to the conveyor belt movement in the cross-machine direction, thus making removal desirable. The slitter can be a regular circular knife working against a hard surface such as a transfer conveyor belt, as indicated by 307.

After the web passes through compaction rolls 306, a continuous composite sheet is formed and collected in accumulator 309. Accumulator 309 can take the form of a wind-up roll that rolls up the sheet into a single roll of a desired size. When the desired size roll is obtained apparatus 301 can have a second sillier to cut the sheet. This second slitter can take the form of knife and anvil roll 308.

in the case where macrostructure layers are formed on both main surfaces of the substrate 314, a variety of methods can be employed. In one method, the same or similar process as the described above is carried out on the second main surface of the substrate 314. More specifically, a continuous composite sheet comprising an absorbent macrostructure layer and a substrate is stored on sheet feeder 314. Sheet feeder 314 supplies the continuous composite sheet to the same, or a second, conveyor 303, this time with the absorbent macrostructure layer of the composite contacting the conveyer 303. Sprayer 304a through 304f and feeder 305a through 305e operate as described above on the second main surface of the substrate 314, thereby forming a continuous composite sheet having macrostructure layers formed on each of the main surfaces of the substrate 314, e.g. as shown in FIG. 6.

In another method not shown in the Figures, a intermediate composite is processed as described above by applying one or more absorbent particle layers to a first surface of a substrate. The intermediate composite is then inverted so that the layers of absorbent particles on the intermediate composite are facing toward the conveyor 303. The intermediate composite then passes as before under one or more sprayer 304 and absorbent gelling particles addition means 305 to add one or more additional layers of the gelling particles to the second main surface of the substrate. The composite can then be compacted, etc. as previously described.

Alternately, a first continuous absorbent macrostructure layer can be made by applying one or more layers of absorbent gelling particles, followed by treatment solution, directly to the belt 303, then a substrate layer can be introduced intermediate the conveying line 301 to register and attach the first main surface of the substrate to the first continuous absorbent macrostructure layer. Subsequently, a second continuous absorbent macrostructure layer can be applied to the second main surface of the substrate by applying one or more layers of absorbent particles and treatment solution thereto.

Further, a composite can comprise a second substrate layer. A predetermined area on the macrostructure layer, or a layer of gelling particles applied from a feeder means 305, is sprayed with a predetermined amount of the same treatment solution used in initial sprayer 304a. A second substrate sheet can be brought into contact with the sprayed macrostructure layer. As a result, a bonding between the second substrate sheet and the sprayed macrostructure layer can be made through crosslinking, whereby an absorbent composite having the structure as shown in FIG. 2 can be obtained. Alternatively, a predetermined area of a second substrate sheet can be sprayed with a predetermined amount of the same treatment solution, and then applied to the surface of an absorbent macrostructure.

Selectively repeating the above described steps about any continuous absorbent composites, non-continuous absorbent composites having layered structures shown in FIGS. 3, 4 and 5 can be obtained.

Simultaneously or after the crosslinking agent has been applied, the precursor particles have been physically associated together to form an aggregate, and the aggregate has been shaped, the crosslinking agent is reacted with the polymer material of the precursor particles, while maintaining the physical association of the precursor particles, to provide effective surface crosslinking in the precursor particles in the aggregate macrostructure. The preferred crosslinking agent is cationic amino-epichlorohydrin adduct. Because of the relatively reactive cationic functional groups of the amino-epichlorohydrin adduct, the crosslinking reaction between the adduct and the polymer material of the precursor particles can occur at relatively low temperatures. Indeed, this crosslinking reaction (curing) can occur at ambient room temperatures. Such ambient temperature curing is particularly desirable when the treatment solution comprising the adduct additionally contains a plasticizer, such as a mixture of water and glycerol. Curing at significantly above ambient temperatures can cause the plasticizer to be driven off due to its volatility, thus necessitating an additional step to plasticize the resulting interparticle bonded aggregate. Such ambient curing is typically carried out at a temperature of from about 18° C. to about 35° C. for from about 12 to about 48 hours. Preferably, such ambient curing is carried out at a temperature of from about 18° C. to about 25° C. for from about 24 to about 48 hours.

Although the crosslinking reaction between a cationic amino-epichlorohydrin adduct and the polymer material of the precursor particles can occur at ambient temperatures, such curing can also be carried out at higher temperatures to speed up the reaction. Higher temperature curing typically involves heating the composite comprising the treated and associated precursor particles to cause the crosslinking reaction between the adduct and the polymer material of the precursor particles to occur in a shorter period of time, typically minutes. This heating step can be carried out using a number of conventional heating devices, including various ovens or dryers well known in the art.

Generally, heat curing can be carried out at a temperature above about 50° C. for a period of time sufficient to complete the crosslinking reaction between the adduct and the polymer material of the precursor particles. The particular temperatures and times used in heat curing will depend upon the particular cationic amino-epichlorohydrin adduct used and the polymer material present in the precursor particles. If the cure temperature is too low, or the cure time too short, the reaction will not be sufficiently driven, resulting in macrostructures that have insufficient integrity and poor absorbency. If the cure temperature is too high, the structural integrity of the substrate means can be diminished. This can leave the absorbent composite with little additional dry or wet strength support from the substrate.

The crosslinking reaction between the cationic amino-epichlorohydrin adduct and the polymer material of the precursor particles is sufficiently fast, even at ambient temperatures, such that it can be carried out in the absence of initiators and/or catalysts. However, an important factor relative to the reactivity of the amino-epichlorohydrin adduct is the pH of the treatment solution containing the adduct. Typically, the pH of the treatment solution is from about 4 to about 9, preferably from about 4 to about 6. Maintenance of the treatment solution at a pH within these ranges insures that the aminoepichlorohydrin adduct will be sufficiently reactive, even at ambient temperatures.

The physical association of the treated precursor particles needs to be maintained during the curing step so that, as crosslinking occurs, adjacent precursor particles become cohesively bonded together, if forces or stresses are sufficient to disassociate the precursor particles that are present during the crosslinking reaction, insufficient bonding of the precursor particles can occur. This can result in aggregates having poor structural integrity. The physical association of the precursor particles is typically maintained by insuring minimal dissociation forces or stresses are introduced during the curing step.

B. Method for Making Non-Continuous Absorbent Composites

Figure 18:
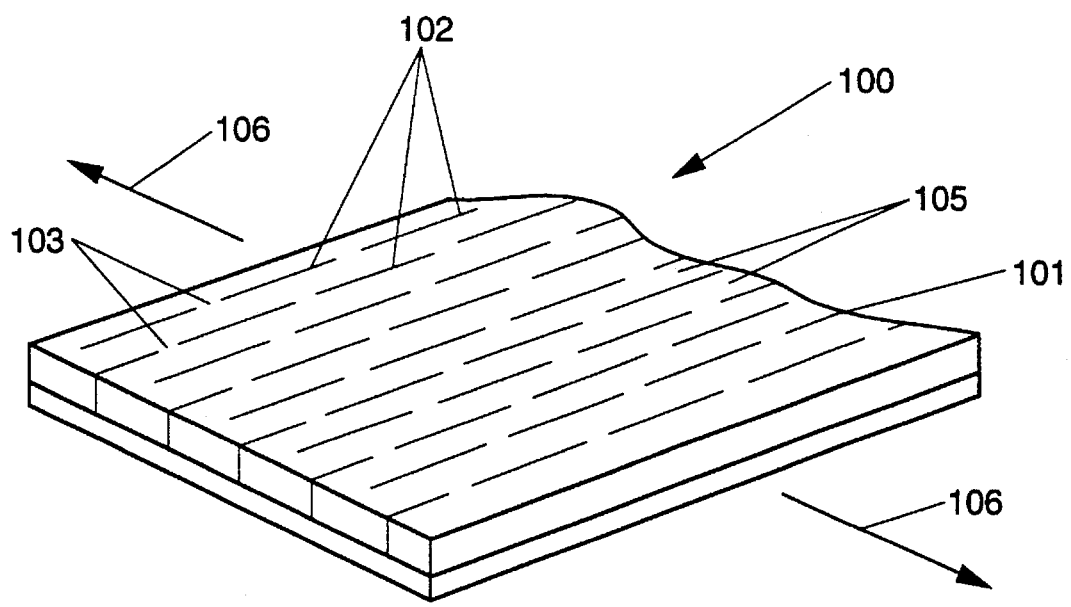
FIG. 18 is a perspective view of a slitted absorbent composite for use in a method of making a non-continuous absorbent composite having a net-like shape according to the present invention.

A preferred method for making a non-continuous absorbent composite comprises a first step of forming a plurality of slits or cuts penetrating at least partially, preferably completely, through the thickness of the continuous composite sheet. Preferably, at least a substantial portion of, more preferably all of, said cuts are oriented in substantially the same direction in accordance with a predetermined pattern. An example of a continuous composite in which a predetermined pattern of cuts been made in a continuous, interlaced pattern is shown in FIG. 18. Voids are formed in the composite at the location of the slits when the slitted composite is then stretched in a direction substantially perpendicular to the direction of the slits, thereby forming the non-continuous composite. In general, the degree of stretching of a slitted composite results in a larger void opening at the site of the slit, and a larger percentage of void volume in the resulting non-continuous composite.

A preferred method for making a non-continuous absorbent composite comprises a step of forming a slitted continuous absorbent composite 100 as shown in FIG. 18. The step comprises forming intermittently, along each of a plurality of substantially parallel lines 101, a plurality of slits 102 completely through the thickness of the composite. The distance 103 along a line between successive cuts 102 can be uniform, random, or ordered. Increasing the distance 103 between successive cuts in parallel lines decreases the percent void volume of the non-continuous composite (after stretching) in that portion of the composite. Similarly, the spacing distance 105 between successive parallel lines of slits can be uniformly the same, random, or ordered. Increasing the spacing distance 105 between successive parallel lines of slits decreases the percent void volume of the non-continuous composite (after stretching) in the portion along the length of such parallel lines.

In a preferred method, the slitted continuous absorbent composite 100 is stretched in the width direction 106 by from about 20% to about 400% of the width of the composite 100, whereby the average percent void volume of from about 17% to about 80% can be obtained. More preferably, the slitted continuous absorbent composite 100 is stretched in the width direction 106 by from about 50% to about 300% of the width of the composite 100, whereby the average percent void volume of from about 33% to about 67% can be obtained.

A preferred method comprises making a non-continuous composites having a first width area having a percent void area that is greater than that of a second width area. In the first width area of this continuous composite, a series of substantially parallel lines of intermittent cuts having a predetermined spacing 105 between adjacent lines is formed. In a second width area adjacent to the first area, a second series of substantially parallel lines of intermittent cuts having a wider predetermined spacing 105 between adjacent lines is made, such that when the slitted composite 100 comprising both slitted areas is stretched uniformly, the distance between adjacent voids formed by the slits in the first width area of the composite is smaller than the distance between adjacent voids in the second area, and wherein the percentage of void space in the first area of the non-continuous composite is greater than the percent void space in the second area.

In another preferred method, the spacing distance 105 between a series of successive lines in a first width area has the same spacing distance 105 between a series of successive lines in a second width area. However, the distance or amount of stretching in the first width area is made greater than the distance or amount of stretching in the second area. In the resulting non-continuous composite, the distance between voids formed from the slits of the first width area of the composite is the same as the distance between voids of the second width area. However, the area (width) of a void opening formed in the first width area is greater than the area (width) of a void opening in the second width area, and subsequently the percent void space in the first width area of the non-continuous composite is greater than the percent void space in the second area.

Another preferred method involves making a non-continuous composites having a first length area having a percent void area that is greater than that of a second length area. A series of substantially parallel lines of intermittent cuts are made in a continuous composite. In a first length area, successive intermittent cuts have a predetermined cut length 102 and a predetermined spacing between successive cuts 103. In a second length area, successive intermittent cuts have a shorter cut length 102, but the same spacing 103 between successive cuts, compared to the first length area. This slitted composite is then stretched uniformly along both lengths. In the resulting non-continuous composite, the distance between adjacent voids formed from the slits of the first length area of the composite is substantially the same as the distance between adjacent voids of the second length. However, the area (length) of a void opening formed in the first length area is greater than the area (length) of a void opening in the second length area, and subsequently the percent void space in the first length area of the non-continuous composite is greater than the percent void space in the second length area of the non-continuous composite.

In alternative methods, the lengths of cuts and spacing distance between cuts of successive parallel lines of intermittent cuts can be varied to provide, upon stretching of the slitted composite, non-continuous composites having voids of various shapes and sizes (areas), different spacing between voids, and having different percent void areas. The lengths of slits, the spacing distance between successive slits in a line, and the spacing between successive lines of slits can be varied to provide non-continuous composites comprising areas having voids of various shapes and sizes (areas), and having different percent void space in an area. The spaces and lengths can be selected to provide different absorbency and percentage void volume for a particular absorbency requirement, or for a particular absorbent product. The length of the slit lines, the spacing between successive slits, and the spacing between successive parallel lines of slits can each also affect the flexibility and extensity (how far the slitted sheet can be stretched). Of course, the thickness and density of the absorbent macrostructure, the type of crosslinking agent used, the presence of plasticizer in the macrostructure, the type of substrate material, and various other factors can also effect the flexibility of the slitted and stretched structure. However, for a given absorbent composite structure, in general, the flexibility of a structure, and the extensity of a slitted composite are inversely proportional to the spacing between successive parallel lines of slits.

The pattern of slits in the slitted composite can be made substantially uniform, randomly, or ordered. Typically, the length of slits is from about 2 mm to about 50 mm, preferably from about 5 mm to about 25 mm, more preferably about 10 mm to about 20 mm. Typically the spacing distance between successive slits on a line is from about 1 mm to about 20 mm, preferably from about 2 mm to about 10 mm, more preferably from about 3 mm to about 5 mm. Typically, the spacing between successive parallel lines of slits is from about 1 mm to about 10 mm, preferably from about 1.5 mm to about 5 mm, more preferably about 2 mm to about 3 mm.

Figure 18A:
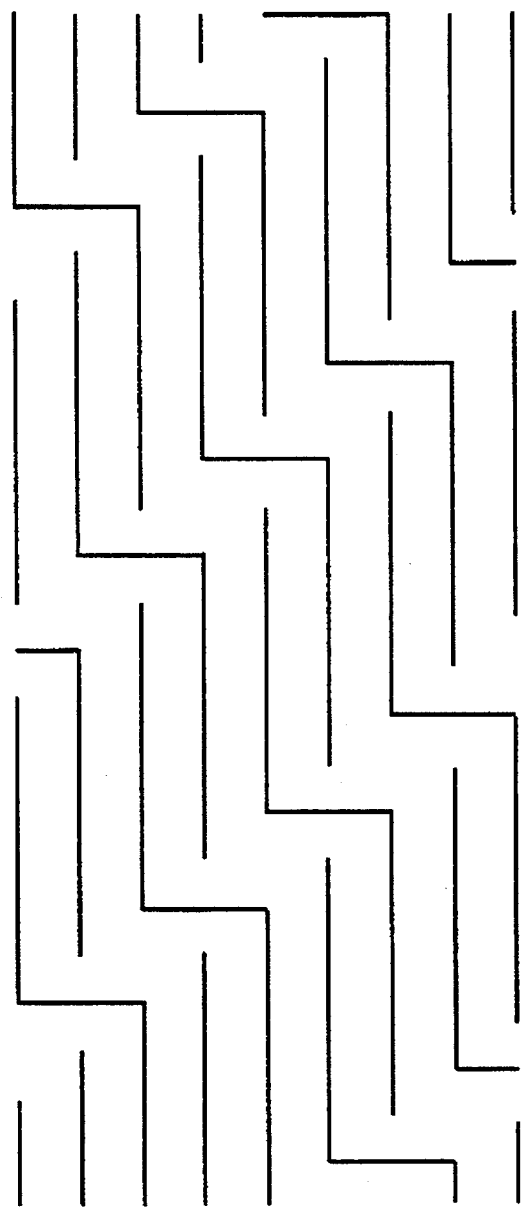
FIG. 18A shows a portion of a pattern of lines which can be used alternatively as a pattern of slits in a method of making a non-continuous absorbent composite of the present invention.

Another non-limiting example of slitting patterns which can be used is shown in FIG. 18A.

A preferred method of forming a slitted absorbent macrostructure, that can then be stretched to form voids at the location of the slits, involves continuously forming slits in a predetermined pattern. This preferred continuous method for making an absorbent composite can best be understood by reference to FIG. 20 which shows apparatus 401 for cutting machine-direction slits into a continuous composite. Apparatus 401 comprises a continuous slit forming device 420. An unwinding roll 402 supplies a continuous sheet 405 of continuous absorbent composite to the slit forming device 420, and a wind-up roll 415 collects a continuous sheet 412 of a slitted, partially stretched composite. The continuous slit forming device 420 comprises a knife roll 422 with a plurality of knife blades 432, and a recess roll 424 having a plurality of recess grooves 441 in the surface thereof. The continuous sheet is passed through the opening 421 between the knife roll 422 and the recess roll 424. The knife roll 422 and the recess roll 424 are rotated in opposite directions about their respective axes 423 and 426. Both the knife roll and the recess roll are each adjustable in their relative vertical and horizontal pitch and axial alignment. The absorbent composite is essentially pulled through the slit forming device 420 by the rotation of the knife blades. Preferably, a drive mechanism having sufficient power and timing capability (well known in the art) is used to synchronize the rotation of the two axes at relatively the same rotational speed, regardless of loading by the action of slitting of the composite.

Figure 20:
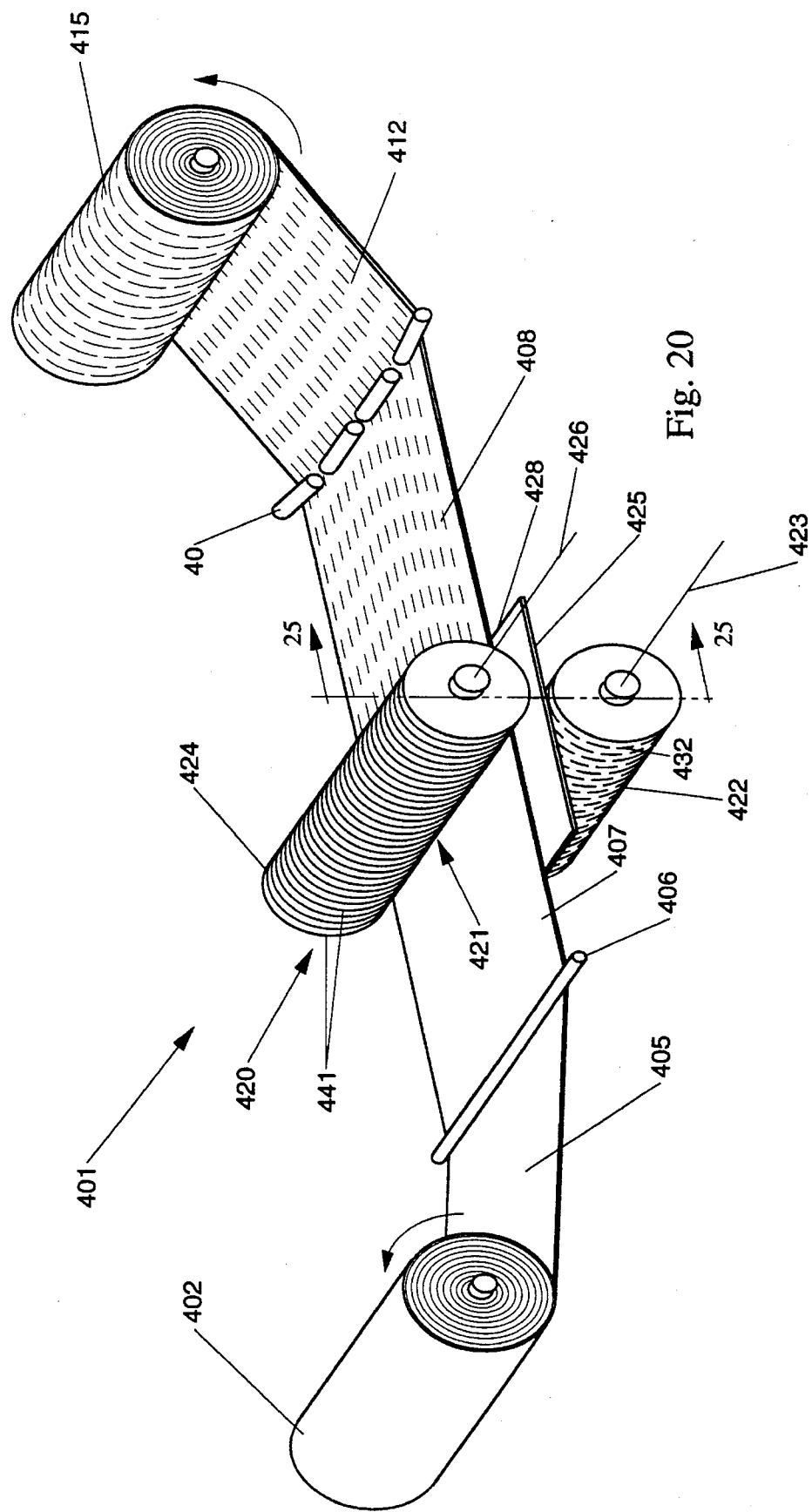
FIG. 20 is a simplified perspective view of an apparatus for forming a continuous slitted absorbent composite of the present invention.
Figure 21:
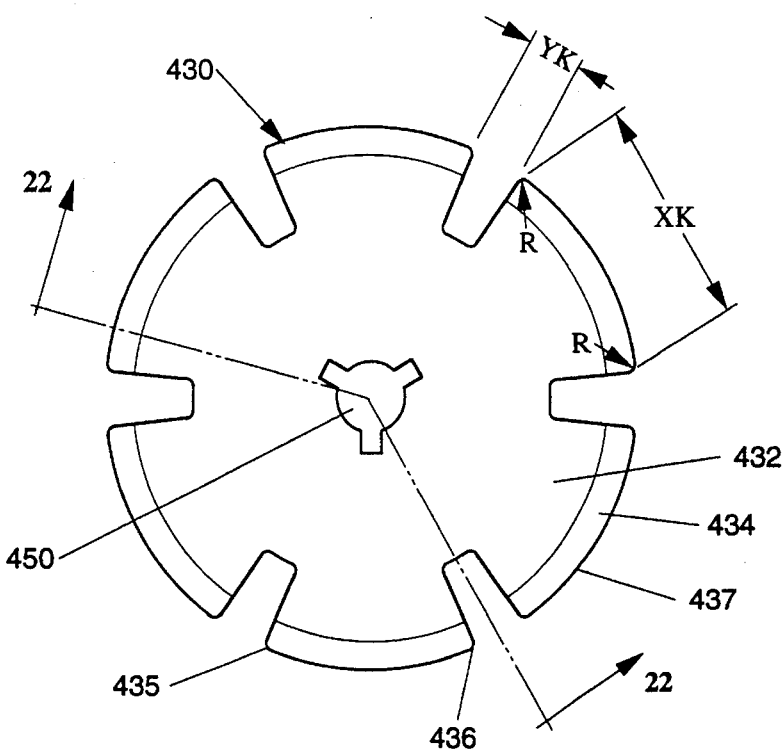
FIG. 21 is a plan view of a blade plate for forming slits in an absorbent composite.

In a preferred embodiment, the knife roll comprises a plurality of knife plates 430 as shown in FIG. 21. The plurality of knife plates are mounted on a drive shaft 423 (shown in FIG. 20) through shaft opening 450 at the centerline of the blade. The individual knife blades 432 are constructed and arranged on the blade plate to maintain a rotational center of gravity at the centerline of the blade. A knife plate 430 comprises a plurality of knife blades 432. Each knife blade comprises a cutting portion 434 having a cutting tip 437, a leading edge 435 and a trailing edge 436. The cutting portion of the blade is that portion which can pass into the structure of the composite sheet 407 during the slitting process. The length of a knife blade, defined by $x_k$, is the maximum length of the cutting portion 437 of the blade, from the leading edge 435 to the trailing edge 436. The leading and trailing edges 435 and 436 preferably are slightly rounded (radius about 0.5 mm) in order to improve the separation of the trailing edge of the blade from the slitted composite by eliminating any corner on the blade which might catch the trailing edge of the slit.

Preferred knife blades of the present invention can be made of any material which has a material hardness sufficient to cut the absorbent composite and sufficient strength to prevent bending, warping, flexing, or vibrating during the slitting operation. Preferably, an extremely hard metallic or other material is used for longer wear and excellence in cutting performance. A preferred material is tungsten.

Figure 22:
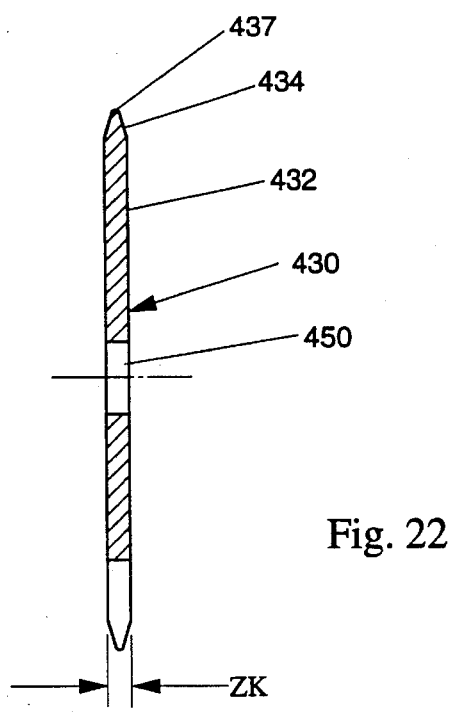
FIG. 22 is a cross-sectional view of the blade plate of FIG. 21 through line 22—22.

The thickness of the cutting portion of the blade, shown as $z_k$ in FIG. 22 is preferably kept as thin a possible to reduce the resistance through the composite. The blade should be of sufficient thickness to provide strength to prevent bending, warping, flexing, or vibration during the slitting operation. Preferably, the thickness of the cutting portion is less than about 1 mm, more preferably less than about 0.5 mm.

The spacing between successive blades is shown as $y_k$. Although the knife blade shown in FIG. 21 has six equally sized and spaced blades, knife plates can be used having a substantially greater number of blades, and therefore a greater diameter and circumference. The spacing distance between adjacent knife plates can be adjusted by placing one of more spacers 439 (FIG. 25), or shims, on the axis of the knife roll between adjacent knife blades to provide the appropriate spacing.

In a preferred embodiment, the continuous composite sheet 407 (FIG. 20) is partially tensioned in the cross-machine direction as the sheet enters the knife roll. The tensioning assists the cutting of the composite layers by the blades. In addition, the tensioning helps to reduce the friction of the cutting blades as they rotate out of the slits, due to the slightly shrinkage of the width of the composite segments between adjacent blades as the tension is released upon slitting.

Figure 25:
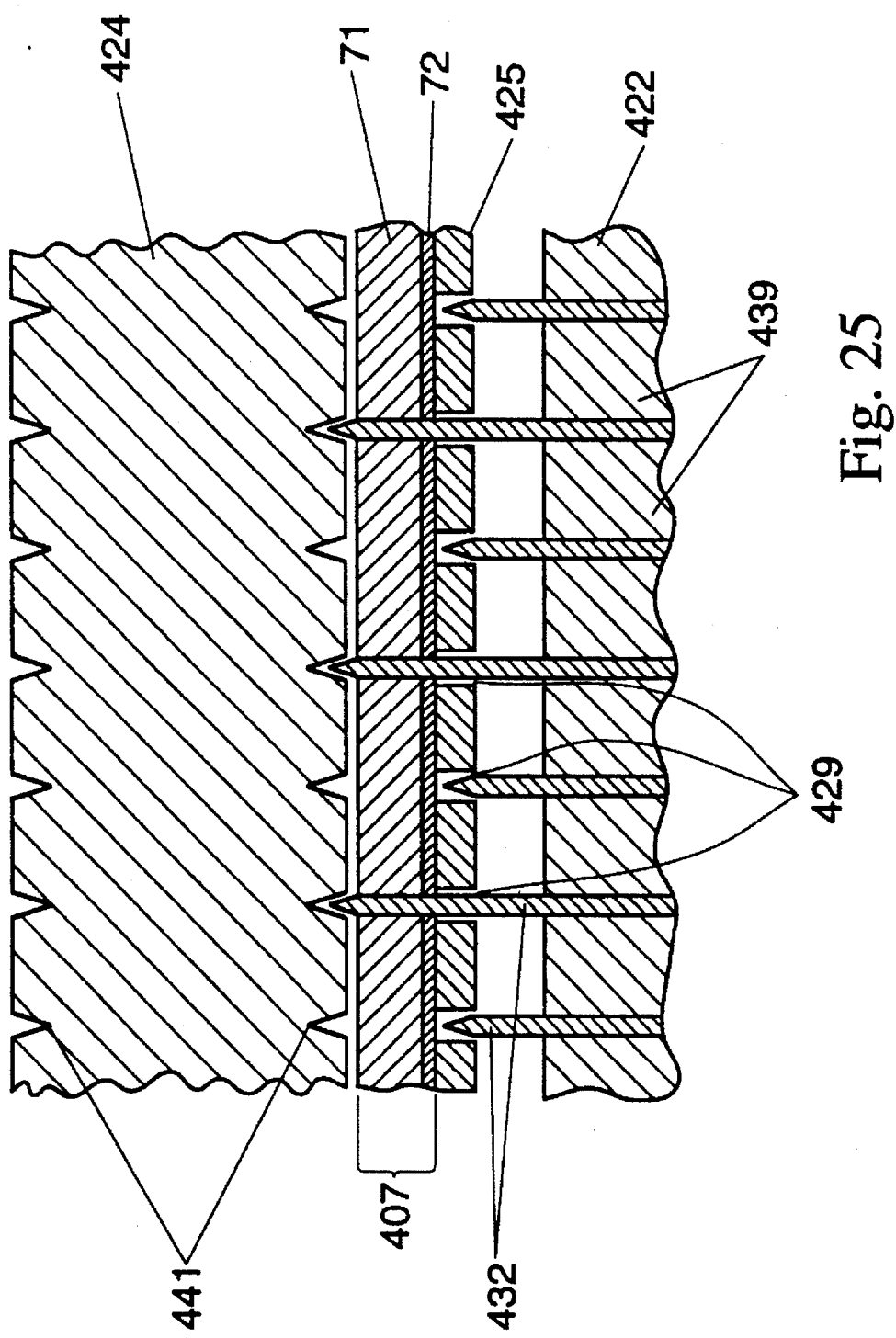
FIG. 25 is a partial cross-sectional view of the slit forming device 420 shown in FIG. 20 through line 25—25.

In a preferred embodiment of the method and apparatus, a means for disengaging the slitting blades 432 from the slits of the slitted sheet 408 is provided. A preferred disengaging means is a stripping plate 425 shown in FIG. 25. The stripping plate 425 comprises a plurality of parallel slots 429 extending there through. The length and width of each slot, and the spacing between slots, accommodates the plurality of knife blades of the knife roll 422. The blades 432 of the knife roll are positioned to extend from the upper surface through the stripping plate slots 429 as shown in FIG. 25. The continuous composite sheet 407 is position on the lower surface of the stripping plate 425. The stripping plate 425 has a trailing edge 428 which supports the slitted composite sheet as it separates from the knife roll 422. The stripping 425 plate is usually constructed from a metallic material, preferably stainless steel, and is of sufficient thickness to resist bending by the force of the slitted composite sheet when it is separated from the knife roll.

To assist in the stripping or separating of the slitted composite from the knife blades, a stripping layer material can be used. Such layer can be a layer integral with the absorbent composite, for example a nonwoven layer on the surface of the absorbent composite facing toward the knife roll. The stripping layer can also be an independent layer that is registered with the continuous composite prior to the slit forming step, and is separated from the slitted composite thereafter. An example of such material can include nonwovens, plastic or metallic films, and waxed or other treated substrates or paper. The stripping layer can also have a lubricating agent which can deposit on the blades to help resist buildup of absorbent macrostructure and substrate material. Such lubricants can be liquid or semi-solid, such as a wax or oil, or solid agent such as graphite. A preferred stripping layer is waxed paper.

Figure 23:
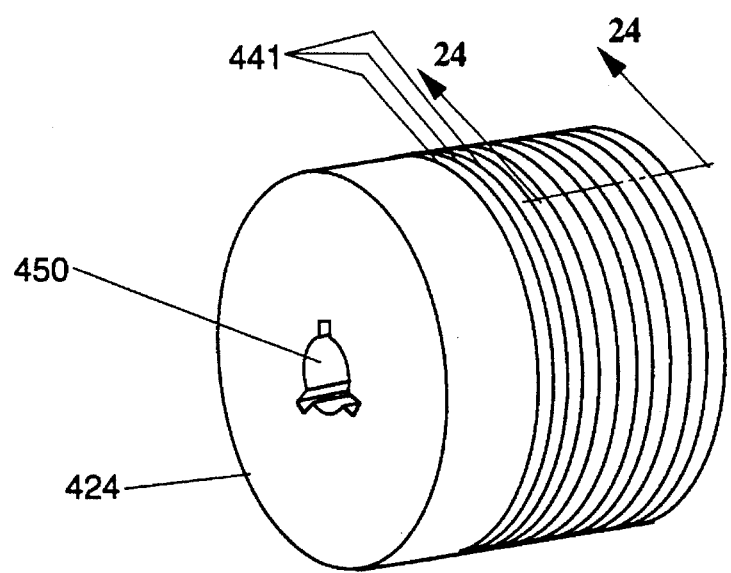
FIG. 23 is a simplified perspective view of a recess roll used in a method for forming slits in an absorbent composite.
Figure 24:
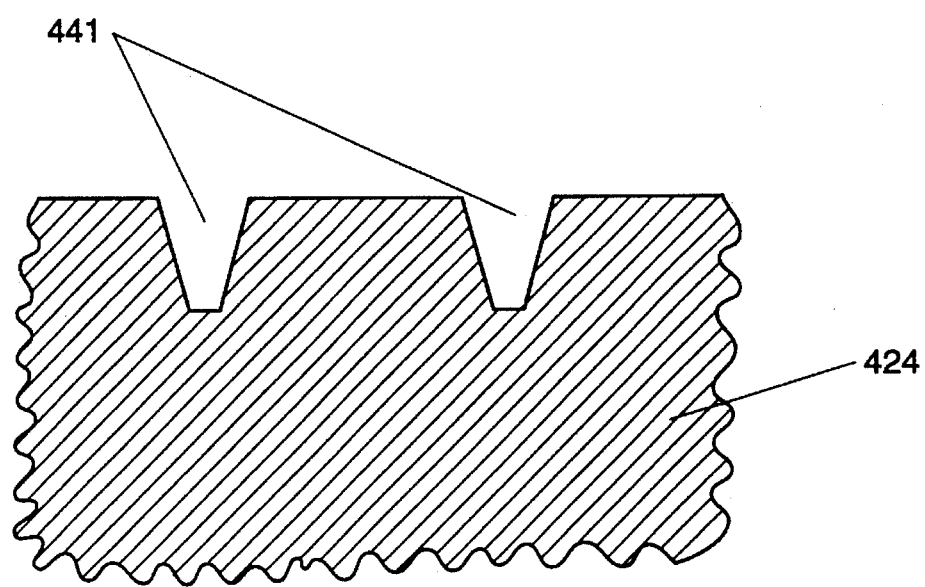
FIG. 24 is a partial cross-sectional view of the recess roll of FIG. 23 through line 24—24.

The recess roll 424 has a series of grooves 441 as shown in FIG. 23 which serve as guides for the blades 432 of the blade roll. The recess roll also serves to retain the absorbent composite sheet against the blade roll (and optionally, the stripping plate 425). There is essentially one groove for each blade plate. Groove 441 preferably has a shape and dimension to match the cutting tip 434 of the blades as closely as possible. Most preferably, the recess roll is constructed of a material that is as hard as possible, but will not cut or wear out the blade cutting tips 434. A preferred material for constructing the recess roll is nylon or Teflon. The grooves can be formed initially in the recess roll by touching or slightly pressing the rotating blade roll against the recess roll to set the track of the blades.

Other devices can used in place of a recess roll to provide the same function. For example, a stationary backing member having a series of slots can also be used. An example of a stationary backing member is a slotted plate which resembles the stripping plate 425. The composite sheet 407 passes between the stripping plate 425 and the stationary backing member. The blades of the blade roll rotate through the slots of the stripping plate and the stationary backing member, thereby cutting the slits in the sheet.

Individual recess plates corresponding in spacing and number to the blade plates can also be used in place of a recess roll.

It is also preferred to provides means for continuously cleaning the knife blades and the recess roll of substrate material and absorbent macrostructure material that can build up. Such means can include brushes, high pressure air streams, and other similar means well known in the art.

In the absorbent composites of the present invention, the substrate layer 72 can comprise a material that is difficult to cut cleanly through, especially when the substrate is partially wet with liquid (from the composite making process). When wet, the substrate can stretch when impinged by the blade. In a preferred process of the present invention, the absorbent composite sheet 407 is passed through the slit forming device so that a substrate layer in the composite is oriented toward the knife roll 422. This assists the knife blade to make a complete slit through the substrate material. Furthermore, orienting the substrate toward the knife roll permits the substrate layer itself to assist in the separating of the absorbent composite, particularly the absorbent macrostructure layer, from the knife blades after the slits have been formed.

After a slitted absorbent composite is made, it can be collected and stored until needed. Typically it will be collected on a wind-up roll 415 for transportation or storage.

The process of slitting the continuous sheet 407 itself can cause the width dimension of the slitted composite 408 to be increased. In preferred embodiments, where the spacing between parallel lines of slits in the composite is very close, (for example, from 1 mm to 5 mm), the width dimension of the slitted sheet 408 can be from 5% to 10% greater, or more, than the width dimension of the starting non-slitted composite sheet 407.

Because of the crosslinking and bonding caused by the crosslinking agent, it is preferred that the slitted absorbent sheet be partially stretched before the wind-up roll. The amount of partial stretching will depend upon the properties of the absorbent composite (such as thickness, etc.) and the slit pattern (such as, slit length). Usually, the slitted sheet is partially stretched between 1% and about 50% across the width of the slits (i.e., stretched in the cross-machine direction for slits that are oriented in the machine direction) before the wind-up roll, more preferably about 2%–15%. Partial stretching can be accomplished by securing the longitudinal (machine-direction) edges of the sheet and pulling the secured edges apart, thereby stretching the sheet there between. Another preferred means comprises passing the slitted sheet over a stationary expanding device known as a flat expander, manufactured by Shinko Co., Ltd. Osaka, Japan. Any means of providing, preferably continuously, extending or stretching the slitted sheet in the cross direction can be used.

The slitted composite, or the partially stretched slitted composite, is then stretched in the cross-machine direction of the slits to form the finished non-continuous composite. Any means (preferably continuous) for extending or stretching the slitted sheet in the cross-machine direction can be used. The extent of stretching affects the opening size of the void formed by the slits, and therefore affects the percent void opening of the composite, to some extent. In a preferred embodiment, the longitudinal (machine-direction) edges of the sheet are secured by a continuous securing means and the securing means are extended apart, thereby stretching the sheet there between. In a continuous method for stretching the sheet, the secured edges are generally extended apart gradually so as to avoid tearing or non-uniform stretching of the sheet. A preferred method uses non-uniform cross-directional stretching to provide the a stretched non-continuous composite with areas across the width which have been stretched to a greater extent than other areas. The degree of stretching affects the void opening size and therefore the percentage of void openings in that portion of the composite.

The fully stretched non-continuous composite can itself be stored or transported further, by collecting it on wind-up rolls, or, more preferably, the stretched non-continuous absorbent composite is cut or separated into unit sizes for further use in making an absorbent product, or for packaging or storage as an absorbent member. The cutting or separating of the composite sheet into unit sizes can be made by a variety of means that are well known in the art, such as rotary or stationary cutting knives or blades, lasers, scoring and tearing, punching, etc. In a preferred method, a continuous sheet of stretched non-continuous composite is cut into a plurality of unit widths using rotary or stationary cutting knives or blades, each unit width of continuous sheet is then further cut along its length into unit lengths, separated, and used in the making of an absorbent product.

Other methods of forming slits in a continuous composite can be used. Another method involves forming slits oriented in the cross-machine direction. This method can be very similar to the method described above for making continuous slits in the machine direction. The blades are arranged in a predetermined pattern around the cylindrical surface of the knife roll, parallel with the axis of the roller, in the cross-direction. Typically, the blades will extend from the surface of the roller along a line passing though the axis of the roller. Another method for forming a plurality of slits to through the composite in a predetermined pattern involves a batch slitting method. A composite is placed on substantially rigid, flat cutting surface. A press plate having a plurality of blades extending from the surface thereof in a predetermined pattern is positioned into a mechanical or hydraulic press. When the predetermined pattern of blades of the press plate is forced by the press through the composite, for example by pressing the blades through the thickness of the composite, a pattern of slits is formed through the composite in the same predetermined pattern. The blades will generally extend a distance from the surface of the press plate that is at least the thickness of the composite, preferably more. Preferably, the press plate comprises a means for forcing the slitted composite off of the blades after slitting. Such means can comprise slots through which the blades pass, and can comprise a mechanical means such as a spring-loaded plate, or a flexible, resilient means such as a solid foam sponge. Preferably, the cutting surface is a rigid, flat cutting surface that has recesses in the surface thereof which are matched with the extending blades in the press plate.

Another means of forming slits continuously in an absorbent composite is laser cutting.

A non-continuous composite can also be used in a method of forming a plurality of voids directly into a solid, continuous composite. In general, such a method is less preferred because it creates a by-product of void-sized composites that must be recycled, or used in some other way to avoid the expense of scrapping. A continuous method is preferred for forming a plurality of voids or openings into a continuous absorbent composite. Any punching or drilling technique and apparatus can be used to make such voids. The voids are preferably formed in a predetermined pattern and size. Methods for forming voids in sheet-like materials are well-known in the art, and can be used for forming the non-continuous composites of the present invention.

C. Method for Making Semi-Continuous Absorbent Composites

A preferred method for making a semi-continuous absorbent composite involves attaching, preferably bonding, a non-continuous to absorbent composite to a continuous layer, preferably a continuous substrate layer. The continuous layer can also be a continuous composite comprising a substrate and a macrostructure layer. The method for attaching a continuous substrate to a non-continuous composite, (preferably a non-continuous absorbent macrostructure layer thereof) involves steps substantially the same as described above for attaching a substrate to a continuous composite. Additional considerations include the void openings in the non-continuous composite, and the need to retain a non-continuous composite or macrostructure layer in a stretched state while attaching the continuous substrate.

Another preferred method for forming a semi-continuous composite involves cutting a plurality of voids out of an absorbent macrostructure layer of a continuous composite of the present invention, without substantially penetrating the continuous layer, such as the substrate, thereof.

D. Embodiments of Methods for Making Absorbent Composites (Preparation Example)

One hundred parts of precursor particles made in accordance with the Precursor Particle Example are placed into a 5 quart standing kitchen-type mixer. The precursor particles have a particle size such that the precursor particles pass through a standard No. 50 sieve (300 microns) and are retained on a standard No. 100 sieve (150 microns). An aqueous treatment solution is prepared from a mixture of 4.3 parts Kymene Plus (30% resin active), 2.6 parts water and 10.0 parts methanol. This treatment solution is sprayed onto the precursor particles with a Preval sprayer (available from The Precision Valve Corporation of Yonkers, N.Y.). The treatment solution is sprayed onto the precursor particles, while the mixer is operating at slow speed, for a period of about 4 minutes, i.e. until all of the solution is sprayed onto the particles. After spraying, the mixture of wet precursor particles is mixed at the highest speed setting for 2 to 5 minutes. During this high speed mixing, the methanol is evaporated, thus increasing the stickiness of the treated mixture of precursor particles so that they will remain to adhered together. This sticky mixture of treated precursor particles is then fed to an extrusion/compaction unit. The extruder screw has a length of 8 inches (20.3 cm) and contains 5 flights, each flight being 1.5 inches (3.8 cm) in length. The outside diameter of the extruder screw is 1.75 inches (4.45 cm) and the screw-to-housing clearance is 0.20 inches (0.51 cm). The unit is activated such that the extruder screw turns at a rate of 47 rpm. The mixture is extruded between two smooth finish steel compaction rolls (nip rolls) with a fixed (but variable) gap. The compaction rolls have a diameter of 8.975 inches (22.8 cm) and are driven at a rate of 5.4 rpm. The gap between the compaction rolls is 0.015 inches (0.38 mm). The formed aggregate sheets are then separated into approximately 12 to 15 inch (30 to 40 cm) lengths. The oven-cured sheets have a thickness (caliper) of about 0.031 inches (0.8 mm) and a width of about 1.95 inches (4.95 cm). A plasticizer solution containing 65 parts glycerol and 35 parts distilled water is sprayed onto the oven-cured sheets at the rate of 0.9 g, of plasticizer solution, per 1.0 g, of the oven-cured sheet. About ½ hour after treatment with the plasticizer solution, the sheets have sufficient flexibility and tensile strength to be picked up.

CONTINUOUS COMPOSITES

Example 1

In this example, 80 parts of precursor particles made in accordance with the precursor particle example and having the particle size characteristics described in Preparation are used. An aqueous treatment solution prepared from a mixture of 6.0 parts Kymene Plus (30% resin active), 3.5 parts water and 8.5 parts glycerol is also used.

A reciprocating table or shuttle is used in conjunction with a pair of sprayers that apply the treatment solution and a vibratory feeder that deposits the precursor particles. The sprayers and feeder are positioned above the reciprocating surface of the table. Initially a substrate material consisting of a double-ply Bounty® type sheet is placed onto the surface of the table. Then, the table with the Bounty Sheet moves underneath the sprayers, the treatment solution is sprayed onto the surface of the Bounty Sheet (or layer of particles) in a predetermined pattern. As the surface of the table moves further in the same direction and underneath the feeder, a predetermined amount of precursor particles are deposited onto the Bounty Sheet surface (or previous layer of treated particles in subsequent passes). After the particles have been deposited from the feeder to form a layer thereof, the surface of the table moves back in the opposite direction so that the sequence of applying treatment solution/depositing a layer of particles can be repeated.

In total, four layers of precursor particles (0.2 g/in$^2$ of particles per layer) are deposited from the feeder. After each layer of precursor particles has been deposited, a predetermined amount of the treatment solution is sprayed on top of each layer. The amount of treatment solution sprayed initially onto the surface of the table, as well as the first layer of precursor particles, is about 0.018 g/in$^2$. The amount of treatment solution sprayed onto the other four layers of precursor particles is about 0.036 g/in$^2$. In effect, each layer of precursor particles is treated with the same amount of solution.

After the layering of precursor particles and spraying with treatment solution is complete, a relatively cohesive composite sheet of particles is formed. This cohesive composite sheet is then fed by a belt to a compaction unit. The compaction unit consists of two coated steel compaction rolls (nip rolls) with a fixed (but variable) gap. The compaction rolls have a diameter of about 8 inches (20 cm) and are driven at a rate of about 20 rpm. The gap between the compaction rolls is about 0.05 inches (1.25 mm). The resultant aggregate composite sheets (density of 0.9–1.0 g/cc) are stored in plastic bags at ambient room temperature (about 65° C.–72° F., 18.3° C.–22.2° C.) for about 24 hours. During this ambient temperature curing, the Kymene Plus reacts with the polymer material in the surface of the precursor particles, thus causing effective crosslinking. The Kymene in the treatment solution also bonds to the cellulose structure of the Bounty Sheet and to the precursor particles, the Bounty to the cohesive layers of particles thereby bonding. The ambient temperature cured sheets have a thickness (caliper) of about 0.06–0.07 inches (1.5–1.8 mm) and a width of about 4 inches (10 cm). These ambient temperature cured composite sheets have excellent flexibility and tensile strength, and can be handled easily without breaking or tearing.

Example 2

In this example, apparatus 301 shown in FIG. 19 is used. The precursor particles used are made in accordance with the precursor particle example and have a size between 150–250 microns. An aqueous treatment solution is prepared from a mixture of 5.0 parts Kymene Plus (30% resin active), 7.1 parts of water and 12.7 parts glycerol. Feeders 305 are Super Feeder model # 210 SE-00354 vibrating feeders, available from Solids Flow Control, of Charlotte, N.C. Sprayers 304 are model 6218-¼ JAU atomized air actuated nozzle assemblies, available from Spraying Systems, Co., of Wheaton, Ill. For the first two applications, sprayers 304a and 304b deliver the treatment solution to conveyor 303 at a rate of 39.8 grams/mm. For subsequent applications, sprayers 304c through 304f deliver the treatment solution to conveyor 303 at a rate of 79.6 grams/mm. Conveyor 303 is a moving conveyor made from polyurethane, and travels at a speed of 27 ft./mm. Sheet feeder 313 includes a rolled substrate sheet consisting of a double-ply Bounty type sheet to supply the Bounty sheet to conveyor 303 synchronized with the rate of conveyor 303. The pressure applicators are a pair of compaction rolls 306 having 8 inch (20 cm)

diameters and being 12 inches (30.5 cm) wide. The top and bottom rolls 306 are coated with a # 934 Plasma Coating, available from Plasma Coatings, Inc., of Waterbury, Conn.

This example is carried out according to the following steps:

STEP 1: Supply the Bounty sheet to conveyor 303 in synchronization with the rate of conveyor 303.

STEP 2: Spray a predetermined area of the surface of supplied Bounty sheet with treatment solution in an amount substantially equal to 0.05 grams of solution per square inch of the Bounty sheet.

STEP 3: Layer substantially continuously 0.2 grams of precursor particles per square inch of the Bounty sheet onto the same predetermined area.

STEP 4: The first layer of precursor particles on the predetermined area of the Bounty sheet is sprayed with treatment solution in an amount substantially equal to 0.05 grams of solution per square inch of Bounty sheet.

STEP 5: Layer substantially continuously 0.2 grams of precursor particles per square inch of the Bounty sheet onto the same predetermined area.

STEP 6: The second layer of precursor particles on the predetermined area of the Bounty sheet is sprayed with treatment solution in an amount substantially equal to 0.050 grams of solution per square inch of the conveyor.

STEP 7: Steps 5 and 6 are repeated, in order, 2 more times, giving: (a) a total of one initial spraying step and four post-layering spraying steps for a total of 0.25 grams of treatment solution per square inch of the Bounty sheet; and (b) a total of four layering steps for a total of 0.8 gram of precursor particles per square inch of the Bounty sheet. An absorbent composite is now formed.

STEP 8: The absorbent composite is passed through the compaction rolls. The gap between the compaction rolls is 0.05 inches (1.25 mm). This produces a sheet having a density of 0.995 g/cc.

STEP 9: The sheet is cured by placing it in a plastic bag and allowing it to sit at ambient temperature (72° F., 22.2° C.) for 48 hours.

The resultant absorbent composite sheet has good flexibility, dry integrity properties, and free gel blocking.

Example 3

A continuous absorbent composite of Example 2 is placed onto a table so that the absorbent macrostructure layer can face upward (the nonwoven sheet is faced to the table). While passing the table under the Preval sprayer, an amount substantially equal to 0.05 grams of solution per square inch of the treatment solution is uniformly applied to the surface of the absorbent macrostructure layer. Then, about 0.004 g/cm$^2$ of a polypropylene nonwoven sheet is registered with the adhesive surface of the absorbent macrostructure layer, thereby forming a continuous absorbent composite having a sandwich structure as shown in FIG. 2.

NON-CONTINUOUS COMPOSITES:

Example 4

After preparing a cutting table, the continuous absorbent composite of Example 2 is placed on a flat cutting surface. A punch cutter which comprises 20 cylindrical blades faced to outside is prepared. Each of the blades has a diameter of 10 mm and the distance between centers of adjacent two blades is designed at 20 mm. The punch cutter is pushed down on the continuous absorbent composite. Therefore, applying adequate pressure (about 0.5–5 kgf/cm 2) through the punch cutter to the continuous absorbent composite on the flat cutting surface, 20 of circular voids penetrating the composite can be formed in the absorbent composite. As a result, a non-continuous absorbent composite can be obtained.

Example 5

The continuous absorbent composite of Example 3 is placed on a flat cutting surface. A razor knife is used to cut a series of parallel lines of interlaced slits completely through the thickness of the continuous absorbent composite, such that the slitted composite has the appearance of FIG. 18. Each individual slit is about 20 mm long, and each slit in a line is separate from the start of the next slit by a slit spacing gap about 5 mm distance. In a first line of slits, the centers of slits are positioned opposite the centers of the slit spacing gaps of the next line. Each parallel line is spaced across the width of the composite a distance of about 0.2 cm from the next line. After the composite has been slit by means of the razor knife, one of the end edges which is parallel with the lines of slits is secured. The other end edge is grasped and is pulled slowly in the perpendicular direction away from the first end edge until the width of the stretched, shifted composite is approximate 1.5–3.0 time of the original width, thus forming the non-continuous composite as shown in FIG. 9.

Example 6

In this example, slit forming device 420 substantially as shown in FIG. 20 is used to form a slitted absorbent composite sheet from a continuous, non-slitted sheet made in accordance with Example 2. The knife roll 422 consists of 50 (fifty) identical knife blades substantially as shown in FIG. 21. Each knife blade has six blades having a length $x_k$ of 20.0 mm, a blade spacing $y_k$ of 4.0 mm, a blade thickness $z_k$ of 0.3 mm, and a blade diameter of about 45 mm. Each knife blade is made of tungsten. Alternating knife blades are inverted when mounted on the shaft 423 so that the blades thereof are offset from the blade of the adjacent plate by about 15°. Shims 439 are placed between adjacent knife blades to separate the planes of the blade tips by a distance of 1.9 mm. Recess roll 424 is constructed of a Teflon material and has a matching recess 441 for each knife blade. The stripping plate 425 is made of stainless steel of 3 mm thickness.

To assist in the stripping of the slitted composite from the knife blades, a sheet of waxed paper (approximately 2 mil, 0.050 mm) is registered on both surfaces of the absorbent composite prior to slitting. The absorbent composite is fed into the opening 421 between the stripping plate 425 and the recess roll 424 with the Bounty® substrate layer facing downward toward the knife roll. Two 100 mm outside diameter air cylinders are used to force the knife roll upward with an air pressure of 2.5 kg to 5 kg force per square centimeter. The resulting slitted composite is partially stretched (about 15%) after existing the slit forming device. A non-continuous "netted" composite is then formed by stretching the width (cross-machine direction) of the slitted composite uniformly by 100%.

SEMI-CONTINUOUS COMPOSITES

Example 7

After preparing a cutting table, a continuous absorbent sheet of Preparation Example is placed on a flat cutting surface. A punch cutter which comprises 20 circular blades faced to outside is prepared. Each of the blades has a diameter of 10 mm and the distance between centers of adjacent two blades is designed at 20 mm. The punch cutter is pushed down on the continuous absorbent composite. Therefore, applying adequate pressure (about 0.5–5 kgf/cm$^2$) through the punch cutter to the continuous absorbent sheet on the flat cutting surface, 20 of circular voids penetrating the composite can be formed in the absorbent sheet. As a result, a non-continuous absorbent sheet can be formed.

A double-ply Bounty sheet having the same size as the non-continuous absorbent sheet is prepared and the treatment solution is also sprayed onto the Bounty sheet with the Preval sprayer. After the cellulosic material of the surface of the Bounty sheet is treated with a sufficient amount (e.g. an amount substantially equal to 0.05 grams of solution per square inch ) of the treatment solution uniformly, the non-continuous absorbent sheet is placed on the surface of the Bounty sheet. The two sheets are extruded into the compaction rolls and are applied an opposing pressure thereby. As a result, a semi-continuous absorbent composite can be obtained.

USES OF ABSORBENT COMPOSITES

The continuous, non-continuous, and semi-continuous absorbent composites (hereinafter, generally referred to simply as absorbent composites unless specification identified otherwise) can be used for many purposes in many fields of use. For example, the absorbent composites can be used for packing containers; drug delivery devices; wound cleaning devices; burn treatment devices; ion exchange column materials; construction materials; agricultural or horticultural materials such as seed sheets or water-retentive materials; and industrial uses such as sludge or oil dewatering agents, materials for the prevention of dew formation, desiccants, and humidity control materials.

Figure 26:
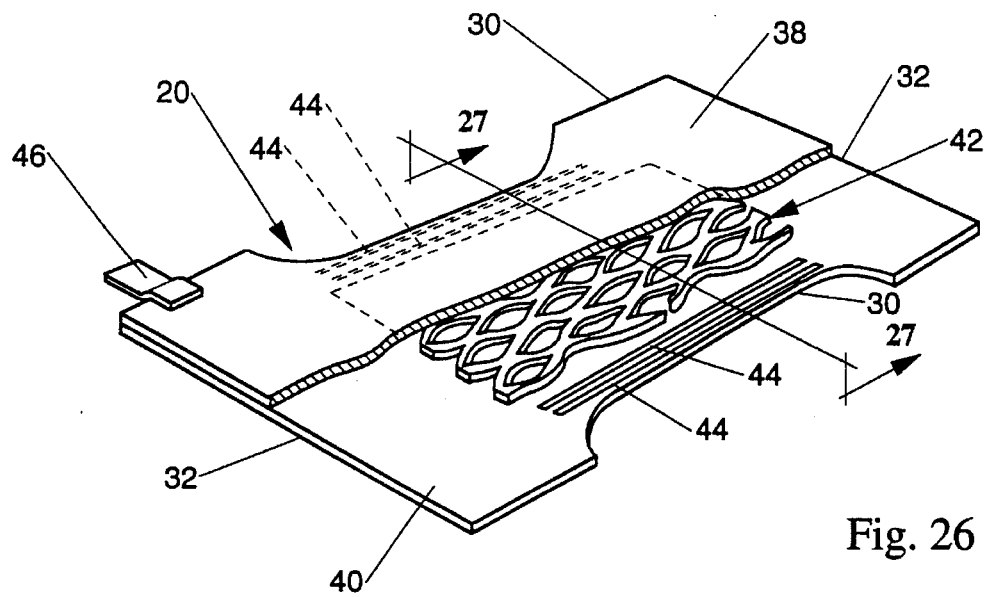
FIG. 26 is a perspective view of a disposable diaper embodiment according to the present invention wherein portions of the topsheet have been cut-away to more clearly show an underlying absorbent core which comprises an non-continuous absorbent composite of the present invention.

Because of the unique absorbent properties of the porous, absorbent macrostructures used in absorbent composites of the present invention, they are especially suitable for use as absorbent cores in absorbent articles, especially disposable absorbent articles. As used herein, the term "absorbent article" refers to articles which absorb and contain body exudates and more specifically refers to articles which are placed against or in proximity to the body of the wearer to absorb and contain the various exudates discharged from the body. Additionally, "disposable" absorbent articles are those which are intended to be discarded after a single use (i.e., the original absorbent article in its whole is not intended to be laundered or otherwise restored or reused as an absorbent article, although certain materials or all of the absorbent article may be recycled, reused, or composted). A preferred embodiment of a disposable absorbent article, diaper 20, is shown in FIG. 26. As used herein, the term "diaper" refers to a garment generally worn by infants and incontinent persons that is worn about the lower torso of the wearer. It should be understood, however, that the present invention is also applicable to other absorbent articles such as incontinent briefs, incontinent pads, training pants, diaper inserts, sanitary napkins, facial tissues, paper towels, and the like.

The non-continuous absorbent composites, preferably the net-like shape absorbent composite, and preferably comprising 90% or more by weight of absorbent gelling particles in the absorbent macrostructures, provide highly absorbent, thin and flexible absorbent cores. When using the absorbent composites of the present invention as absorbent cores, very thin and flexible diapers and other absorbent articles can be obtained. Especially, use of the non-continuous absorbent composites, preferably net-like shape absorbent composites in a diaper provides highly flexible absorbent cores. Consequently, use of the non-continuous absorbent composites of the present invention can provide diapers and other absorbent articles with high absorbency, thinness and flexibility.

FIG. 26 is a perspective view of the diaper 20 of the present invention in its uncontracted state (i.e., with all the elastic induced contraction removed) with portions of the structure being cut-away to more clearly show the construction of the diaper 20 and with the portion of the diaper 20 which contacts the wearer facing the viewer. The diaper 20 is shown in FIG. 26 to preferably comprise a liquid pervious topsheet 38; a liquid impervious backsheet 40 joined with the topsheet 38; an absorbent core 42 positioned between the topsheet 38 and the backsheet 40; elastic members 44; and tape tab fasteners 46. Preferably, the diaper 20 further comprises a tissue interposed at least between the absorbent core 42 and the topsheet 38, more preferably provided to enclose the absorbent core 42. The topsheet 38, the backsheet 40, the absorbent composite core 42, the elastic members 44 and the tissue can be assembled in a variety of well known configurations. Absorbent composite core 42 can be selected from any continuous, non-continuous or semi-continuous absorbent composite disclosed herein. Preferably, absorbent composite core 42 comprises a non-continuous absorbent composite, more preferably a net-like shape absorbent composite, as shown in FIG. 26.

A preferred diaper configuration for a diaper comprising an absorbent composite core 42 is described generally in U.S. Pat. No. 3,860,003 (Buell), issued Jan. 14, 1975, which is incorporated by reference. Alternatively preferred configurations for disposable diapers herein are also disclosed in U.S. Pat. No. 4,808,178 (Aziz et al), issued Feb. 28, 1989; U.S. Pat. No. 4,695,278 (Lawson), issued Sep. 22, 1987; U.S. Pat. No. 4,816,025 (Foreman), issued Mar. 28, 1989; and U.S. Pat. No. 5,15,092 (Buell et al.), issued Sep. 29, 1992, all of which are incorporated by reference.

FIG. 26 shows a preferred embodiment of the diaper 20 in which the topsheet 38 and the backsheet 40 are co-extensive and have length and width dimensions generally larger than those of the absorbent composite core 42. The topsheet 38 is joined with and superimposed on the backsheet 40 thereby forming the periphery of the diaper 20. The periphery defines the outer perimeter or the edges of the diaper 20. The periphery comprises the end edges 32 and the longitudinal edges 30.

The absorbent composite core 42 is also preferably used as an absorbent means in pull-on diapers, such as those disclosed in U.S. Pat. No. 5,074,854 (Davis), issued Dec. 24, 1991, which is incorporated by reference.

The topsheet 38 is compliant, soft feeling, and non-irritating to the wearer's skin. Further, the topsheet 38 is liquid pervious permitting liquids to readily penetrate through its thickness. A suitable topsheet 38 can be manufactured from a wide range of materials such as porous foams, reticulated foams, apertured plastic films, natural fibers (e.g., wood or cotton fibers), synthetic fibers (e.g., polyester or polypropylene fibers) or from a combination of natural and synthetic fibers. Preferably, the topsheet 38 is made of a hydrophobic material to isolate the wearer's skin from liquids in the absorbent core 42.

A particularly preferred topsheet 38 comprises staple length polypropylene fibers having a denier of about 1.5, such as Hercules type 151 polypropylene marketed by Hercules, Inc. of Wilmington, Del. As used herein, the term "staple length fibers" refers to those fibers having a length of at least about 15.9 mm (0.62 inches).

There are a number of manufacturing techniques which can be used to manufacture the topsheet 38. For example, the topsheet 38 can be woven, nonwoven, spunbonded, carded, or the like. A preferred topsheet is carded, and thermally bonded by means well known to those skilled in the fabrics art. Preferably, the topsheet 38 has a weight from about 18 to about 25 grams per square meter, minimum dry tensile strength of at least about 400 grams per centimeter in the machine direction, and a wet tensile strength of at least about 55 grams per centimeter in the cross-machine direction.

The backsheet 40 is impervious to liquids and is preferably manufactured from a thin plastic film, although other flexible liquid impervious materials may also be used. The backsheet 40 prevents the exudates absorbed and contained in the absorbent core 42 from wetting articles which contact the diaper 20 such as bedsheets and undergarments. Preferably, the backsheet 40 is polyethylene film having a thickness from about 0.012 (0.5 mil) to about 0.051 centimeters (2.0 mils), although other flexible, liquid impervious materials can be used. As used herein, the term "flexible" refers to materials which are compliant and which will readily conform to the general shape and contours of the wearer's body.

A suitable polyethylene film is manufactured by Monsanto Chemical Corporation and marketed in the trade as Film No. 8020. The backsheet 40 is preferably embossed and/or matte finished to provide a more clothlike appearance. Further, the backsheet 40 may permit vapors to escape from the absorbent core 42 while still preventing exudates from passing through the backsheet 40.

The size of the backsheet 40 is dictated by the size of the absorbent core 42 and the exact diaper design selected. In a preferred embodiment, the backsheet 40 has a modified hourglass-shape extending beyond the absorbent core 42 a minimum distance of at least about 1.3 centimeters to about 2.5 centimeters (about 0.5 to about 1.0 inch) around the entire diaper periphery.

The topsheet 38 and the backsheet 40 are joined together in any suitable manner. As used herein, the term "joined" encompasses configurations whereby the topsheet 38 is directly joined to the backsheet 40 by affixing the topsheet 38 directly to the backsheet 40, and configurations whereby the topsheet 38 is indirectly joined to the backsheet 40 by affixing the topsheet 38 to intermediate members which in turn are affixed to the backsheet 40. In a preferred embodiment, the topsheet 38 and the backsheet 40 are affixed directly to each other in the diaper periphery by attachment means (not shown) such as an adhesive or any other attachment means as known in the art. For example, a uniform continuous layer of adhesive, a patterned layer of adhesive, or an array of separate lines or spots of adhesive can be used to affix the topsheet 38 to the backsheet 40.

Tape tab fasteners 46 are typically applied to the .back waistband region of the diaper 20 to provide a fastening means for holding the diaper on the wearer. The tape tab fasteners 46 can be any of those well known in the art, such as the fastening tape disclosed in U.S. Pat. No. 3,848,594 (Buell), issued Nov. 19, 1974, which is incorporated by reference. These tape tab fasteners 46 or other diaper fastening means are typically applied near the corners of the diaper 20.

The elastic members 44 are disposed adjacent the periphery of the diaper 20, preferably along each longitudinal edge 30, so that the elastic members 44 tend to draw and hold the diaper 20 against the legs of the wearer. Alternatively, the elastic members 44 can be disposed adjacent either or both of the end edges 32 of the diaper 20 to provide a waistband as well as or rather than leg cuffs. For example, a suitable waistband is disclosed in U.S. Pat. No. 4,515,595 (Kievit et al), issued May 7, 1985, which is incorporated by reference. In addition, a method and apparatus suitable for manufacturing a disposable diaper having elastically contractible elastic members is described in U.S. Pat. No. 4,081,301 (Buell), issued Mar. 28, 1978, which is incorporated by reference.

The elastic members 44 are secured to the diaper 20 in an elastically contractible condition so that in a normally unrestrained configuration, the elastic members 44 effectively contract or gather the diaper 20. The elastic members 44 can be secured in an elastically contractible condition in at least two ways. For example, the elastic members 44 can be stretched and secured while the diaper 20 is in an uncontracted condition. Alternatively, the diaper 20 can be contracted, for example, by pleating, and the elastic members 44 secured and connected to the diaper 20 while the elastic members 44 are in their unrelaxed or unstretched condition.

In the embodiment illustrated in FIG. 26, the elastic members 44 extend along a portion of the length of the diaper 20. Alternatively, the elastic members 44 can extend the entire length of the diaper 20, or any other length suitable to provide an elastically contractible line. The length of the elastic members 44 is dictated by the diaper design.

The elastic members 44 can be in a multitude of configurations. For example, the width of the elastic members 44 can be varied from about 0.25 millimeters (0.01 inches) to about 25 millimeters (1.0 inch) or more; the elastic members 44 can comprise a single strand of elastic material or can comprise several parallel or non-parallel strands of elastic material; or the elastic members 44 can be rectangular or curvilinear. Still further, the elastic members 44 can be affixed to the diaper in any of several ways which are known in the art. For example, the elastic members 44 can be ultrasonically bonded, heat and pressure sealed into the diaper 20 using a variety of bonding patterns or the elastic members 44 can simply be glued to the diaper 20.

The absorbent composite core 42 of the diaper 20 is positioned between the topsheet 38 and the backsheet 40. The absorbent composite core 42 can be manufactured in a wide variety of sizes and shapes (e.g., rectangular, hourglass, asymmetrical, etc.). The total absorbent capacity of the absorbent core 42 should, however, be compatible with the design liquid loading for the intended use of the absorbent article or diaper. The size and absorbent capacity of the absorbent composite core 42 can vary to accommodate wearers ranging from infants through adults.

Figure 27:
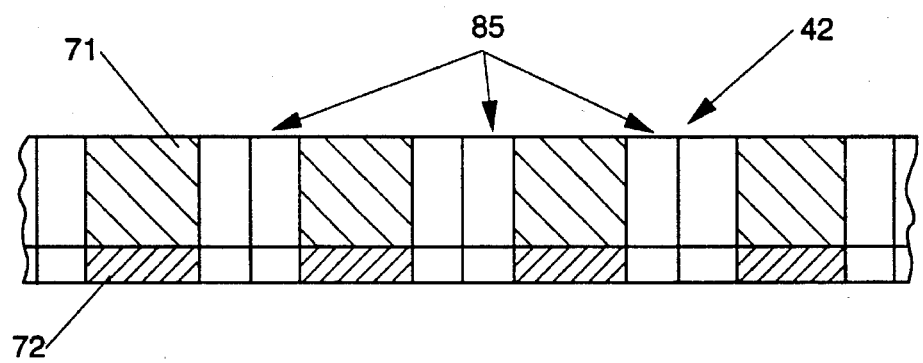
FIG. 27 is a cross-sectional view of the non-continuous absorbent composite core of the diaper shown in FIG. 26 taken along sectional line 27—27.

As shown in FIG. 27, another preferred embodiment of the diaper 20 has a rectangular-shaped absorbent composite core 42 comprising a non-continuous absorbent composite of the present unit, wherein the composite has an absorbent macrostructure layer 71 and a substrate layer 72, and has voids 85 penetrating therein.

Alternatively, the absorbent cores 42 of the present invention can consist solely of one or more absorbent composites of the present invention; can comprise a combination of the absorbent composites of the present invention; or any other absorbent core configurations including one or more of the absorbent composite of the present invention.

Figure 28:
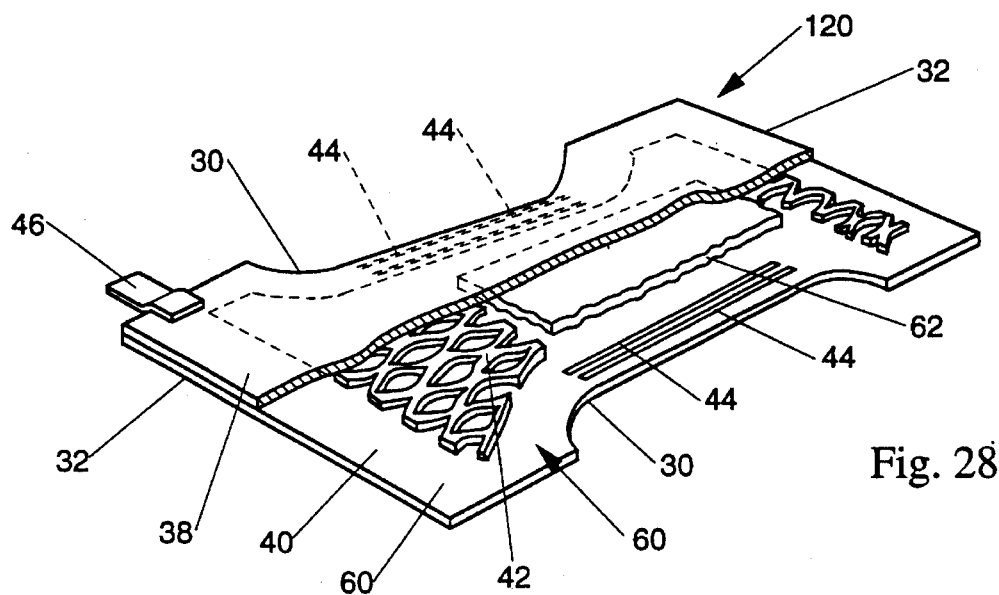
FIG. 28 is a perspective view of another disposable diaper embodiment according to the present invention wherein portions of the topsheet have been cut away to more clearly show an underlying absorbent core which comprises an non-continuous absorbent composite of the present invention.

An alternative embodiment of the diaper 120 comprising an absorbent assembly 60 comprising, an hourglass-shaped non-continuous absorbent composite 42 and an acquisition component 62. The acquisition component 62 can be positioned above the absorbent composite core 42, below the absorbent composite core 42, and both above and below the absorbent composite core 42. FIG. 28 shows such as diaper 120 having an acquisition means 62 positioned above the absorbent composite core 42 (i.e., between the absorbent composite core 42 and the topsheet 38). Preferably, the diaper 120 further comprises a tissue interposed at least between the absorbent composite core 42 and the topsheet 38, more preferably provided to enclose the absorbent composite core 42. In a preferred embodiment an acquisition means 62 is positioned both above and below the non-continuous, composite core 42.

Acquisition component 62 serves to quickly collect and temporarily hold discharged liquids and to transport such liquids by wicking from the point of initial contact to other parts of the acquisition component 62 and to the absorbent composite core 42. The acquisition component 62 preferably comprises a web or batt of fiber materials. Various types of fiber material can be used in the acquisition component 62. Cellulosic fibers are generally preferred for use herein, wood pulp fibers being especially preferred. More preferably, chemically stiffened cellulosic fibers, air felt fibers, synthetic fibers, large cell hydrophilic absorbent foam materials or a mixture thereof can be used as the acquisition means 62. The acquisition component 62 can also contain specific amounts of a particulate, absorbent, polymeric composition. The acquisition component 62, for example, can contain up to about 50% by its weight of the polymeric composition. In the most preferred embodiments, the acquisition component 62 contains from 0% to about 8% by its weight of a particulate, absorbent, polymeric composition. Exemplary embodiments of the acquisition component 62 useful in the present invention are described in U.S. Pat. No. 4,673,402 (Weisman et al), issued Jun. 16, 1987; and U.S. Pat. No. 4,834,735 (Alemany et al), issued May 30, 1989, both of which are incorporated by reference. An acquisition component having a storage zone and an acquisition zone with a lower average density and a lower average basis weight per unit area than the storage zone so that the acquisition zone can effectively and efficiently rapidly acquire discharged liquid are especially preferred for use herein.

The acquisition component 62 can be of any desired shape, for example, rectangular, oval, oblong, asymmetric or hourglass-shaped. The shape of the acquisition component 60 can define the general shape of the resulting diaper 120. The acquisition component 60 of the present invention need not be the same size as the absorbent composite core 42, and can, in fact, have a top (or bottom) surface area which is substantially smaller or larger than the top (or bottom) surface area of the absorbent composite core 42. In a preferred embodiment comprising a non-continuous (for example, a "netted") absorbent composite, the acquisition component 62 and the absorbent composite 42 are preferably compressed together.

In alternatively preferred embodiments, a plurality of absorbent composite core sheets, preferably from two to six sheets in the form of strips, can be substituted for the single absorbent composite core 42. The plurality of absorbent composite sheets can be arranged in any pattern though preferably parallel and in the longitudinal direction of the diaper.

By spacing absorbent composite strips from one another, a more effective surface area is presented for acquiring and holding the discharge liquids. This is particularly true since the spaced absorbent composite strips can swell and expand in the direction of their width, without interfering with the ability of adjacent strips to acquire discharged liquids.

The absorbent composite core 42 can also be used as an absorbent means in catamenial absorbent products. Since products generally comprise a liquid pervious topsheet overlaying the absorbent means, and a liquid impervious backsheet on the opposing surface of the absorbent means. The topsheet and backsheet can be selected from materials as described herein above. Preferred catamenial products comprise a formed-film, apertured topsheet as disclosed in U.S. Pat. No. 4,285,343 (McNair), issued Aug. 25, 1981; U.S. Pat. No. 4,608,047 (Mattingly), issued Aug. 26, 1986; and U.S. Pat. No. 4,687,478 (Van Tilburg), issued Aug. 18, 1987, all of which are incorporated by reference.

Preferred catamenial products can comprise wings, side flaps, and other structures and elements, as described in co-pending, commonly-assigned U.S. application Ser. No. 984,071, to Yasuko Morita, entitled "Absorbent Article Having Elasticized Side Flaps ", Attorney Docket No. JA-09RM, filed Nov. 30, 1992, incorporated herein by reference.

TEST METHODS

Synthetic Urine

The specific synthetic urine used in the test methods of the present invention is referred to herein as "Synthetic Urine". The Synthetic Urine is commonly known as Jayco SynUrine and is available from Jayco Pharmaceuticals Company of Camp Hill, Pa. The formula for the Synthetic Urine is: 2.0 g/l of KCl; 2.0 g/l of Na2SO4; 0.85 g/l of (NH4)H2PO4; 0.15 g/l (NH4)2HPO4; 0.19 g/l of CaCl2 and 0.23 g/l of MgCl2. All of the chemicals are of reagent grade. The pH of the Synthetic Urine is in the range of 6.0 to 6.4.

A. Absorptive Capacity of the Precursor Particles

The polymeric composition is placed within a "tea bag", immersed in an excess of Synthetic Urine for a specified period of time, and then centrifuged for a specific period of time. The ratio of polymeric composition final weight after centrifuging minus initial weight (net fluid gain) to initial weight determines the Absorptive Capacity.

The following procedure is conducted under standard laboratory conditions at 23° C. (73° F.) and 50% relative humidity. Using a 6 cm×12 cm cutting die, the tea bag material is cut, folded in half lengthwise and sealed along two sides with a T-bar sealer to produce a 6 cm×6 cm tea bag square. The tea bag material utilized is a grade 1234 heat sealable material, obtainable from C. H. Dexter, Division of the Dexter Corp., Windsor Locks, Conn., U.S.A., or equivalent. Lower porosity tea bag material should be used if required to retain fine particles. 0.200 grams plus or minus 0.005 grams of the polymeric composition is weighed onto a weighing paper and transferred into the tea bag, and the top (open end) of the tea bag is sealed. An empty tea bag is sealed at the top and is used as a blank. Approximately 300 milliliters of Synthetic Urine are poured into a 1,000 milliliter beaker. The blank tea bag is submerged in the Synthetic Urine. The tea bag containing the polymeric composition (the sample tea bag) is held horizontally to distribute the material evenly throughout the tea bag. The tea bag is laid on the surface of the Synthetic Urine. The tea bag is allowed to wet, for a period of no more than one minute, and then is fully submerged and soaked for 60 minutes. Approximately 2 minutes after the first sample is submerged, a second set of tea bags, prepared identically to the first set of blank and sample tea bags, is submerged and soaked for 60 minutes in the same manner as the first set. After the prescribed soak time is elapsed, for each set of tea bag samples, the tea bags are promptly removed (using tongs) from the Synthetic Urine. The samples are then centrifuged as described below. The centrifuge used is a Delux Dynac II Centrifuge, Fisher Model No. 05-100-26, obtainable from Fisher Scientific Co. of Pittsburgh, Pa., or equivalent. The centrifuge should be equipped with a direct read tachometer and an electric brake. The centrifuge is further equipped with a cylindrical insert basket having an approximately 2.5 inch (6.35 cm) high outer wall with an 8.435 inch (21.425 cm) outer diameter, a 7.935 inch (20.155 cm) inside diameter, and 9 rows each of approximately 106 3/32 inch (0.238 cm) diameter circular holes equally spaced around the circumference of the outer wall, and having a basket floor with six 1/4 inch (0.635 cm) diameter circular drainage holes equally spaced around the circumference of the basket floor at a distance of 1/2 inch (1.27 cm) from the interior surface of the outer wall to the center of the drainage holes, or an equivalent. The basket is mounted in the centrifuge so as to rotate, as well as brake, in unison with the centrifuge. The sample tea bags are positioned in the centrifuge basket with a folded end of the tea bag in the direction of the centrifuge spin to absorb the initial force. The blank tea bags are placed to either side of the corresponding sample tea bags. The sample tea bag of the second set must be placed opposite the sample tea bag of the first set; and the blank tea bag of the second set opposite the blank tea bag of the first set, to balance the centrifuge. The centrifuge is started and allowed to ramp up quickly to a stable speed of 1,500 rpm. Once the centrifuge has been stabilized at 1,500 rpm, a tinier is set for 3 minutes. After 3 minutes, the centrifuge is turned off and the brake is applied. The first sample tea bag and the first blank tea bag are removed and weighed separately. The procedure is repeated for the second sample tea bag and the second blank tea bag. The Absorptive Capacity (ac) for each of the samples is calculated as follows: ac=(sample tea bag weight after centrifuge minus blank tea bag weight after centrifuge minus dry polymeric composition weight) divided by (dry polymeric composition weight). The Absorptive Capacity value for use herein is the average Absorptive Capacity of the two samples.

B. Fluid Stability

The objective of this method is to determine the stability of macrostructure aggregates and absorbent composites of the present invention upon exposure to Synthetic Urine.

The sample macrostructure or absorbent composite is placed in a shallow dish. An excess amount of Synthetic Urine is added to the macrostructure or absorbent composite.

The swelling of the macrostructure or absorbent composite is observed until equilibrium is reached. During the observation of the swelling macrostructure or absorbent composite, the macrostructure or absorbent composite is observed for small particles breaking off from the main absorbent aggregate, platelet-like particles floating away from the main absorbent aggregate, or particles breaking and floating away from the main absorbent aggregate. If the absorbent aggregate has a large number of broken away component particles, the macrostructure or absorbent composite is considered unstable. The macrostructure or absorbent composite should also be observed for isotropic swelling. If the absorbent aggregate remains relatively stable and the relative geometry and spatial relationships of the precursor particles and the pores are maintained after the test procedure, the macrostructure or absorbent composite is considered stable. Preferably, fluid stable macrostructures or absorbent composites are capable of being picked up in their swollen state without breaking apart.

C. Precursor Particle Size and Mass Average Particle Size

The particle size distribution on a weight percent basis of a 10 gram bulk sample of the precursor particles is determined by sieving the sample through a set of 19 sieves ranging in size from a standard #20 sieve (850 microns) through a standard #400 sieve (38 microns). The sieves are standard sieves as obtainable from the Gilson Company, Inc. of Worthington, Ohio. The procedure is carried out on three stacks of sieves at a time since the equipment used cannot hold all 19 sieves at one time. A first stack contains sieves #20, 25, 30, 35, 40, 45, and 50 plus the sieve pan; the second stack contains sieves #60, 70, 80, 100, 120, and 140 plus the sieve pan; the third stack contains sieves # 170, 200, 230, 270, 325, and 400 plus the sieve pan. The precursor particles remaining on each of these sieves are then weighed to determine the particle size distribution on a weight percent basis.

The first stack of sieves is mounted on a shaker and 10.0 grams plus or minus 0.00 grams of the sample is placed on the #20 sieve. The shaker used is a Vibratory 3-inch Sieve Shaker Model SS-5 as obtainable from the Gilson Company, Inc. of Worthington, Ohio. The stack is shaken for 3 minutes at approximately 2100 vibrations per minute ("6" on the instrument dial). The sieve pan is then removed and the stack set aside for later weighing. Using a soft brush, the sample remaining on the sieve pan is transferred onto a weighing paper. The second stack of sieves is mounted on the shaker and the sample on the weighing paper is transferred onto the #60 sieve. The second stack is shaken for 3 minutes at approximately 2100 vibrations per minute, the sample remaining on the sieve pan being transferred to a weighing paper and the stack set aside. The third stack of sieves is mounted on the shaker and the sample on the weighing paper is transferred onto the #170 sieve. The third stack is shaken for 3 minutes at approximately 2100 vibrations per minute. A soft brush is used to transfer the contents of each given sieve onto a tared weighing paper. The sample is weighed on a standard three place scale and the weight of the sample on the specific sieve is recorded. This step is repeated, using a fresh weighing paper for each sample, for each sieve, and for the sample remaining on the sieve pan after the third stack of sieves has been shaken. The method is repeated for two additional 10 gram samples. The average of the weights of the three samples for each sieve determine the average particle size distribution on a weight percent basis for each sieve size.

The Mass Average Particle Size of the 10 gram bulk sample is calculated as follows:

$$maps = \Sigma(D_i \times M_i)/\Sigma M_i$$

wherein maps is the mass average particle size; $M_i$ is the weight of the particles on the specific sieve; and $D_i$ is the "size parameter" for the specific sieve. The size parameter, $D_i$ of a sieve is defined to mean the size (in microns) of the next highest sieve. For example, a standard #50 sieve has a size parameter of 355 microns, which corresponds to the size of the openings in a standard #45 sieve (the next highest sieve). The Mass Average Particle Size for use herein is the average of the mass average particle size of the three samples.

Precursor Particle Example

A jacketed 10 liter twin arm stainless steel kneader measuring 220 mm×240 mm in the opening and 240 mm in depth, and having two Sigma type blades possessing a rotational diameter of 120 mm is sealed with a lid. An aqueous monomer solution is prepared consisting of 37 weight % monomer. The monomer consists of 75 mole % sodium acrylate and 25 mole % acrylic acid. 5500 grams of the aqueous monomer solution is charged to the kneader vessel, which is subsequently purged with nitrogen gas to remove the remaining entrapped air. Then, the two Sigma type blades are set rotating at rates of 46 rpm and the jacket is heated by the passage of 35° C. water. 2.8 g of sodium persulfate and 0.14 g of L-ascorbic acid are added as polymerization initiators. Polymerization begins about four minutes after the addition of the initiators. A peak temperature of 82° C. is reached inside the reaction system 15 minutes after the addition of the initiators. The hydrated gel polymer is divided into particles about 5 mm in size as the stirring is continued. The lid is removed from the kneader 60 minutes after the start of the polymerization and the material is removed from the kneader.

The resultant hydrated aqueous gel polymer thus obtained is spread on a standard #50 size metal gauze and dried with hot air at 150° C. for 90 minutes. The dried particles are pulverized with a hammer type crusher and sifted with a standard #20 sieve (850 microns) to obtain particles that pass through the standard #20 sieve. The mass average particle size of these particles is 405 microns.

D. Measurement of Wicking Ratio and Wicking Distance for Absorbent Composites

The fluid wicking rate or speed and wicking distance of absorbent composites are measured in the following. After preparing an absorbent composite having a width of 2 cm and a length of 30 cm, the absorbent composite is attached to a parafilm compartment so that one end of the absorbent composite juts out from the parafilm compartment at 1 cm length. The parafilm compartment has edges sealed to prevent any evaporation. After filling a vessel with the Synthetic Urine, the parafilm compartment is hung on the vessel to put the jutting portion (1 cm) of the end of the absorbent composite in the Synthetic Urine. After the start of the test, the fluid advancement is recorded every ten seconds. The wicking rate is determined by the advanced distance after 4 minutes period. Also, the wicking distance is determined by the last distance at 20 hours after from the start of recording. This measurement is carried out under the normal room temperature (about 25° C.).

What is claimed is:

1. An absorbent composite comprising:

(a) at least one absorbent macrostructure layer comprising a multiplicity of interconnected absorbent gelling particles, wherein at least a portion of the surfaces of said particles are crosslinked, and (b) at least one means bonded to said absorbent macrostructure layer by a crosslinking agent capable of crosslinking said particles for distributing liquid to be absorbed by said absorbent macrostructure layer.

2. The absorbent composite according to claim 1 wherein said crosslinking agent is a cationic amino-epichlorohydrin adduct.

3. An absorbent composite comprising:

(a) at least one absorbent macrostructure layer comprising a multiplicity of interconnected absorbent gelling particles, wherein at least a portion of the surfaces of said particles are crosslinked, and (b) at least one support bonded to said absorbent macrostructure layer by a crosslinking agent capable of crosslinking said particles.

4. The absorbent composite according to claim 3 wherein said crosslinking agent is a cationic amino-epichlorohydrin adduct.

5. The absorbent composite according to claim 4 wherein said crosslinking is a cationic polymeric amino-epichlorohydrin resin.

6. The absorbent composite according to claim 5 further comprising at least one means bonded to said absorbent macrostructure layer for distributing liquid to be absorbed by said absorbent macrostructure layer.

7. An absorbent composite comprising:

(a) a first absorbent macrostructure layer having a first and a second surface, comprising a multiplicity of interconnected absorbent gelling particles, wherein at least a portion of the surfaces of said particles are crosslinked, and (b) a first substrate having a first surface bonded to said first surface of said first absorbent macrostructure layer by a crosslinking agent capable of crosslinking said particles.

8. The absorbent composite according to claim 7 further comprising:

(c) a second substrate having a first surface bonded to said second surface of said absorbent macrostructure layer by said crosslinking agent.

9. The absorbent composite according to claim 7 further comprising:

(d) a second absorbent macrostructure layer having a first surface bonded to a second surface of said first substrate.

10. An absorbent composite comprising:

(a) a plurality of absorbent macrostructure layers, each layer having a first and a second surface and comprising a multiplicity of interconnected absorbent gelling particles, wherein at least a portion of the surfaces of said particles are crosslinked, and (b) a plurality of substrates interposed alternately between said plurality of absorbent macrostructure layers and bonded thereto by a crosslinking agent capable of crosslinking said particles.

11. The absorbent composite according to claim 10 wherein said crosslinking agent is a cationic amino-epichlorohydrin adduct.

12. The absorbent composite according to claim 11 wherein said substrate is a cellulosic material, and wherein said substrate is chemically bonded to said surface of said absorbent macrostructure layer by said cationic amino-epichlorohydrin adduct.

13. The absorbent composite according to claim 12 wherein said substrate comprises a plurality of capillary elements having a length for distributing liquid therethrough along said length.

14. The absorbent composite according to claim 12 wherein said particles have a mass average particle size of from about 20 microns to about 1500 microns.

15. The absorbent composite according to claim 12 wherein said particles have substantially the same mass average particle size.

16. The absorbent composite according to claim 12 wherein said absorbent macrostructure layer comprises from about 50% to about 100% by weight of said particles.

17. The absorbent composite according to claim 12 wherein said absorbent macrostructure layer comprises a plurality of particle layers, wherein at least two adjacent particle layers have substantially different particle properties.

18. The absorbent composite according to claim 17 wherein said particles have a different mass average particle size in each of said adjacent layers.

19. The absorbent composite according to claim 12 wherein said absorbent macrostructure layer has an average basis weight of from about 100 g/m$^2$ to about 1500 g/m$^2$ and a density of from about 0.6 g/cc to about 1.1 g/cc.

20. The absorbent composite according to claim 19 wherein said average basis weight is from about 250 g/m$^2$ to about 1200 g/m$^2$.

21. The absorbent composite according to claim 20 wherein said absorbent macrostructure layer is in the form of a sheet.

22. The absorbent composite according to claim 12 wherein said absorbent macrostructure layer further comprises a plasticizer.

23. The absorbent composite according to claim 21 wherein said plasticizer is from about 5 parts to about 100 parts by weight, per 100 parts by weight of said absorbent gelling particles.

24. The absorbent composite according to claim 23 wherein said plasticizer comprises glycerol or a mixtures of glycerol and water.

25. The absorbent composite according to claim 12 wherein said cationic amino-epichlorohydrin adduct is a cationic polymeric amino-epichlorohydrin resin.

26. The absorbent composite according to claim 25 wherein said cationic polymeric resin is a reaction product between epichlorohydrin and a polyethyleneimine or a polyamide-polyamine.

27. The absorbent composite according to claim 12 wherein said substrate is selected from the group consisting of fibrous layers and foam layers.

28. The absorbent composite according to claim 27 wherein said substrate is a solid foam layer having an average pore size of from about 1.0 microns to about 1000 microns.

29. The absorbent composite according to claim 28 wherein said solid foam layer has an average pore size of from about 1.0 microns to about 200 microns.

30. The absorbent composite according to claim 29 wherein said average pore size is of from about 5.0 microns to about 70 microns.

31. The absorbent composite according to claim 30 wherein said solid foam layer is a wet expansible foam layer.

32. An absorbent article comprising: (i) a liquid pervious topsheet; (ii) a liquid impervious backsheet; and (iii) an absorbent core positioned between said topsheet and said backsheet, wherein said absorbent core comprises at least one absorbent composite of claim 7, 8, 9 and 10.

33. The absorbent article of claim 32 wherein said absorbent core further comprises an acquisition component positioned between said topsheet and said absorbent composite.

34. The absorbent article of claim 33 wherein said acquisition component comprises a member selected from the group consisting of chemically stiffened cellulosic fibers, air felt fibers, synthetic fibers, hydrophilic absorbent foam materials, and mixtures thereof.

35. The absorbent article according to claim 10 wherein said absorbent article is a diaper or an adult incontinence product.

36. The absorbent composite according to claim 10 wherein said particles are made from a polymer material selected from the group consisting of hydrolyzed starch-acrylonitrile graft copolymers; partially neutralized starch-acrylonitrile graft copolymers; starch-acrylic acid graft copolymers, partially neutralized starch-acrylic acid graft copolymers; saponified vinyl acetate-acrylic ester copolymers; hydrolyzed acrylonitrile copolymers; hydrolyzed acrylamide copolymers; slightly network crosslinked products of any of the foregoing copolymers; partially neutralized polyacrylic acid; slightly network crosslinked products of partially neutralized polyacrylic acid; and mixtures thereof.

37. The absorbent composite according to claim 10 wherein said macrostructure is a sheet having a thickness of at least about 0.2 mm and a density of from about 0.6 to about 1.1 g/cc.

\* \* \* \* \*

UNITED STATES PATENT AND TRADEMARK OFFICE
CERTIFICATE OF CORRECTION

PATENT NO. : 5,536,264
DATED : July 16, 1996
INVENTOR(S) : Hsueh, et. al.

It is certified that error appears in the above-indentified patent and that said Letters Patent is hereby corrected as shown below:

```
Col.  2, line 18, "5.102,597" should read --5,102,597--.
Col.  7, line  8, "composite, in" should read --composite. In--.
Col.  7, line 30, "JA-67U" should read --JA-67U.--.
Col.  7, line 46, "interconnected," should read --interconnected--.
Col. 10, line 62, "71 a" should read --71a--.
Col. 12, line 34, ")in" should read --) in--.
Col. 19, line  2, "which" should read --of which--.
Col. 21, line 59, "Foam" should read --foam--.
Col. 28, line 41, "Kymene200" should read --Kymene®--.
Col. 38, line 35, "sillier" should read --slitter--.
Col. 38, line 37, "in" should read --In--.
Col. 41, line  6, "in" should read --In--.
Col. 46, line 12, "slits to" should read --slits--.
Col. 46, line 53, "non-continuous to" should read --non-continuous--.
Col. 47, line 24, "remain to" should read --remain--.
Col. 56, line 19, "Flaps"," should read --Flaps",--.
Col. 61, line 14, claim 23, "21" should read --22--.
Col. 62, line 17, claim 35, "10" should read --34--.
```

Signed and Sealed this

Third Day of June, 1997

*Attest:*

BRUCE LEHMAN

*Attesting Officer*  Commissioner of Patents and Trademarks